(12) United States Patent
Weisman et al.

(10) Patent No.: US 9,913,887 B2
(45) Date of Patent: Mar. 13, 2018

(54) *UREAPLASMA* VACCINE AND ANTIBODIES

(71) Applicant: Baylor College of Medicine, Houston, TX (US)

(72) Inventors: Leonard Weisman, Houston, TX (US); Lingkun Kong, Pearland, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 14/968,074

(22) Filed: Dec. 14, 2015

(65) Prior Publication Data

US 2016/0175418 A1 Jun. 23, 2016

Related U.S. Application Data

(62) Division of application No. 14/114,703, filed as application No. PCT/US2012/035779 on Apr. 30, 2012.

(60) Provisional application No. 61/480,639, filed on Apr. 29, 2011.

(51) Int. Cl.
| | |
|---|---|
| *C07K 16/00* | (2006.01) |
| *A61K 39/02* | (2006.01) |
| *C07K 16/12* | (2006.01) |
| *G01N 33/569* | (2006.01) |
| *A61K 39/00* | (2006.01) |

(52) U.S. Cl.
CPC .......... *A61K 39/0208* (2013.01); *A61K 39/02* (2013.01); *A61K 39/0241* (2013.01); *C07K 16/1253* (2013.01); *G01N 33/56911* (2013.01); *A61K 2039/53* (2013.01); *G01N 2333/30* (2013.01); *G01N 2469/10* (2013.01)

(58) Field of Classification Search
CPC .................................................. A61K 39/0208
See application file for complete search history.

(56) References Cited

U.S. PATENT DOCUMENTS

| | | |
|---|---|---|
| 3,826,364 A | 7/1974 | Bonner et al. |
| 4,284,412 A | 8/1981 | Hansen et al. |
| 4,498,766 A | 2/1985 | Unterleitner |
| 4,578,770 A | 3/1986 | Mitani |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 4,661,913 A | 4/1987 | Wu et al. |
| 4,714,682 A | 12/1987 | Schwartz |
| 4,767,206 A | 8/1988 | Schwartz |
| 4,774,189 A | 9/1988 | Schwartz |
| 4,857,451 A | 8/1989 | Schwartz |
| 4,989,977 A | 2/1991 | North |
| 5,160,974 A | 11/1992 | Siegel et al. |
| 5,478,722 A | 12/1995 | Caldwell |
| 6,939,319 B1 | 9/2005 | Anstead et al. |
| 7,438,912 B2 | 10/2008 | Meinke et al. |
| 2002/0114818 A1 | 8/2002 | Schmaljohn et al. |
| 2004/0067905 A1 | 4/2004 | Krieg |
| 2006/0263389 A1 | 11/2006 | Stacy et al. |
| 2006/0292176 A1 | 12/2006 | Vakharia |
| 2010/0183673 A1 | 7/2010 | Balint et al. |

OTHER PUBLICATIONS

Sun et al (Yunyang Yixueyuan Xuebao vol. 29 (1), pp. 19-21, Jan. 2010).*
International Search Report and Written Opinion dated Sep. 10, 2012, in corresponding International Application PCT/US2012/035779.
International Preliminary Report on Patentability (Chapter I) dated May 17rch 25, 2014, in corresponding International Application PCT/US2012/035779.
Australian Patent Examination Report No. 1 dated Aug. 9, 2016 in corresponding Australian Patent Application No. 2012249264.
Partial Supplementary European Search Report dated Mar. 26, 2015, in corresponding European Patent Application No. 12776815.8, filed Apr. 30, 2012.
Supplementary European Search Report and Written Opinion dated Jul. 14, 2015, in corresponding European Patent Application No. 12776815.8, filed Apr. 30, 2012.
Kong F. et al., "Comparative analysis and serovar-specific identification of multiple-banded antigen genes of Ureaplasma urealyticum biovar 1.", Journal of Clinical Microbiology, 1999, vol. 37, No. 3, pp. 538-543.
Vancutsem E. et al., "Production of recombinant antigens of *Ureaplasma parvum* serotypes 3 and 6 for development of a serological assay.", Clinical and Vaccine Immunology, 2008, vol. 15, No. 3, pp. 447-451.
Zimmerman C.-U.R. et al., "Alternate phase variation in expression of two major surface membrane proteins (MBA and UU376) of *Ureaplasma parvum* serovar 3.", FEMS Microbiol. Lett., 2009, vol. 292, pp. 187-193.
Sims A.C. et al., "Immunological characterization of oral *Salmonella* vaccines against Mycoplasma *pneumoniae* and *Ureaplasma urealyticum*", Abstracts of the General Meeting of the American Society for Microbiology, 1995, vol. 95, p. 298.
Sims A.C. et al., "Construction and characterization of oral *Salmonella* vaccines against *Mycoplasma pneumoniae* and *Ureaplasma urealyticum*", Abstracts of the General Meeting of the American Society for Microbiology, 1994, vol. 94, p. 169.
Monecke S. et al., "Phase variation of the multiple banded protein in *Ureaplasma urealyticum* and *Ureaplasma parvum*", International Journal of Medicine Microbiology ,2003, vol. 293, No. 2-3, pp. 203-211.
G L Mulira et al: "Immune response of heifers to vaginal submucosal or subcutaneous vaccination and intravaginal challengr with *Ureaplasma diversum*", Canadian Journal of Veterinary Research, vol. 58, No. 2, Apr. 1, 1994, pp. 109-113.
C. L. Knox et al: "The Severity of *Chorioamnionitis* in Pregnant Sheep Is Associated with In Vivo Variation of the Surface-Exposed Multiple-Banded Antigen/Gene of *Ureaplasma parvum*", Biology of Reproduction, vol. 83, No. 3, Jun. 2, 2010, pp. 415-426.

(Continued)

*Primary Examiner* — Albert M Navarro
(74) *Attorney, Agent, or Firm* — David J. Kulik; Williams Mullen, PC

(57) ABSTRACT

The present invention encompasses methods and compositions for *Ureaplasma* infection prevention and/or treatment. In specific cases, the invention concerns vaccines for *Ureaplasma*, including DNA vaccines. In certain embodiments, the invention regards vaccines directed towards the multiple-banded antigen(s) of *Ureaplasma*.

6 Claims, 12 Drawing Sheets

(56) References Cited

OTHER PUBLICATIONS

Cheng et al: "Identification of serotype 1-, 3-, and 6-specific antigens of *Ureaplasma urealyticum* by using monoclonal antibodies", Journal of Clinical Microbiology, vol. 32, No. 4, Apr. 1, 1994, pp. 1060-1062.
Zheng et al: "Serotype diversity and antigen variation among invasive isolates of *Ureaplasma urealyticum* from neonates", Infection and Immunity, Aug. 1, 1992, pp. 3472-3474. Retrieved from the Internet: URL:http://iai.asm.org/content/60/8/3472.abstract.
Xiaotian Zheng et al: "Epitope Mapping of the Variable Repetitive Region within the MB Antigen of *Ureaplasma urealyticum*", Clinical and Diagnostic Laboratory Immunology., vol. 3, No. 6, Jan. 1, 1996, pp. 774-778.
A Naessens et al: "Serotypes of *Ureaplasma urealyticum* isolated from normal pregnant women and patients with pregnancy complications", Journal of Clinical Microbiology, Feb. 1, 1988, pp. 319-322. Retrieved from the Internet: URL:http://jcm.asm.org/content/26/2/319.abstract.
D. Baxter: "Active and passive immunity, vaccine types, excipients and licensing", Occupational Medicine, vol. 57, No. 8, Dec. 1, 2007, pp. 552-556.
Lewis, P. J. et al: "DNA vaccines: a review", Advances in Virus Research, Academic Press, vol. 54, Jan. 1, 1999, pp. 129-188.
M. Roberts, et al: "Comparison of Abilities of *Salmonella enterica* Serovar *Typhimurium* aroA aroD and aroA htrA Mutants to Act as Live Vectors", Infection and Immunity, vol. 68, No. 10, Oct. 1, 2000, pp. 6041-6043.
Zheng, X. et al, "Epitope Mapping of the Variable Repetitive Region within the MB Antigen of *Ureaplasma urealyticum*," Clinical and Diagnostic Laboratory Immunology (Nov. 1996) 3(6):774-778.
Plotkin et al. (Vaccines WB Saunders Company, p. 571, 1988).
Huntley et al., "Expression Library Immunization Confers Protection against *Mycobacterium avium* subsp. paratuberculosis infections," Infection and Immunity, Oct. 2002, vol. 37, No. 10. pp. 6877-6884.
Zhang Ju, et al., "Cloning and Expression of the N-terminal segment of URAI MB in *E. coli*," J. Mod. Lab. Med., vol. 17, No. 3, pp. 1-3, Aug. 2002.
G. L. Mulira, et al., Humoral and Secretory Antibodies to *Ureaplasma diversum* in Heifers following Subcutaneous Vaccination and Vaginal Infection, Can J. Vet Res, 1994; 58: 104-08.
First Office Action dated Dec. 22, 2014 in corresponding Chinese Patent Application No. CN201280029051.6.
Second Office Action dated Oct. 23, 2015 in corresponding Chinese Patent Application No. CN201280029051.6.
Third Office Action dated Jul. 1, 2016 in corresponding Chinese Patent Application No. CN201280029051.6.
European Search Opinion dated Jul. 14, 2015 in European Patent Application No. 12776815.8, filed Apr. 30, 2012.

\* cited by examiner

SEQUENCE LISTING

```
<160> NUMBER OF SEQ ID NOS: 4

<210> SEQ ID NO 1
<211> LENGTH: 7
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (2)..(3)
<223> OTHER INFORMATION: n is a, c, g, or t
```

<400> SEQUENCE: 1 annatgg                                                              7

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
tgttcatatt ttttatcag                                                19

<210> SEQ ID NO 3
<211> LENGTH: 24
<212> TYPE: DNA
<213> ORGANISM: Artificial Sequence
<220> FEATURE:
<223> OTHER INFORMATION: Synthetic primer

<400> SEQUENCE: 3
ccaaatgacc ttttgtaact agta                                          24

<210> SEQ ID NO 4
<211> LENGTH: 970
<212> TYPE: DNA
<213> ORGANISM: Ureaplasma parvum serovar 6 str. ATCC 27818

<400> SEQUENCE: 4
gtatttgcaa tctttatatg ttttcgttaa aattaaaaat taattactat aaaaattatg     60
taagattaat aaatcttagt gttcatattt tttactagta ttaaattaaa acaataaaa    120 tgacatattt tttatattag gagaaccata aatgaaatta ttaaaaaata aaaaattctg    180
agctatgaca ttaggagtta ccttagttgg agctggaata gttgctatag cggcttcatg    240
ttctaattca actgttaaat ctaagttaag tagccaattt gttaaatcaa cagatgataa    300
aagtttttat gcagtttacg aaattgaaaa ctttaaagat ctaagtgata atgataaaaa    360
atcattaaat gacattgaat taatgctgc acttacatca gttgaaaaca aaacagaaaa    420
tctagttaca aaaggtcatt tggttggtga aaaaatttac gttaaattac ctcgtgaacc    480
aaaacctaat gaacaattaa ctattattaa taaaagtgga ttaatcaaga cttcaggttt    540
gttaatacct aataatttga attatcaaac agaaaaagtg aactttgaaa cagctccgaa    600
aactcaagaa ccaggtaaag aaccaggtaa agaaccaggt aaagaaccag gtaaagaacc    660
aggtaaagaa ccaggtaaag aaccaggtaa agaaccaggt aaagaaccag gtaaagaacc    720
aggtaaagaa ccaggtaaag aaccaggtaa agaaccaggt aaagaaccag gtaaagaacc    780
aggtaaagaa ccaggtaaag aaccaggtaa agaaccaggt aaagaaccag gtaaagaacc    840
aggtaaagaa ccaggtaaag aaccaggtaa agaaccaggt aaagaaccag gtaaagaacc    900
aggtaaagaa ccaggtaaag aaccaggtaa agaaccaggt aaagaaccag gtaaagaacc    960
aggtaaagaa                                                         970

UREAPLASMA VACCINE AND ANTIBODIES

This application claims priority to U.S. Provisional Application 61/480,639, filed Apr. 29, 2011, and U.S. application Ser. No. 14/114,703, filed Nov. 13, 2013, now U.S. Pat. No. 9,241,983, and International PCT Application PCT/US2012/035779, filed Apr. 30, 2012, all of which are incorporated by reference herein in their entirety.

TECHNICAL FIELD

The present invention generally concerns the fields of immunology, cell biology, molecular biology, infectious disease, and medicine. In specific embodiments, the present invention concerns immunological compositions and related methods for *Ureaplasma*, including vaccines.

BACKGROUND OF THE INVENTION

There are up to 7 species of *Ureaplasma*, The two species associated with human infection are *Ureaplasma parvum* and *Ureaplasma urealyticum*. All species within the genus *Ureaplasma*, family Mycoplasmataceae. They are prokaryotes devoid of a cell wall and hence insensitive to penicillin and gram stain. They are small (0.1-0.85 um) and best visualized in broth culture by dark-field or phase-contrast microscopy, but its pleomorphic nature makes it difficult to identify in medium. Thus, organisms typical colonies are recognized on solid medium (7-30 um) and is the sine qua non for identification. (Taylor-Robinson and Gourley, 1984)

*Ureaplasma* need urea for growth even in highly complex media and produce the enzyme urease which allows the organism to metabolize urea. (Pollack, 1986) They do not synthesize folic acid and as such are not susceptible to sulfonamides or trimethoprim. *Ureaplasma* produce hemolysin. (Furness, 1973; Shepar and Masover, 1979) *Ureaplasma* appear to attach to a variety of host cells via unique mechanisms and then invade the host cell. (Busolo et al., 1984; masover et al., 1977; Robertson et al., 1991; Saada et al., 1991; Shepard and Masover, 1979; Torres-Morquecho et al., 2010) This has been associated with cell apoptosis (Li et al., 2002) and increased inflammatory cytokines. Several have reported that Hela (McGarrity and Kotani, 1986; Smith et al., 1994) or A549 (Torres-Morquecho et al., 2010) cells can be used to study this attachment.

Serologic and genomic relationships among the established and unspeciated *Ureaplasma* species and serovars isolated from various hosts can be summarized as follows. (human) is separated into two genomic clusters (*parvum* and *urealyticum*). *Ureaplasma diversum* (bovine) has three serologic clusters that identify all *U. diversum* strains. The nonhuman primate strains form four serologic groups, and each serogroup is composed of strains isolated from primates belonging to one of four distinct zoologic primate families. The ovine-caprine strains have two serologic clusters. Canine strains form four serologic clusters but serovars 1 and 2 are closely related by DNA homology. Avian strains belong to one serogroup with two genomic clusters. (Barile M F, Pediatr Infect Dis 1986 5(6Suppl):5296-9).

*U. urealyticum* and *U. parvum* have at least 14 serotypes defined by serologic and biologic characteristics among its numerous strains. These serotypes have recently been subdivided into two biovar: *U. urealyticum* or group 2 (serotypes 2, 4, 5, 7, 8, 9, 10, 11, 12, 13); *U. parvum* or group 1 (serotypes 1, 3, 6, 14). (Robertson et al., 2001) The genome size of the various strains appears to vary widely and corresponds to the two serovar clusters. The genome size of cluster group 1 is about 760 kb, while group 2 ranges from 880 to 1,140 kb. (Robertson et al., 1990) Serovar identification can be accomplished by serology (Roberson and Stemke, 1982), immunofluorescence (Roberson and Stemke, 1982), and ELISA (Brown et al., 1981; Horotzitz et al., 1995). The latter is least labor intensive and has been reproduced (Turunen et al., 1982; Wiley and Quinn, 1984). It may be difficult to detect all serovar because of variable growth rates (Stemke and Robertson, 1985), and multiple serovar per specimen (Quinn, 1986).

The most sensitive method of isolating *Ureaplasma* consists of specimen inoculation into liquid medium and subculture to agar. (Robertson, 1978; Taylor-Robinson et al., 1967; Taylor-Robinson and Gourley, 1984; Taylor-Robinson, 1989) Colonies sometimes fail to develop when a specimen is plated directly on agar. In liquid medium, organisms are detected by their urease activity. Small colonies occur on agar generally due to lack of the classical fried-egg appearance, but improved medium has increased colony size, and manganous sulfate or calcium chloride, both sensitive indicators of ammonia, result in dark brown *Ureaplasma* colonies. (Shepard and Masover, 1979; Taylor-Robinson and Gourlay, 1984; Taylor-Robinson, 1989)

The multiple banded antigen (MBA) gene is present in all serovar of *Ureaplasma* (Teng et al., 1994). This gene appears to play a significant role in the organism's virulence (Kong et al., 1999), and the gene's 5' regions are markers of biovar specificity and diversity (Teng et al., 1994). This region can not only be used to differentiate *U. parvum* from *U. urealyticum*, it indicates that there may be 5 MBA genotypes of the *U. urealyticum* species: A (serovars 2, 5, 8), B (serovar 10), C (serovars 4, 12, 13), D (serovar 9), E (serovars 7, 11). The MBA gene has been cloned and sequenced. (Zheng et al., 1994) The MBA gene consists of a conserved section encoding both a signal peptide and a membrane anchor, and a variable section encoding a number of uniform repeating units. (Zimmerman et al., 2011) Thus, selection of that portion of the MBA gene that codes for a constant region is an excellent target for vaccine or antibody development, in specific embodiments of the invention. The MBA gene for serotype 6 was selected for initial development of the vaccine of the invention, because it is a frequently isolated clinical serotype. (Vancutsem et al., 2008) The MBA appears significant in attachment of the organism. (Monecke et al., 2003; Torres-Morquecho et al., 2010) MBA also appears to activate NF-kappaB through TLR1, TLR2 and TLR6 and induce tumour necrosis factor-alpha (TNFalpha). (Shimizu et al., 2008) The number of MBA variants in vivo is inversely related to the development of clinical inflammation. (Knox et al., 2010)

Simple and rapid methods of *Ureaplasma* identification have been developed, but now only confirm culture. A solid phase enzyme immunoassay is not reliable. (Taylor-Ronbinson, 1989) A whole chromosome DNA probe was insensitive (especially <$10^3$ ccu/ml) and was positive for culture-negative specimens. (Roberts et al., 1987) A PCR for *Ureaplasma* appears a very good indicator of infection. (Blanchard and Gautier, 1990; Willoughby et al., 1990) and clinical evaluations have confirmed this (Abele-Horn et al., 1996; Blanchard et al., 1993; Cunliffe et al., 1996), but commercial kits are not yet readily available.

Clinical Significance of Organism: *Ureaplasma* is a sexually transmitted infection associated with a broad range of clinical diseases in men and women including non-gonococcal urethritis, urinary stone formation, suppurative arthritis, and infertility. In men, it causes non-gonococcal urethritis and prostatitis. In women it causes pelvic inflammatory disease, recurrent abortion, chorioamnionitis, stillbirths, premature birth, low birth weight, and postpartum endometritis. In newborn babies it is associated with several diseases including pneumonia, sepsis, meningitis, osteomyelitis, death, intraventricular hemorrhage, periventricular leukomalacia, necrotizing enterocolitis (Pediatr. Res. 2011 May; 69(5 Pt 1):442-7, and chronic lung disease. (O'Leary, 1990; Pinna et al., 2006; Waites et al., 2005) However, there is variable occurrence of these diseases in patients colonized with this organism. (Krause and Taylor-Robinson, 1992) The variable development of disease in colonized patients indicates a virulence factor among pathogenic strains, or antibody, variability or both.

Data on the genital tract colonization of non-pregnant women are limited, but appear high in sex workers (44%), STD clinic clients (40%) (Kong et al., 1999), family planning clinic (43%) (Domingues et al., 2002), symptomatic (48%) and asymptomatic (22%) STD clinic patients (Gupta et al., 2008), In addition *Ureaplasma* has been isolated from the semen of 12% (9% *urealyticum*, 3% *parvum*) of all men with infertility compared to 3% (2% *parvum*, 1% *urealyticum*) of those who are fertile (Zeighami et al., 2009).

Colonization of the lower genital tract with *Ureaplasma* in pregnant women is very common varying from 44 to 88%. (Carey et al., 1991; Cassell et al., 1993; Eschenbach, 1993; Kundsin et al., 1996; Luton et al., 1994) Colonization of the lower genital tract with serotype 3 or 6 *Ureaplasma* is associated with an MBA antibody response to the variable region of these *Ureaplasma* serotypes in 51% of women while 15% of women who were not-colonized with these organisms demonstrated the same antibody. (Vancutsem et al., 2008)

Colonization of the upper genital tract or amniotic fluid with *Ureaplasma* in pregnant women appears to be strongly associated with adverse pregnancy outcomes including spontaneous miscarriage, pre-term labor, pre-labor rupture of membranes, and post-partum endometritis and may occur without microscopic or clinical signs of inflammation. (Andrews et al., 1995; Cassell et al., 1983; Font et al., 1995; Gray et al., 1992; Hazan et al., 1995; Horowitz et al., 1995; Kundsin et al., 1996)

The inventors recently completed a prospective case-control study to determine if *Ureaplasma* colonization or infection of the placenta is associated with an increase in adverse pregnancy outcome, in particular premature birth. (Okunola et al., 2006; Okunola et al., 2007) Two hundred fifty-two women who gave birth at three Baylor affiliated hospitals (St Luke's Episcopal Hospital, Methodist Hospital, and Ben Taub General Hospital) during an 18 month period participated. These women were composed of 3 groups: 58 gave birth to premature infants between 20 and 30 wks gestation; 27 developed perinatal complications (prolonged rupture of membranes >18 hours, premature rupture of membranes, maternal fever >100.4° F., or clinical chorioamnionitis or endometritis) and gave birth to term infants; 167 had no perinatal complications and gave birth to term infants. Over 40% of those women who gave birth to premature infants (p<0.0001) or who had perinatal complications with a term birth (p<0.004), had placental colonization or infection with *Ureaplasma*, compared to term births without perinatal complication who had a <15% *Ureaplasma* placental colonization or infection. No maternal demographic, medical, surgical, or pregnancy factors appear to predict *Ureaplasma* infection or colonization of the placenta. Of the 58 preterm infants, (Molina et al., 2010) 23 placentas were culture positive for *Ureaplasma* (40%). Infants whose placenta were positive were not different then those who were negative, in either gestation (26±2.4 vs 26±2.1 wks), birth weight (884±278 vs 890±401), male sex (44% vs 54%), race (38% vs 31%), and prenatal factors. 70% of the *Ureaplasma* were biovar 1, and of those all were either serotypes 3, 6, or 14. Of infants who survived to 36 wks corrected gestational age (CGA), BPD developed in 69% with *Ureaplasma* in their placenta compared to 37% of those with a negative culture (p=0.062). Of all infants, death or BPD resulted by 36 wks CGA in 78% with *Ureaplasma* in their placenta compared to 51% of those with a negative culture (p=0.054). Antenatal exposure of the fetus to *Ureaplasma* may increase the risk of BPD or death. Strategies to prevent *Ureaplasma* placenta colonization may decrease premature birth and its complications.

To determine those women at risk for placenta colonization, the inventors recently completed a prospective study (Weisman et al., 2009) of 290 women evaluating *Ureaplasma* vaginal colonization, and the following was observed: 44% of women at 16 wks gestation had vaginal *Ureaplasma* colonization; colonization did not change significantly throughout gestation; 32% of all colonized women developed placental *Ureaplasma* infection (12% of all); all women with placental *Ureaplasma* infection had vaginal colonization at 16 wks gestation. In preterm births: 67% had vaginal colonization; this did not change throughout gestation; 62% of colonized women developed placental *Ureaplasma* infection (42% of all). Vaginal colonization at 16 wks gestation is an early marker for those at risk of poor pregnancy outcome and potential target intervention, in certain cases of the invention. Although other conditions (e.g. other infections, anatomic abnormalities, endocrine disorders, maternal medical conditions, etc.) may contribute to poor pregnancy outcome, *Ureaplasma* colonization of the placenta appears a significant association. If those at risk for poor outcome can be identified early, intervention strategies including antibiotics or more likely vaccines could provide protection from *Ureaplasma* and adverse pregnancy outcomes.

It has been proposed that *Ureaplasma* should be eradicated from the urogenital tracts of women and their partners. (Kundsin et al., 1996) *Ureaplasma* is not susceptible in vitro to penicillins, sulfonamides, trimethoprim, aminoglycosides, and clindamycin, but are generally (about 90%) susceptible in-vitro to tetracyclines, and variably to macrolides (e.g. erythromycin). (Cassell et al., 1993) The inventors have confirmed in recent studies the variable susceptibility of *Ureaplasma* to erythromycin in vitro. In view of the high colonization rate and sexual transmission rates of *Ureaplasma*, it is unlikely that such strategies will be effective in its eradication. In addition, this organism has been observed to persist in the genital tract despite antibiotic treatment. In couples attending an infertility clinic this organism persisted in the genital tract despite antibiotic treatment. (Hipp et al., 1983) Routine use of intraoperative prophylactic-antimicrobial therapy at Cesarean delivery did not effect *Ureaplasma* colonization of the chorioamnion at delivery. (Andrews et al., 1995) Macrolides (Eschenbach et al., 1991; Mazor et al., 1993; Romero et al., 1993) have not been reliable in eradicating genital tract *Ureaplasma* or adverse perinatal outcomes in two randomized controlled trials. Although newer antibiotics such as glycylcyclines (Kenny and Cartwright, 1994) and quinolones (Kenny and Cartwright, 1996) may prove more effective, their safety and efficacy during pregnancy are unproven.

It has been suggested, but not demonstrated, that lack of specific antibody may be critical for preventing *Ureaplasma* infection, because specific protein antibody may inhibit growth in vitro. (Cassell et al., 1993) Hypogammaglobulinemic patients have an increased susceptibility to *Ureaplasma*. (Taylor-Robinson et al., 1986) Serological studies of hypogammaglobulinemic patients (Volger et al., 1985), pre-term infants (Quinn et al., 1983), and women with recurrent spontaneous abortions (Quinn et al., 1983) support this concept. Increased susceptibility of infants of <30 wks gestational age to *Ureaplasma* induced respiratory disease may be related to their hypogammaglobulinemia (Ballow et al., 1986) or to their lack of specific antibody (Cassell et al., 1988; Cassell et al., 1988).

It has been suggested, but not demonstrated, that monoclonal antibodies to specific protein antigens of *Ureaplasma* can inhibit growth of these organisms in vitro and indicates that specific antibody may be important for host defense. (Watson et al., 1990) There is a long-felt need in the art to provide useful methods and reagents for *Ureaplasma* vaccines and methods and compositions to prevent or treat *Ureaplasma* infection.

BRIEF SUMMARY OF THE INVENTION

The present invention is directed to immunological methods and compositions for *Ureaplasma*, including vaccines and antibodies for prevention and/or treatment of mammalian infection, including, for example, a DNA vaccine for its related antibodies. In particular embodiments, the compositions are useful to prevent infection and also to reduce the deleterious effects of infection once the individual is infected. In specific embodiments, the composition may be employed for a female or a male or both. The compositions may be utilized in adults, adolescents, children, or infants. In specific cases, the composition is delivered to an individual prior to the onset of becoming sexually active, including becoming sexually active for the first time. The type of sexual activity may be of any kind. An adolescent may be vaccinated at or about the time of onset of puberty. In certain cases, a female is vaccinated prior to pregnancy, while in other cases a female is vaccinated during pregnancy. In some embodiments of the invention, an individual susceptible to or having immune deficiency syndromes that are either congenital (e.g. agammaglubulinemia) or acquired (e.g. patients with cancer receiving or not receiving therapy) are administered methods and compositions of the invention. In specific embodiments, an individual in early childhood is treated with at least some aspects of the invention, including antibody or vaccine compositions. In specific cases, an individual after the diagnosis of cancer or the diagnosis of immune deficiency is provided methods and/or compositions of the invention. In certain cases, a male or a female is vaccinated when sexually active or prior to being sexually active.

An individual that is administered compositions and methods of the invention may be susceptible to having *Ureaplasma* infection, may be suspected of having *Ureaplasma* infection, or may be known to have *Ureaplasma* infection or high risk for infection. In at least certain instances that the individual is known to have *Ureaplasma* infection, the individual may also be administered another therapy for *Ureaplasma*, including certain antibiotics, for example.

*Ureaplasma* infection during pregnancy and delivery has been suggested to cause abnormal brain development in the baby in a few clinical studies and one animal study. The role of *Ureaplasma* infection during pregnancy on brain development abnormalities is encompassed in the invention. It appears to not only affect the long term behavior of premature babies, but could have a role in other brain conditions associated with inflammation including brain injury due to lack of oxygen, blood infection, brain infection, and severe jaundice in the newborn, and seizures, cerebral palsy, autism, and attention deficit hyperactivity in pediatrics. The present disclosure encompasses a mouse model and addresses the impact of *Ureaplasma* infection during pregnancy on brain inflammation and behavior of the baby and also encompasses methods and compositions for preventing brain development abnormalities in a fetus or infant.

*Ureaplasma* infection's role in brain development abnormalities is an important area of investigation, because it appears to not only affect the development outcome of preterm infants, but in some cases of the invention it appears to have a role in other brain conditions associated with inflammation, including hypoxic ischemic perinatal brain injury, sepsis, meningitis, and hyperbilirubinemia in the neonate, and seizures, cerebral palsy, autism spectrum disorders, and attention deficit hyperactivity disorders in pediatrics. The present invention includes the impact of perinatal *Ureaplasma* infection and inflammation on brain development.

The present invention includes a murine model of antenatal *Ureaplasma* chorioamnionitis, in certain cases. In some embodiments, it includes determination of the effect of *Ureaplasma* chorioamnionitis on brain development in the suckling mouse, including behavior and memory, brain pathology and structure, and molecular signals. In certain embodiments, the present invention includes determination of antenatal maternal administration of an *Ureaplasma* recombinant DNA (rDNA) vaccine, protein vaccine, or monoclonal antibody that affects *Ureaplasma* related changes in brain development.

In some embodiments of the invention, there is an immunological composition (such as an antibody) that immunologically reacts with a multiple-banded antigen of *Ureaplasma*, said composition comprised in a pharmacologically acceptable excipient. In specific embodiments, the composition is further defined as a vaccine, including a DNA, protein, or antigen vaccine. In specific embodiments, the vaccine comprises one or more DNA polynucleotides, protein, or antigen. In certain cases, the vaccine comprises monoclonal or polyclonal antibodies.

Certain embodiments include diagnosis of *Ureaplasma* infection, for example by PCR. Specific embodiments utilize antibodies of the invention for *Ureaplasma* detection, such as from an individual or from a culture.

In particular embodiments, the antibodies of the invention are employed for cell culture and media contamination applications. Exemplary cell culture lines and media are well known in the art (Hassan M, et al. J Basic Microbiol. 2010; Harasawa R, et al. Res Microbiol. 1993; Kong F, et al. Appl Environ Microbiol. 2001; Wang H, et al. Appl Environ Microbiol. 2004; Sung H, et al. J Microbiol. 2006. Johansson K E, et al. Molecular and Cellular Probes. 1990; Teyssou R, et al. Molecular and Cellular Probes. 1993). In at least some specific aspects, the antibody directly kills the organism in media without complement or neutrophils or macrophages.

In some embodiments of the invention, there is a DNA vaccine comprising a polynucleotide encoding part or all of a *Ureaplasma* antigen. In specific embodiments, the antigen is urease, UU376 gene product, virulence gene product, or urea transporter, or wherein the polynucleotide comprises MBA N-terminal paralogs, 16S rRNA, the area upstream of the Urease A gene, the Urease A-Urease B spacer, the Urease B-Urease C spacer, or the 16S-23S rRNA intergenic spacer region. In certain aspects, the vaccine is further defined as a DNA vaccine comprising a polynucleotide encoding at least one multiple-banded *Ureaplasma* antigen.

In nucleic acid vaccine embodiments, the polynucleotide may be further defined as follows: a) comprises a strong viral promoter; b) comprises Mason-Pfizer monkey virus (MPV)-CTE with or without rev; c) comprises Intron A or an intron from SV40 or Raucous sarcoma; d) strong polyadenylation/transcriptional termination signal; e) expresses the multiple binding proteins from more than one species, biovar, serotype or strain of *Ureaplasma*; f) comprises codons for pathogenic mRNA; g) comprises an immune enhancer (such as from human granulocyte-macrophage colony-stimulating factor); h) comprises a N-terminal ubiquitin signal; i) comprises strings of minigenes (or MHC class I epitopes from) different pathogens or oligonucleotides (for example, wherein the strings of MHC class I epitopes from different pathogens or oligonucleotides comprise a CpG motif); j) comprises a TH epitope; or k) a combination thereof.

In certain aspects of the vaccine embodiments, the vaccine may be further defined as comprising two *Ureaplasma* antigens. In specific cases, a DNA vaccine is further defined as comprising ANNATGG in front of the start codon.

In particular embodiments, there is a vaccine that immunologically reacts with a multiple-banded antigen of *Ureaplasma*, said vaccine comprised in a pharmacologically acceptable excipient. In a specific embodiment, the vaccine comprises a peptide or polypeptide of the multiple-banded antigen. In specific aspects, the vaccine comprises an antibody that immunologically reacts with the multiple-banded antigen.

In one embodiment of the invention, there is a kit comprising a vaccine of the invention housed in a suitable container.

In one embodiment of the invention, there is a method of preventing *Ureaplasma* infection in an individual or reducing symptoms of *Ureaplasma* infection in an individual, comprising the step of delivering a therapeutically effective amount of an antibody or vaccine of the invention to the individual. In specific embodiments, the individual is a human, cow, female, male, etc. In some cases, the individual is a female or male prior to a first sexual activity or the individual is a female prior to pregnancy. The vaccine may be delivered to a pregnant female. The individual may be an infant, child, or adolescent. In some embodiments, there is a method of preventing *Ureaplasma* infection in a cell media, comprising the step of delivering to the media an effective amount of antibodies that recognize the conserved region of *Ureaplasma* multiple-banded antigen or the 5' end of the multiple-banded antigen.

In certain embodiments, the antibodies or vaccine are delivered by injection, such as intramuscular, intravenous, subcutaneous, intraperitoneal, by Gene Gun, by pneumatic injection, or it comprises liposomes. In specific cases, when the vaccine comprises DNA the Gene Gun comprises delivery of DNA coated gold or tungsten beads via epidermal delivery. In certain cases, when the vaccine comprises DNA the pneumatic injection is via epidermal delivery. Particular aspects of the invention further comprising multiple deliveries to the individual, such as deliveries being separated by years, months, weeks, or days, for example. In specific cases, the multiple deliveries are separated by one month or more. In specific cases, the multiple deliveries are separated by between two and ten years. In some embodiments, the vaccine or antibody is delivered in the amniotic cavity or vaginally, for example.

In some embodiments, there are antibodies that immunologically react with a conserved region of *Ureaplasma* multiple-banded antigen or the 5' end of the multiple-banded antigen. In certain embodiments, there is a method of preventing *Ureaplasma* infection in an individual or reducing symptoms of *Ureaplasma* infection in an individual, comprising the step of delivering to the individual a therapeutically effective amount of antibodies that recognize the conserved region of *Ureaplasma* multiple-banded antigen or the 5' end of the multiple-banded antigen.

Thus, in embodiments of the invention there is cloning and expression of a conserved section of *Ureaplasma* multiple banded antigen gene, such as in the exemplary pVAX1 vector. The data provided herein includes efficacy demonstrated in-vitro (IgG bacterial binding, IgA bacterial binding, bacterial killing) and in-vivo (animal protection). This exemplary work demonstrated that this vaccine through its antibodies and, optionally, other factors was effective in binding *Ureaplasma* in-vitro, neutralizing (killing) *Ureaplasma* in-vitro independent of other immune factors (complement and neutrophils), and providing protection (decreased mortality and bacteremia) to animals infected with *Ureaplasma*. In embodiments of the invention, vaccine-related antibodies have application in the prevention and treatment of human infection, prevention and treatment in animal infection, and prevention and treatment of media that has been contaminated with *Ureaplasma*.

Also encompassed in the invention are optimized vaccine delivery, dose, and schedule methods, and the immunologic response to the vaccine and related antibodies is evaluated herein.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention

Figure 1:
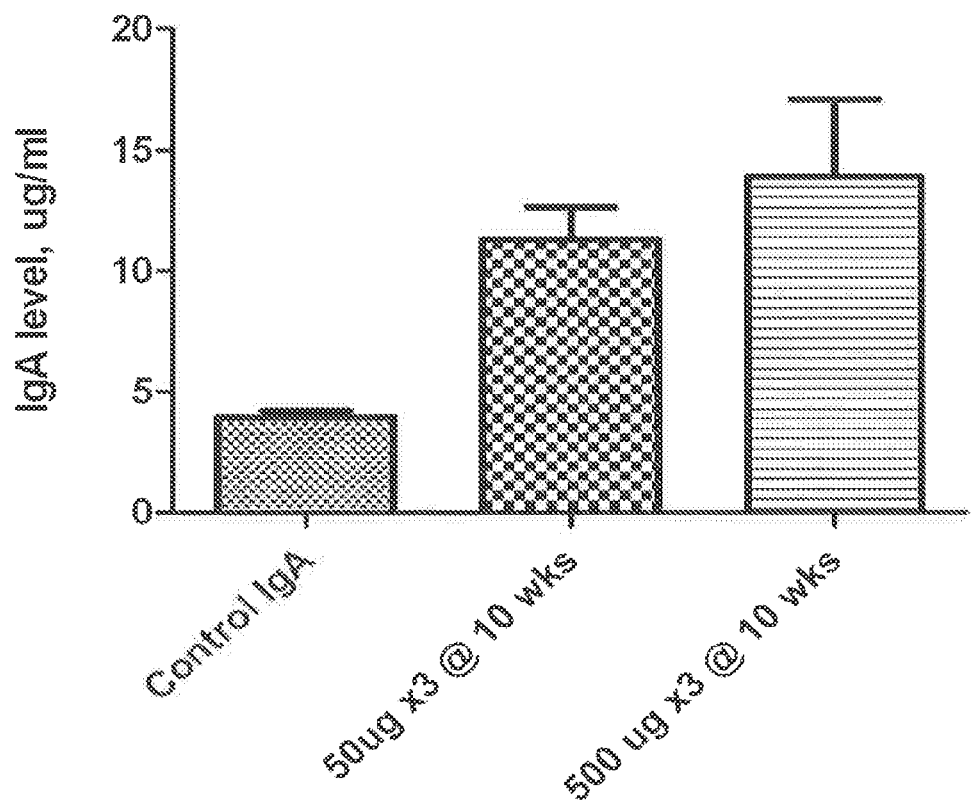
FIG. 1. Serum IgA level in vaccinated mice.

Exemplary multiple-banded antigens of *Ureaplasma* include at least the following from different serovars, denoted by their GenBank® sequences, all of which are incorporated by reference herein: AAD09745.2; AAD09744.2; AAD09743.2; AAD02701.2; AAD02700.2; AAD02699.2; AAD02698.2; AAD02697.2; AAD02696.2; AAD02695.2; AAD02694.2; AAD02693.2; AAD02692.2; AAD00075.1; AAC41437.1; AAD00077.1; AAD00076.1; AAB38978.1; AAD19956.1; AAD19955.1; AAD19954.1; AAD19953.1; AAD19952.1; AAD19951.1; AAD19950.1; AAD19949.1; AAD19948.1; AAD19947.1; AAD19946.1; NP_078209.1; YP_002284809.1; YP_002284808.1; YP_002284599.1; YP_002284567.1; YP_002284811.1; YP_002284585.1; YP_001752457.1; ACI60346.1; ACI60338.1; ACI60127.1; ACI60016.1; ACI59928.1; ACI59882.1; ACA32903.1; AAF61146.1; AAF61145.1; AAF30784.1; ABU75287.1; AAT79416.1; AAT79415.1; AAT79414.1; AAT79413.1; AAT79412.1; AAT79411.1; ZP_03772473.1; ZP_03772432.1; ZP_03772428.1; ZP_03772407.1; ZP_03772313.1; ZP_03772151.1; ZP_03003758.1; ZP_02997126.1; ZP_02570847.2; ZP_02553955.2; ZP_02555017.2; ZP_02691486.2; ZP_02691471.2; ZP_02690312.2; ZP_02691487.1; ZP_02691469.1; ZP_02690307.1; ZP_02690299.1; ZP_02570851.1; ZP_02570848.1; ZP_02555874.1; ZP_02555020.1; ZP_02555016.1; ZP_02555015.1; ZP_02555013.1; ZP_02553953.1; ZP_03771933.1; ZP_03771930.1; ZP_03771929.1; ZP_03771924.1; ZP_03771712.1; ZP_03771427.1; ZP_03771410.1; ZP_03771378.1; ZP_03771338.1; ZP_03771299.1; ZP_03771272.1; ZP_03771271.1; EEH02496.1; EEH02495.1; EEH02491.1; EEH02279.1; EEH02194.1; EEH01977.1; EEH01945.1; EEH01905.1; EEH01866.1; EEH01840.1; EEH01837.1; EEH01836.1; EEH01707.1; EEH01666.1; EEH01662.1; EEH01641.1; EEH01547.1; EEH01385.1; ZP_03206353.1; EDY74356.1; ZP_03079858.1; ZP_03079727.1; EDX53837.1; EDX53694.1; EDX53543.1; EDX53525.1; EDX53195.1; ZP_02558219.2; ZP_02558216.1; ZP_02558215.1; EDU67250.1; EDU67198.1; EDU56636.1; EDU56624.1; EDU56617.1; EDU56613.1; EDU19480.1; EDU19358.1; EDU06306.1; EDU06277.1; EDU06259.1; EDU06258.1; EDU06213.1; EDT87551.1; EDT87494.1; EDT48735.1; EDT48714.1; EDT48712.1; EDT48706.1; and/or EDT48704.1.

In certain embodiments of the invention, an immunological composition, such as a vaccine, is effective by being able to immunologically react with a variety of multiple-banded antigens, and in some embodiments the immunogical composition, including a vaccine, is effective against a single multiple-banded antigen. The immunological compositions may recognize multiple serotypes of a biovar, in some cases. In specific cases, the immunological compositions recognize an antigen that is conserved between biovars.

Multiple banded antigen (MBA) is the predominant antigen recognized during infection with *Ureaplasma* and plays a role in virulence (Watson H L, et al Infect Immun 1990). It is species specific and contains cross reactive epitopes. The 5' end of the MBA gene is relatively conserved but contains some biovar and serovar specificity. The MBA contains a signal peptide and acylation site in the N-terminal region, while the C terminal region is composed of multiple six-amino-acid (encoded by 18 nucleotides) tandem repeats, which contain serovar-specific epitopes. Alteration of the copy number of the repeating units results in MBA size variation (Zheng X, et al. Ann NY Acad Sci 1994). In contrast to the repeat region, the 5' region is conserved among serovar variants (Teng L J, et al. J Clin Microbiol 1994). Although serovar specificity is determined by the composition of the C-terminal region of MBAs, there is some heterogeneity detected in the sequence of the 5' region of the MBA gene of the different serovars which allows the 14 serovars to be divided into several subgroups. Thus, in specific embodiments of the invention, the compositions are focused on the more conserved regions of the MBA so that any vaccine, antigen, or antibody would be applicable to all or most serotypes, biovars, and even species. An exemplary sequence for the conserved sequence is below:

Serotype 6 MAB cDNA sequence (AF056984) (SEQ ID NO:4):

```
  1 GTATTTGCAA TCTTTATATG TTTTCGTTAA AATTAAAAAT TAATTACTAT AAAAATTATG
 61 TAAGATTAAT AAATCTTAGT GTTCATATTT TTTACTAGTA TTAAATTAAA AACAATAAAA
121 TGACATATTT TTTATATTAG GAGAACCATA AATGAAATTA TTAAAAAATA AAAAATTCTG
181 AGCTATGACA TTAGGAGTTA CCTTAGTTGG AGCTGGAATA GTTGCTATAG CGGCTTCATG
241 TTCTAATTCA ACTGTTAAAT CTAAGTTAAG TAGCCAATTT GTTAAATCAA CAGATGATAA
301 AAGTTTTTAT GCAGTTTACG AAATTGAAAA CTTTAAAGAT CTAAGTGATA ATGATAAAAA
361 ATCATTAAAT GACATTGAAT TTAATGCTGC ACTTACATCA GTTGAAAACA AAACAGAAAA
421 TCTAGTTACA AAAGGTCATT TGGTTGGTGA AAAAATTTAC GTTAAATTAC CTCGTGAACC
481 AAAACCTAAT GAACAATTAA CTATTATTAA TAAAAGTGGA TTAATCAAGA CTTCAGGTTT
541 GTTAATACCT AATAATTTGA ATTATCAAAC AGAAAAGTG AACTTTGAAA CAGCTCCGAA
601 AACTCAAGAA CCAGGTAAAG AACCAGGTAA AGAACCAGGT AAAGAACCAG GTAAAGAACC
```

-continued

```
661 AGGTAAAGAA CCAGGTAAAG AACCAGGTAA AGAACCAGGT AAAGAACCAG GTAAAGAACC

721 AGGTAAAGAA CCAGGTAAAG AACCAGGTAA AGAACCAGGT AAAGAACCAG GTAAAGAACC

781 AGGTAAAGAA CCAGGTAAAG AACCAGGTAA AGAACCAGGT AAAGAACCAG GTAAAGAACC

841 AGGTAAAGAA CCAGGTAAAG AACCAGGTAA AGAACCAGGT AAAGAACCAG GTAAAGAACC

901 AGGTAAAGAA CCAGGTAAAG AACCAGGTAA AGAACCAGGT AAAGAACCAG GTAAAGAACC

961 AGGTAAAGAA
```

In some cases of the invention, an immunological compositions immunologically reacts with a multiple-banded antigen of *Ureaplasma* from a patient, for example, although the immunological composition itself may have been raised against an antigen having a slight modification from the naturally occurring corresponding antigen. For example, an antibody may recognize the naturally occurring antigen, such as from a patient, although the antibody may have been raised against a peptide or polypeptide sequence having less than 100% identity to the naturally occurring antigen. In specific embodiments, the antibody was raised against peptide or polypeptide sequence having 80%, 81%, 82%, 83%, 84%, 85%, 86%, 87%, 88%, 89%, 90%, 91%, 92%, 93%, 94%, 95%, 96%, 97%, 98%, or 99% identity to the sequence in the naturally occurring antigen. In some cases, the antibody was raised against peptide or polypeptide having 1, 2, 3, 4, 5, 6, 7, 8, 9, 10, or more amino acid differences compared to the sequence of the naturally occurring antigen, yet the antibody still recognizes the sequence in the naturally occurring antigen.

III. Exemplary Vaccines of the Invention

In some embodiments of the invention, there are vaccines directed against one or more *Ureaplasma* antigens. The antigens may be the multiple-banded antigen or it may be another antigen.

In some embodiments of the invention, there are several other non-Multiple Banded Antigen (MBA) antigens and they or their respective DNA could be targets for a vaccine or their antibody products for similar prevention and treatment strategies and possible diagnostic targets including: 1) the enzyme Urease that is necessary for the organism's survival. There are several Ureases (A-G) known at this time (UU428, UU429, UU430, UU431, UU432, UU433, UU434); 2) Adjacent to the MBA gene (UU375) is gene UU376, which is a *Ureaplasma*-specific conserved hypothetical gene and another potential target; 3) There appears to be virulence genes (hemolysin) including hlyC (UU072), hlyA (UU436) that are useful targets, in some aspects; 4) MBA N-terminal paralogs (UU172, UU189, UU483, UU487, UU526). Phase variation of the multiple-banded antigen (MBA) with its counterpart, the UU376 protein, results in DNA inversion at specific inverted repeats. These recombination events are dynamic and can lead to a broad spectrum of antigenic variation by which the organism could evade host immune responses; thus in specific embodiments these are targeted; 5) There are several other genes to also consider including the following, for example: a) 16S rRNA genes, b) the genes adjoining the urease genes including the area upstream of the Urease A gene, the Urease A-Urease B spacer, the Urease B-Urease C spacer, c) the 16s-23S rRNA intergenic spacer region, and/or d) urea transporter.

DNA Vaccine: In specific embodiments of the invention, the vaccines are composed of a piece of the pathogen's DNA (plasmid, for example) genetically engineered to produce at least one, two, or more specific proteins (antigens) from a pathogen. The plasmid DNA (pDNA) is injected into the cells of the body, where the host cells read the pDNA and produces its antigens. These antigens are recognized as foreign when produced and displayed by the host cells, and the host immune system triggers a range of immune responses. (Alarcon et al., 1999; Robinson and Pertmer, 2000)

Thus far, several DNA vaccines have been developed and many more are under consideration. (Kutzler and Weiner, 2008) Specifically, positive results are seen for a bird flu DNA vaccine (Cinatl et al., 2007). Veterinary DNA vaccines have been approved to: 1) protect horses from West Nile virus (Fort Dodge Animal Health Announces Approval of West Nile Virus DNA Vaccine for Horses, P R Neswire 2005, Jul. 18); 2) protect salmon from Infectious hematopoietic necrosis virus; 3) protect piglets from perinatal mortality and morbidity due to weaning; 4) treats dogs with aggressive melanoma. A preliminary study for a DNA vaccine against multiple sclerosis was reported as being effective (Stuve et al., 2007).

There are several advantages and disadvantages for DNA vaccines. (Alarcon et al., 1999; Kutzler and Weiner, 2008; Robisnson and Pertmer, 2000; Sedegah et al., 1994) The advantages include the following: subunit vaccination without risk for infection, antigen presentation by both MHC class I and II molecules, ability to polarize T-cell help toward type 1 or 2, immune response focused only on antigen(s) of interest, ease of development and production, stability of vaccine for storage and shipping, cost-effectiveness, eliminates need for peptide synthesis, expression, and purification of recombinant proteins and the use of toxic adjuvants, long term persistence of immunogen, in vivo expression ensures protein more closely resembles normal eukaryotic structure, with accompanying post-translational modifications.

DNA Vaccine Development and Design: There are several methods to optimize DNA vaccine development. 1) DNA vaccines appear to obtain the best immune response when highly active expression vectors are used. Thus, a strong viral promoter to drive the in vivo transcription and translation of the DNA or complimentary DNA of interest is useful. (Mor et al., 1995) In some embodiments the cytomegalovirus early promoter (CMV) is employed because it had higher expression rates than the SV40 promoter or Rous Sarcoma Virus promoter. 2) In some embodiments there is included Mason-Pfizer monkey virus with rev (MPV)-CTE+ rev increases envelope expression and is more immunogenic. (Muthumani et al., 2003) One can add the MPV-CTE+rev to a vaccine and attempt to increase envelope expression and immunogenicity. 3) An Intron A may sometimes be included in the plasmid vector to improve mRNA stability and thus increase protein expression. (Leitner et al., 1997) pVAX1 by Invitrogen may be included in the plasmid at this location, in some embodiments. A newer more effective vector (e.g. pVAX200-DEST by Invitrogen) may be employed. 4) Plasmids should also include a strong polyadenylation/transcriptional termination signal such as a bovine growth hormone (BGH). (Alarcon et al., 1999; Bohm et al., 1996; Robinson and Pertmer, 2000) The inventors have already done this with the pVAX1 vector and BGH is also present on the pVAX200-DEST vector. 5) Vectors that express more than one immunogen may also enhance a vaccine's efficacy and impact and be employed. (Carey et al., 1991) In some cases, there is expression of more than one immunogen in the plasmid to enhance the vaccines efficacy and impact. Specifically, one can express the multiple binding proteins (MBP) from several serotypes and strains of *Ureaplasma.* 6) To optimize vector design for maximal protein expression, one can use a codon of pathogenic mRNA for eukaryotic cells. (Lewis and Babiuk, 1999) Pathogens often have different AT contents different than the species being immunized, so altering the gene sequence of the immunogen to reflect codons more commonly used in the target species may improve its expression, in certain cases of the invention. (3) In specific embodiments, ANNATGG (SEQ ID NO:1) is employed in front of the start code. The adenovirus tripartite leader (TPL) may be utilized in certain cases. (Kutzler and Weiner, 2008) Further enhancer sequences may be utilized for the vaccine. In specific embodiments, human granulocytemacrophage colony-stimulating factor (hGM-CSF) is used in the current vaccine as an immune enhancer. (Kutzler and Weiner, 2008) 7) Immunogens can be targeted to various cellular compartments in order to improve antibody or cytotoxic T-cell responses. Plasma membrane-bound antigens are more effective at inducing antibody responses than cytosolic antigens (Robinson and Pertmer, 2000), in certain cases, and such may be used in the vaccine. 8) Cytotoxic T-cell responses can be improved by targeting antigens for cytoplasmic degradation and subsequent entry into MHC class I pathway (Robinson and Pertmer, 2000) by the addition of N-terminal ubiquitin signals (Rodriguez et al., 1997) to the stop code, and in certain embodiments such is used in the invention. 9) Conformation of the protein can also have an effect on antibody responses, with ordered structures being more effective than unordered structures, and it may be used in the invention. (Wunderlich et al., 2000) 10) Strings of MHC class I epitopes from different pathogens or oligonucleotides (e.g. CpG motif) are able to raise cytotoxic T-cell responses to a number of pathogens, especially if a TH epitope is also included (Robinson and Pertmer, 2000), and such may be employed in certain embodiments.

DNA Vaccine Delivery: DNA vaccines have been introduced into animal tissues by several different methods. (Weiner and Kennedy, 1999) These delivery methods include the following: 1) Injection via a hypodermic needle of an aqueous solution of DNA in saline by intramuscular (IM), intradermal (ID), intravenous (IV), subcutaneous (SC), or intraperitoneal (IP) route. The latter three have had variable success and all require large amounts of DNA (100-200 ug). Although these are not specialized delivery mechanisms, they are simple, lead to permanent or semi-permanent expression, lead to pDNA spread rapidly throughout the body. However, they are inefficient in their uptake, require relatively large amounts of DNA, and the Th1 response may not be the response required. Although several methods can be used to increase delivery to the cell including electroporation (Widera et al., 2000), damaging muscle fibers with myotoxins (e.g. bupivacaine) or hypertonic solutions (e.g. saline or sucrose), or more damaging injection (needle type, needle alignment, speed of injection, volume of injection) (2). Lack of practical application of these methods or their side effects potentially outweigh their benefits and at least in some cases they are not utilized. 2) Gene Gun delivery of a DNA coated gold or tungsten beads via epidermal delivery (ED) through the skin or outer membrane (vaginal mucosa), or surgically exposed muscle or other organs. This method allows the DNA to be bombarded directly into cells utilizing compressed helium as an accelerant, and requires a small amount of DNA (as little as 16 ng). However, the disadvantage is that the Th2 response may not be required and inert particles are required as carriers. 3) Pneumatic (Jet) injection of an aqueous solution of DNA by ED. The advantage is that no particles are required, DNA can be delivered to cells mm to cm below the skin or tissue surface. The disadvantage is there is significant shearing of DNA after high-pressure expulsion, a 10-fold lower expression and lower immune response has been reported, and it requires large amounts of DNA (up to 300 ug). 4) Liposome mediated delivery of several of the above-mentioned systems but particularly IM, IV, IP, and Oral or Mucosal (Nasal, Vaginal) has several advantages. It can increase the immune response substantially, increase the transfection of pDNA, and mucosally delivered liposomal-DNA complexes can result in expression at distal mucosa and the generation of IgA antibodies. The potential disadvantages are the variability of the response and thus ineffectiveness, and the possibility of toxicity secondary to the enhanced immune response. For certain cases the inventors employed the IP route with an aqueous solution to allow the most generalized distribution of the pDNA while minimizing the complexities of delivering a vaccine IV or using a more expensive delivery system (Gene Gun) or complex media (Liposome). Regardless of these methods, several factors can influence the immune responses related to injections including age and sex and may be considered in certain embodiments of the invention.

IV. General Vaccine Embodiments

For an antigenic composition to be useful as a vaccine, an antigenic composition must induce an immune response to the antigen in a cell, tissue or animal (e.g., a mammal, including a human). As used herein, an "antigenic composition" may comprise an antigen (e.g., a peptide or polypepide), a nucleic acid encoding an antigen (e.g., an antigen expression vector), or a cell expressing or presenting an antigen. In particular embodiments the antigenic composition comprises or encodes all or part of a peptide or polypeptide sequence, or an immunologically functional equivalent thereof. In other embodiments, the antigenic composition is in a mixture that comprises an additional immunostimulatory agent or nucleic acids encoding such an agent Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In certain embodiments, an antigenic composition or immunologically functional equivalent, may be used as an effective vaccine in inducing an anti *Ureaplasma* humoral and/or cell mediated immune response in an animal. The present invention contemplates one or more antigenic compositions or vaccines for use in both active and passive immunization embodiments.

A vaccine of the present invention may vary in its composition of proteinaceous, nucleic acid and/or cellular components. In a non-limiting example, a nucleic acid encoding an antigen might also be formulated with a proteinaceous adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

A. Proteinaceous Antigens

It is understood that an antigenic composition of the present invention may be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding a peptide or polypeptide comprising an antigen of the present invention in an in vitro translation system or in a living cell. Preferably the antigenic composition is isolated and extensively dialyzed to remove one or more undesired small molecular weight molecules and/or lyophilized for more ready formulation into a desired vehicle. It is further understood that additional amino acids, mutations, chemical modification and such like, if any, that are made in a vaccine component will preferably not substantially interfere with the antibody recognition of the epitopic sequence.

A peptide or polypeptide corresponding to one or more antigenic determinants of the *Ureaplasma* of the present invention should generally be at least five or six amino acid residues in length, and may contain up to about 10, about 15, about 20, about 25 about 30, about 35, about 40, about 45 or about 50 or more residues or so. A peptide sequence may be synthesized by methods known to those of ordinary skill in the art, such as, for example, peptide synthesis using automated peptide synthesis machines, such as those available from Applied Biosystems (Foster City, Calif.).

Longer peptides or polypeptides also may be prepared, e.g., by recombinant means. In certain embodiments, a nucleic acid encoding an antigenic composition and/or a component described herein may be used, for example, to produce an antigenic composition in vitro or in vivo for the various compositions and methods of the present invention. For example, in certain embodiments, a nucleic acid encoding an antigen is comprised in, for example, a vector in a recombinant cell. The nucleic acid may be expressed to produce a peptide or polypeptide comprising an antigenic sequence. The peptide or polypeptide may be secreted from the cell, or comprised as part of or within the cell.

B. Proteinaceous Antigens

In certain embodiments, an immune response may be promoted by transfecting or inoculating an animal with a nucleic acid encoding an antigen. One or more cells comprised within a target animal that expresses the sequences encoded by the nucleic acid after administration of the nucleic acid to the animal. Thus, the vaccine may comprise "genetic vaccine" useful for immunization protocols. A vaccine may also be in the form, for example, of a nucleic acid (e.g., a cDNA or an RNA) encoding all or part of the peptide or polypeptide sequence of an antigen. Expression in vivo by the nucleic acid may be, for example, by a plasmid type vector, a viral vector, or a viral/plasmid construct vector.

In preferred aspects, the nucleic acid comprises a coding region that encodes part of the sequences from *Ureaplasma*, or an immunologically functional equivalent thereof. Of course, the nucleic acid may comprise and/or encode additional sequences, including but not limited to those comprising one or more immunomodulators or adjuvants. The nucleotide and protein, polypeptide and peptide encoding sequences for various genes have been previously disclosed, and may be found at computerized databases known to those of ordinary skill in the art. One such database is the National Center for Biotechnology Information's GenBank® and GenPept databases. The coding regions for these known genes may be amplified, combined with the sequences encompassed in the invention (e.g., ligated) and/or expressed using the techniques disclosed herein or by any technique that would be know to those of ordinary skill in the art (e.g., Sambrook et al., 1987). Though a nucleic acid may be expressed in an in vitro expression system, in preferred embodiments the nucleic acid comprises a vector for in vivo replication and/or expression.

C. Cellular Vaccine Antigens

In another embodiment, a cell expressing the antigen may comprise the vaccine. The cell may be isolated from a culture, tissue, organ or organism and administered to an animal as a cellular vaccine. Thus, the present invention contemplates a "cellular vaccine." The cell may be transfected with a nucleic acid encoding an antigen to enhance its expression of the antigen. Of course, the cell may also express one or more additional vaccine components, such as immunomodulators or adjuvants. A vaccine may comprise all or part of the cell.

In particular embodiments, it is contemplated that nucleic acids encoding antigens of the present invention may be transfected into plants, particularly edible plants, and all or part of the plant material used to prepare a vaccine, such as for example, an oral vaccine. Such methods are described in U.S. Pat. Nos. 5,484,719, 5,612,487, 5,914,123, 5,977,438 and 6,034,298, each incorporated herein by reference.

D. Immunologically Functional Equivalents

As modifications and changes may be made in the structure of an antigenic composition of the present invention, and still obtain molecules having like or otherwise desirable characteristics, such immunologically functional equivalents are also encompassed within the present invention.

For example, certain amino acids may be substituted for other amino acids in a peptide, polypeptide or protein structure without appreciable loss of interactive binding capacity with structures such as, for example, antigen binding regions of antibodies, binding sites on substrate molecules or receptors, DNA binding sites, or such like. Since it is the interactive capacity and nature of a peptide, polypeptide or protein that defines its biological (e.g., immunological) functional activity, certain amino acid sequence substitutions can be made in a amino acid sequence (or, of course, its underlying DNA coding sequence) and nevertheless obtain a peptide or polypeptide with like (agonistic) properties. It is thus contemplated by the inventors that various changes may be made in the sequence of an antigenic composition such as, for example a peptide or polypeptide, or underlying DNA, without appreciable loss of biological utility or activity.

As used herein, an "amino molecule" refers to any amino acid, amino acid derivative or amino acid mimic as would be known to one of ordinary skill in the art. In certain embodiments, the residues of the antigenic composition comprises amino molecules that are sequential, without any non-amino molecule interrupting the sequence of amino molecule residues. In other embodiments, the sequence may comprise one or more non-amino molecule moieties. In particular embodiments, the sequence of residues of the antigenic composition may be interrupted by one or more non-amino molecule moieties.

Accordingly, antigenic composition, particularly an immunologically functional equivalent of the sequences disclosed herein, may encompass an amino molecule sequence comprising at least one of the 20 common amino acids in naturally synthesized proteins, or at least one modified or unusual amino acid.

In term of immunologically functional equivalent, it is well understood by the skilled artisan that, inherent in the definition is the concept that there is a limit to the number of changes that may be made within a defined portion of the molecule and still result in a molecule with an acceptable level of equivalent immunological activity. An immunologically functional equivalent peptide or polypeptide are thus defined herein as those peptide(s) or polypeptide(s) in which certain, not most or all, of the amino acid(s) may be substituted.

In particular, where a shorter length peptide is concerned, it is contemplated that fewer amino acid substitutions should be made within the given peptide. A longer polypeptide may have an intermediate number of changes. The full length protein will have the most tolerance for a larger number of changes. Of course, a plurality of distinct polypeptides/peptides with different substitutions may easily be made and used in accordance with the invention.

It also is well understood that where certain residues are shown to be particularly important to the immunological or structural properties of a protein or peptide, e.g., residues in binding regions or active sites, such residues may not generally be exchanged. This is an important consideration in the present invention, where changes in the antigenic site should be carefully considered and subsequently tested to ensure maintenance of immunological function (e.g., antigenicity), where maintenance of immunological function is desired. In this manner, functional equivalents are defined herein as those peptides or polypeptides which maintain a substantial amount of their native immunological activity.

Amino acid substitutions are generally based on the relative similarity of the amino acid side chain substituents, for example, their hydrophobicity, hydrophilicity, charge, size, and the like. An analysis of the size, shape and type of the amino acid side chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as immunologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (0.4); threonine (0.7); serine (0.8); tryptophan (0.9); tyrosine (1.3); proline (1.6); histidine (3.2); glutamate (3.5); glutamine (3.5); aspartate (3.5); asparagine (3.5); lysine (3.9); and arginine (4.5).

The importance of the hydropathic amino acid index in conferring interactive biological function on a protein, polypeptide or peptide is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It also is understood in the art that the substitution of like amino acids can be made effectively on the basis of hydrophilicity, particularly where the immunological functional equivalent polypeptide or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a immunological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (0.4); proline (0.5±1); alanine (0.5); histidine (0.5); cysteine (1.0); methionine (1.3); valine (1.5); leucine (1.8); isoleucine (1.8); tyrosine (2.3); phenyl alanine (2.5); tryptophan (3.4).

In making changes based upon similar hydrophilicity values, the substitution of amino acids whose hydrophilicity values are within ±2 is preferred, those which are within ±1 are particularly preferred, and those within ±0.5 are even more particularly preferred.

Numerous scientific publications have also been devoted to the prediction of secondary structure, and to the identification of an epitope, from analyses of an amino acid sequence (Chou & Fasman, 1974a,b; 1978a,b, 1979). Any of these may be used, if desired, to supplement the teachings of U.S. Pat. No. 4,554,101.

Moreover, computer programs are currently available to assist with predicting an antigenic portion and an epitopic core region of one or more proteins, polypeptides or peptides. Examples include those programs based upon the Jameson Wolf analysis (Jameson & Wolf, 1988; Wolf et al., 1988), the program PepPlot® (Brutlag et al., 1990; Weinberger et al., 1985), and other new programs for protein tertiary structure prediction (Fetrow & Bryant, 1993). Another commercially available software program capable of carrying out such analyses is MacVector (IBI, New Haven, Conn.).

In further embodiments, major antigenic determinants of a peptide or polypeptide may be identified by an empirical approach in which portions of a nucleic acid encoding a peptide or polypeptide are expressed in a recombinant host, and the resulting peptide(s) or polypeptide(s) tested for their ability to elicit an immune response. For example, PC™ can be used to prepare a range of peptides or polypeptides lacking successively longer fragments of the C terminus of the amino acid sequence. The immunoactivity of each of these peptides or polypeptides is determined to identify those fragments or domains that are immunodominant. Further studies in which only a small number of amino acids are removed at each iteration then allows the location of the antigenic determinant(s) of the peptide or polypeptide to be more precisely determined.

Another method for determining a major antigenic determinant of a peptide or polypeptide is the SPOTs system (Genosys Biotechnologies, Inc., The Woodlands, Tex.). In this method, overlapping peptides are synthesized on a cellulose membrane, which following synthesis and deprotection, is screened using a polyclonal or monoclonal antibody. An antigenic determinant of the peptides or polypeptides which are initially identified can be further localized by performing subsequent syntheses of smaller peptides with larger overlaps, and by eventually replacing individual amino acids at each position along the immunoreactive sequence.

Once one or more such analyses are completed, an antigenic composition, such as for example a peptide or a polypeptide is prepared that contain at least the essential features of one or more antigenic determinants. An antigenic composition is then employed in the generation of antisera against the composition, and preferably the antigenic determinant(s).

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. Nucleic acids encoding these antigenic compositions also can be constructed and inserted into one or more expression vectors by standard methods (Sambrook et al., 1987), for example, using PCR cloning methodology.

In addition to the peptidyl compounds described herein, the inventors also contemplate that other sterically similar compounds may be formulated to mimic the key portions of the peptide or polypeptide structure or to interact specifically with, for example, an antibody. Such compounds, which may be termed peptidomimetics, may be used in the same manner as a peptide or polypeptide of the invention and hence are also immunologically functional equivalents.

Certain mimetics that mimic elements of protein secondary structure are described in Johnson et al. (1993). The underlying rationale behind the use of peptide mimetics is that the peptide backbone of proteins exists chiefly to orientate amino acid side chains in such a way as to facilitate molecular interactions, such as those of antibody and antigen. A peptide mimetic is thus designed to permit molecular interactions similar to the natural molecule.

E. Antigen Mutagenesis

In particular embodiments, an antigenic composition is mutated for purposes such as, for example, enhancing its immunogenicity or producing or identifying a immunologically functional equivalent sequence. Methods of mutagenesis are well known to those of skill in the art (Sambrook et al., 1987). As used herein, the term "oligonucleotide directed mutagenesis procedure" refers to template dependent processes and vector mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template dependent extension of a primer molecule. The term template dependent process refers to nucleic acid synthesis of an RNA or a DNA molecule wherein the sequence of the newly synthesized strand of nucleic acid is dictated by the well known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In a preferred embodiment, site directed mutagenesis is used. Site specific mutagenesis is a technique useful in the preparation of an antigenic composition (e.g., a composition comprising peptide or polypeptide, or immunologically functional equivalent protein, polypeptide or peptide), through specific mutagenesis of the underlying DNA. In general, the technique of site specific mutagenesis is well known in the art. The technique further provides a ready ability to prepare and test sequence variants, incorporating one or more of the foregoing considerations, by introducing one or more nucleotide sequence changes into the DNA. Site specific mutagenesis allows the production of a mutant through the use of specific oligonucleotide sequence(s) which encode the DNA sequence of the desired mutation, as well as a sufficient number of adjacent nucleotides, to provide a primer sequence of sufficient size and sequence complexity to form a stable duplex on both sides of the position being mutated. Typically, a primer of about 17 to about 75 nucleotides in length is preferred, with about 10 to about 25 or more residues on both sides of the position being altered, while primers of about 17 to about 25 nucleotides in length being more preferred, with about 5 to 10 residues on both sides of the position being altered.

In general, site directed mutagenesis is performed by first obtaining a single stranded vector, or melting of two strands of a double stranded vector which includes within its sequence a DNA sequence encoding the desired protein. As will be appreciated by one of ordinary skill in the art, the technique typically employs a bacteriophage vector that exists in both a single stranded and double stranded form. Typical vectors useful in site directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

This mutagenic primer is then annealed with the single stranded DNA preparation, and subjected to DNA polymerizing enzymes such as, for example, E. coli polymerase I Klenow fragment, in order to complete the synthesis of the mutation bearing strand. Thus, a heteroduplex is formed wherein one strand encodes the original non mutated sequence and the second strand bears the desired mutation. This heteroduplex vector is then used to transform appropriate cells, such as E. coli cells, and clones are selected that include recombinant vectors bearing the mutated sequence arrangement.

Alternatively, a pair of primers may be annealed to two separate strands of a double stranded vector to simultaneously synthesize both corresponding complementary strands with the desired mutation(s) in a PCR™ reaction. A genetic selection scheme to enrich for clones incorporating the mutagenic oligonucleotide has been devised (Kunkel et al., 1987). Alternatively, the use of PCR with commercially available thermostable enzymes such as Taq polymerase may be used to incorporate a mutagenic oligonucleotide primer into an amplified DNA fragment that can then be cloned into an appropriate cloning or expression vector (Tomic et al., 1990; Upender et al., 1995). A PCR employing a thermostable ligase in addition to a thermostable polymerase also may be used to incorporate a phosphorylated mutagenic oligonucleotide into an amplified DNA fragment that may then be cloned into an appropriate cloning or expression vector (Michael 1994).

The preparation of sequence variants of the selected gene using site directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

Additionally, one particularly useful mutagenesis technique is alanine scanning mutagenesis in which a number of residues are substituted individually with the amino acid alanine so that the effects of losing side chain interactions can be determined, while minimizing the risk of large scale perturbations in protein conformation (Cunningham et al., 1989).

F. Vectors

In some embodiments of the invention, an immunological composition comprising a nucleic acid vector is employed.

In order to effect replication, expression or mutagenesis of a nucleic acid, the nucleic acid may be delivered ("transfected") into a cell. The tranfection of cells may be used, in certain embodiments, to recombinately produce one or more vaccine components for subsequent purification and preparation into a pharmaceutical vaccine. In other embodiments, the nucleic acid may be comprised as a genetic vaccine that is administered to an animal. In other embodiments, the nucleic acid is transfected into a cell and the cell administered to an animal as a cellular vaccine component. The nucleic acid may consist only of naked recombinant DNA, or may comprise, for example, additional materials to protect the nucleic acid and/or aid its targeting to specific cell types.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell.

The nucleic acid encoding the antigenic composition or other vaccine component may be stably integrated into the genome of the cell, or may be stably maintained in the cell as a separate, episomal segment of DNA. Such nucleic acid segments or "episomes" encode sequences sufficient to permit maintenance and replication independent of or in synchronization with the host cell cycle. Vectors and expression vectors may contain nucleic acid sequences that serve other functions as well and are described infra. How the expression construct is delivered to a cell and where in the cell the nucleic acid remains is dependent on the type of expression construct employed.

1. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base, EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art. Nonlimiting examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), and human platelet endothelial cell adhesion molecule-1 (Almendro et al., 1996).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with □ galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

10. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Vaccine components of the present invention may be a viral vector that encode one or more antigenic compositions or other components such as, for example, an immunomodulator or adjuvant. Non-limiting examples of virus vectors that may be used to deliver a nucleic acid of the present invention are described below.

11. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

12. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the [INVENTION] vaccines of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

13. Retroviral Vectors

Retroviruses have promise as antigen delivery vectors in vaccines due to their ability to integrate their genes into the host genome, transferring a large amount of foreign genetic material, infecting a broad spectrum of species and cell types and of being packaged in special cell lines (Miller, 1992).

In order to construct a vaccine retroviral vector, a nucleic acid (e.g., one encoding an antigen of interest) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

14. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

G. Vaccine Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989). Thus, it is contemplated that antibodies, specific binding ligands and/or other targeting moieties may be used to specifically transfect APC types.

H. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985), and any combination of such methods. Through the application of techniques such as these, organelle(s), cell(s), tissue(s) or organism(s) may be stably or transiently transformed.

1. Injection

In certain embodiments, a nucleic acid may be delivered to an organelle, a cell, a tissue or an organism via one or more injections (i.e., a needle injection). Methods of injection of nucleic acids are described herein, and are well known to those of ordinary skill in the art. Further embodiments of the present invention include the introduction of a nucleic acid by direct microinjection to a cell. Direct microinjection has been used to introduce nucleic acid constructs into *Xenopus* oocytes (Harland and Weintraub, 1985). The amount of composition used may vary upon the nature of the antigen as well as the organelle, cell, tissue or organism used 2. Electroporation In certain embodiments of the present invention, a nucleic acid is introduced into an organelle, a cell, a tissue or an organism via electroporation. Electroporation involves the exposure of a suspension of cells and DNA to a high voltage electric discharge. In some variants of this method, certain cell wall degrading enzymes, such as pectin degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre B lymphocytes have been transfected with human kappa immunoglobulin genes (Potter et al., 1984), and rat hepatocytes have been transfected with the chloramphenicol acetyltransferase gene (Tur Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin degrading enzymes (pectolyases) or mechanically wounding in a controlled manner Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

3. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L (A9), mouse C127, CHO, CV 1, BHK, NIH3T3 and HeLa cells were transfected with a neomycin marker gene (Chen and Okayama, 1987), and rat hepatocytes were transfected with a variety of marker genes (Rippe et al., 1990).

4. DEAE Dextran

In another embodiment, a nucleic acid is delivered into a cell using DEAE dextran followed by polyethylene glycol. In this manner, reporter plasmids were introduced into mouse myeloma and erythroleukemia cells (Gopal, 1985).

5. Sonication Loading

Additional embodiments of the present invention include the introduction of a nucleic acid by direct sonic loading. LTK fibroblasts have been transfected with the thymidine kinase gene by sonication loading (Fechheimer et al., 1987).

I. Liposome Mediated Transfection

In a further embodiment of the invention, one or more vaccine components or nucleic acids may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome mediated nucleic acid delivery and expression of foreign DNA in vitro has been very successful (Nicolau and Sene, 1982; Fraley et al., 1979; Nicolau et al., 1987). The feasibility of liposome mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome encapsulated DNA (Kaneda et al., 1989). In other embodiments, a liposome may be complexed or employed in conjunction with nuclear non histone chromosomal proteins (HMG 1) (Kato et al., 1991). In yet further embodiments, a liposome may be complexed or employed in conjunction with both HVJ and HMG 1. In other embodiments, a delivery vehicle may comprise a ligand and a liposome.

J. Receptor Mediated Transfection

One or more vaccine components or nucleic acids, may be employed to delivered using a receptor mediated delivery vehicle. These take advantage of the selective uptake of macromolecules by receptor mediated endocytosis that will be occurring in the target cells. In view of the cell type specific distribution of various receptors, this delivery method adds another degree of specificity to the present invention. Specific delivery in the context of another mammalian cell type has been described (Wu and Wu, 1993, incorporated herein by reference).

Certain receptor mediated gene targeting vehicles comprise a cell receptor specific ligand and a nucleic acid binding agent. Others comprise a cell receptor specific ligand to which the nucleic acid to be delivered has been operatively attached. Several ligands have been used for receptor mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell specific binding. For example, lactosyl ceramide, a galactose terminal asialganglioside, have been incorporated into liposomes and observed an increase in the uptake of the insulin gene by hepatocytes (Nicolau et al., 1987). It is contemplated that the tissue specific transforming constructs of the present invention can be specifically delivered into a target cell in a similar manner.

K. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA coated microprojectiles to a high velocity allowing them to pierce cell membranes and enter cells without killing them (Klein et al., 1987). There are a wide variety of microprojectile bombardment techniques known in the art, many of which are applicable to the invention.

In microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

L. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co expressed with other selected RNAs or proteinaceous sequences in the same host cell. Co expression may be achieved by co transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed with a composition of the invention. The tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, or testes.

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art.

Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F, lambda, prototrophic, ATCC No. 273325), DH5α, JM109, and KC8, bacilli such as *Bacillus subtilis*; and other enterobacteriaceae such as *Salmonella typhimurium, Serratia marcescens*, various *Pseudomonas* specie, as well as a number of commercially available bacterial hosts such as SURE® Competent Cells and SOLOPACK Gold Cells (STRATAGENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

M. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed", i.e., expressed in increased levels relative to its natural expression in cells. Such overexpression may be assessed by a variety of methods, including radio labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g. 8M) or chaotropic agents such as guanidine hydrochloride in the presence of reducing agents, such as beta-mercaptoethanol or DTT (dithiothreitol), and refolded into a more desirable conformation, as would be known to one of ordinary skill in the art.

N. Vaccine Component Purification

In any case, a vaccine component (e.g., an antigenic peptide or polypeptide or nucleic acid encoding a proteinaceous composition) may be isolated and/or purified from the chemical synthesis reagents, cell or cellular components. In a method of producing the vaccine component, purification is accomplished by any appropriate technique that is described herein or well known to those of skill in the art (e.g., Sambrook et al., 1987). Although preferred for use in certain embodiments, there is no general requirement that an antigenic composition of the present invention or other vaccine component always be provided in their most purified state. Indeed, it is contemplated that less substantially purified vaccine component, which is nonetheless enriched in the desired compound, relative to the natural state, will have utility in certain embodiments, such as, for example, total recovery of protein product, or in maintaining the activity of an expressed protein. However, it is contemplate that inactive products also have utility in certain embodiments, such as, e.g., in determining antigenicity via antibody generation.

The present invention also provides purified, and in preferred embodiments, substantially purified vaccines or vaccine components. The term "purified vaccine component" as used herein, is intended to refer to at least one vaccine component (e.g., a proteinaceous composition, isolatable from cells), wherein the component is purified to any degree relative to its naturally obtainable state, e.g., relative to its purity within a cellular extract or reagents of chemical synthesis. In certain aspects wherein the vaccine component is a proteinaceous composition, a purified vaccine component also refers to a wild type or mutant protein, polypeptide, or peptide free from the environment in which it naturally occurs.

Where the term "substantially purified" is used, this will refer to a composition in which the specific compound (e.g., a protein, polypeptide, or peptide) forms the major component of the composition, such as constituting about 50% of the compounds in the composition or more. In preferred embodiments, a substantially purified vaccine component will constitute more than about 60%, about 70%, about 80%, about 90%, about 95%, about 99% or even more of the compounds in the composition.

In certain embodiments, a vaccine component may be purified to homogeneity. As applied to the present invention, "purified to homogeneity," means that the vaccine component has a level of purity where the compound is substantially free from other chemicals, biomolecules or cells. For example, a purified peptide, polypeptide or protein will often be sufficiently free of other protein components so that degradative sequencing may be performed successfully. Various methods for quantifying the degree of purification of a vaccine component will be known to those of skill in the art in light of the present disclosure. These include, for example, determining the specific protein activity of a fraction (e.g., antigenicity), or assessing the number of polypeptides within a fraction by gel electrophoresis.

Various techniques suitable for use in chemical, biomolecule or biological purification, well known to those of skill in the art, may be applicable to preparation of a vaccine component of the present invention. These include, for example, precipitation with ammonium sulfate, PEG, antibodies and the like or by heat denaturation, followed by centrifugation; fractionation, chromatographic procedures, including but not limited to, partition chromatograph (e.g., paper chromatograph, thin-layer chromatograph (TLC), gas-liquid chromatography and gel chromatography) gas chromatography, high performance liquid chromatography, affinity chromatography, supercritical flow chromatography ion exchange, gel filtration, reverse phase, hydroxylapatite, lectin affinity; isoelectric focusing and gel electrophoresis (see for example, Sambrook et al. 1989; and Freifelder, Physical Biochemistry, Second Edition, pages 238 246, incorporated herein by reference).

Given many DNA and proteins are known (see for example, the National Center for Biotechnology Information's GenBank® and GenPept databases), or may be identified and amplified using the methods described herein, any purification method for recombinately expressed nucleic acid or proteinaceous sequences known to those of skill in the art can now be employed. In certain aspects, a nucleic acid may be purified on polyacrylamide gels, and/or cesium chloride centrifugation gradients, or by any other means known to one of ordinary skill in the art (see for example, Sambrook et al. 1989, incorporated herein by reference). In further aspects, a purification of a proteinaceous sequence may be conducted by recombinately expressing the sequence as a fusion protein. Such purification methods are routine in the art. This is exemplified by the generation of an specific protein glutathione S transferase fusion protein, expression in *E. coli*, and isolation to homogeneity using affinity chromatography on glutathione agarose or the generation of a polyhistidine tag on the N or C terminus of the protein, and subsequent purification using Ni affinity chromatography. In particular aspects, cells or other components of the vaccine may be purified by flow cytometry. Flow cytometry involves the separation of cells or other particles in a liquid sample, and is well known in the art (see, for example, U.S. Pat. Nos. 3,826,364, 4,284,412, 4,989,977, 4,498,766, 5,478,722, 4,857,451, 4,774,189, 4,767,206, 4,714,682, 5,160,974 and 4,661,913). Any of these techniques described herein, and combinations of these and any other techniques known to skilled artisans, may be used to purify and/or assay the purity of the various chemicals, proteinaceous compounds, nucleic acids, cellular materials and/or cells that may comprise a vaccine of the present invention. As is generally known in the art, it is believed that the order of conducting the various purification steps may be changed, or that certain steps may be omitted, and still result in a suitable method for the preparation of a substantially purified antigen or other vaccine component.

O. Additional Vaccine Components

It is contemplated that an antigenic composition of the invention may be combined with one or more additional components to form a more effective vaccine. Non-limiting examples of additional components include, for example, one or more additional antigens, immunomodulators or adjuvants to stimulate an immune response to an antigenic composition of the present invention and/or the additional component(s).

1. Immunomodulators

For example, it is contemplated that immunomodulators can be included in the vaccine to augment a cell's or a patient's (e.g., an animal's) response Immunomodulators can be included as purified proteins, nucleic acids encoding immunomodulators, and/or cells that express immunomodulators in the vaccine composition. The following sections list non-limiting examples of immunomodulators that are of interest, and it is contemplated that various combinations of immunomodulators may be used in certain embodiments (e.g., a cytokine and a chemokine).

2. Cytokines

Interleukins, cytokines, nucleic acids encoding interleukins or cytokines, and/or cells expressing such compounds are contemplated as possible vaccine components. Interleukins and cytokines, include but are not limited to interleukin 1 (IL-1), IL-2, IL-3, IL-4, IL-5, IL-6, IL-7, IL-8, IL-9, IL-10, IL-11, IL-12, IL-13, IL-14, IL-15, IL-18, □-interferon, □-interferon, □-interferon, angiostatin, thrombospondin, endostatin, GM-CSF, G-CSF, M-CSF, METH 1, METH 2, tumor necrosis factor, TGF□, LT and combinations thereof.

3. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-alpha, MIP1-Beta, IP-10 and combinations thereof. The skilled artisan will recognize that certain cytokines are also known to have chemoattractant effects and could also be classified under the term chemokines.

4. Immunogenic Carrier Proteins

In certain embodiments, an antigenic composition may be chemically coupled to a carrier or recombinantly expressed with a immunogenic carrier peptide or polypetide (e.g., a antigen-carrier fusion peptide or polypeptide) to enhance an immune reaction. Exemplary and preferred immunogenic carrier amino acid sequences include hepatitis B surface antigen, keyhole limpet hemocyanin (KLH) and bovine serum albumin (BSA). Other albumins such as ovalbumin, mouse serum albumin or rabbit serum albumin also can be used as immunogenic carrier proteins. Means for conjugating a polypeptide or peptide to a immunogenic carrier protein are well known in the art and include, for example, glutaraldehyde, m maleimidobenzoyl N hydroxysuccinimide ester, carbodiimide and bis biazotized benzidine.

5. Biological Response Modifiers

It may be desirable to coadminister biologic response modifiers (BRM), which have been shown to upregulate T cell immunity or downregulate suppressor cell activity. Such BRMs include, but are not limited to, cimetidine (CIM; 1200 mg/d) (Smith/Kline, PA); low dose cyclophosphamide (CYP; 300 mg/m2) (Johnson/Mead, NJ), or a gene encoding a protein involved in one or more immune helper functions, such as B 7.

6. Adjuvants

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

In one aspect, an adjuvant effect is achieved by use of an agent, such as alum, used in about 0.05 to about 0.1% solution in phosphate buffered saline. Alternatively, the antigen is made as an admixture with synthetic polymers of sugars (Carbopol®) used as an about 0.25% solution. Adjuvant effect may also be made my aggregation of the antigen in the vaccine by heat treatment with temperatures ranging between about 70° to about 101° C. for a 30 second to 2 minute period, respectively. Aggregation by reactivating with pepsin treated (Fab) antibodies to albumin, mixture with bacterial cell(s) such as *C. parvum*, an endotoxin or a lipopolysaccharide component of Gram negative bacteria, emulsion in physiologically acceptable oil vehicles, such as mannide mono oleate (Aracel A), or emulsion with a 20% solution of a perfluorocarbon (Fluosol DA®) used as a block substitute, also may be employed.

Some adjuvants, for example, certain organic molecules obtained from bacteria, act on the host rather than on the antigen. An example is muramyl dipeptide (N acetylmuramyl L alanyl D isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen specific. If they are administered together with a purified antigen, however, they can be used to selectively promote the response to the antigen.

Adjuvants have been used experimentally to promote a generalized increase in immunity against unknown antigens (e.g., U.S. Pat. No. 4,877,611).

In certain embodiments, hemocyanins and hemoerythrins may also be used in the invention. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin.

Another group of adjuvants are the muramyl dipeptide (MDP, N acetylmuramyl L alanyl D isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is the to be effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present invention.

Another adjuvant contemplated for use in the present invention is BCG. BCG (*bacillus* Calmette-Guerin, an attenuated strain of *Mycobacterium*) and BCG cell wall skeleton (CWS) may also be used as adjuvants in the invention, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945.

BCG is an important clinical tool because of its immunostimulatory properties. BCG acts to stimulate the reticuloendothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990).

Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE BCG (Organon Inc., West Orange, N.J.).

In a typical practice of the present invention, cells of *Mycobacterium bovis*-BCG are grown and harvested by methods known in the art. For example, they may be grown as a surface pellicle on a Sauton medium or in a fermentation vessel containing the dispersed culture in a Dubos medium (Dubos et al., 1947; Rosenthal, 1937). All the cultures are harvested after 14 days incubation at about 37° C. Cells grown as a pellicle are harvested by using a platinum loop whereas those from the fermenter are harvested by centrifugation or tangential-flow filtration. The harvested cells are resuspended in an aqueous sterile buffer medium. A typical suspension contains from about $2 \times 10^{10}$ cells/ml to about $2 \times 10^{12}$ cells/ml. To this bacterial suspension, a sterile solution containing a selected enzyme which will degrade the BCG cell covering material is added. The resultant suspension is agitated such as by stirring to ensure maximal dispersal of the BCG organisms. Thereafter, a more concentrated cell suspension is prepared and the enzyme in the concentrate removed, typically by washing with an aqueous buffer, employing known techniques such as tangential-flow filtration. The enzyme-free cells are adjusted to an optimal immunological concentration with a cryoprotectant solution, after which they are filled into vials, ampoules, etc., and lyophilized, yielding BCG vaccine, which upon reconstitution with water is ready for immunization.

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994; Hunter et al., 1991) may also be employed. Oligonucleotides are another useful group of adjuvants (Yamamoto et al., 1988). Quil A and lentinen are other adjuvants that may be used in certain embodiments of the present invention.

One group of adjuvants preferred for use in the invention are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

In other embodiments, the present invention contemplates that a variety of adjuvants may be employed in the membranes of cells, resulting in an improved immunogenic composition. The only requirement is, generally, that the adjuvant be capable of incorporation into, physical association with, or conjugation to, the cell membrane of the cell in question. Those of skill in the art will know the different kinds of adjuvants that can be conjugated to cellular vaccines in accordance with this invention and these include alkyl lysophosphilipids (ALP); BCG; and biotin (including biotinylated derivatives) among others. Certain adjuvants particularly contemplated for use are the teichoic acids from Gram cells. These include the lipoteichoic acids (LTA), ribitol teichoic acids (RTA) and glycerol teichoic acid (GTA). Active forms of their synthetic counterparts may also be employed in connection with the invention (Takada et al., 1995a).

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non irradiated tumor cells, is irrelevant in such circumstances.

One group of adjuvants preferred for use in some embodiments of the present invention are those that can be encoded by a nucleic acid (e.g., DNA or RNA). It is contemplated that such adjuvants may be encoded in a nucleic acid (e.g., an expression vector) encoding the antigen, or in a separate vector or other construct. These nucleic acids encoding the adjuvants can be delivered directly, such as for example with lipids or liposomes.

7. Excipients, Salts and Auxilary Substances

An antigenic composition of the present invention may be mixed with one or more additional components (e.g., excipients, salts, etc.) which are pharmaceutically acceptable and compatible with at least one active ingredient (e.g., antigen). Suitable excipients are, for example, water, saline, dextrose, glycerol, ethanol and combinations thereof.

An antigenic composition of the present invention may be formulated into the vaccine as a neutral or salt form. A pharmaceutically acceptable salt, includes the acid addition salts (formed with the free amino groups of the peptide) and those which are formed with inorganic acids such as, for example, hydrochloric or phosphoric acid, or such organic acids as acetic, oxalic, tartaric, mandelic, and the like. A salt formed with a free carboxyl group also may be derived from an inorganic base such as, for example, sodium, potassium, ammonium, calcium, or ferric hydroxide, and such organic bases as isopropylamine, trimethylamine, 2 ethylamino ethanol, histidine, procaine, and combinations thereof.

In addition, if desired, an antigenic composition may comprise minor amounts of one or more auxiliary substances such as for example wetting or emulsifying agents, pH buffering agents, etc. which enhance the effectiveness of the antigenic composition or vaccine.

P. Vaccine Preparations

Once produced, synthesized and/or purified, an antigen or other vaccine component may be prepared as a vaccine for administration to a patient. The preparation of a vaccine is generally well understood in the art, as exemplified by U.S. Pat. Nos. 4,608,251, 4,601,903, 4,599,231, 4,599,230, and 4,596,792, all incorporated herein by reference. Such methods may be used to prepare a vaccine comprising an antigenic composition comprising one or more antigens of *Ureaplasma* as active ingredient(s), in light of the present disclosure. In preferred embodiments, the compositions of the present invention are prepared to be pharmacologically acceptable vaccines.

Pharmaceutical vaccine compositions of the present invention comprise an effective amount of one or more *Ureaplasma* antigens or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one *Ureaplasma* antigen or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The *Ureaplasma* vaccine may comprise different types of carriers depending on whether it is to be administered in solid, liquid or aerosol form, and whether it need to be sterile for such routes of administration as injection. Except insofar as any conventional carrier is incompatible with the active ingredient, its use in the therapeutic or pharmaceutical compositions is contemplated.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The *Ureaplasma* vaccine may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the *Ureaplasma* vaccine is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

V. Exemplary Vaccine Administration

The manner of administration of a vaccine may be varied widely. Any of the conventional methods for administration of a vaccine are applicable. For example, a vaccine may be conventionally administered intravenously, intradermally, intraarterially, intraperitoneally, intralesionally, intracranially, intraarticularly, intraprostaticaly, intrapleurally, intratracheally, intranasally, intravitreally, intravaginally, intratumorally, intramuscularly, intraperitoneally, subcutaneously, intravesicularlly, mucosally, intrapericardially, orally, rectally, nasally, topically, in eye drops, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

A vaccination schedule and dosages may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

A vaccine is administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g., the capacity of the individual's immune system to synthesize antibodies, and the degree of protection desired. The dosage of the vaccine will depend on the route of administration and will vary according to the size of the host. Precise amounts of an active ingredient required to be administered depend on the judgment of the practitioner. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., innoculations) are also variable, but are typified by an initial administration followed by subsequent inoculation(s) or other administration(s).

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 15 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed and assays of protection from challenge with the *Ureaplasma* vaccine can be performed, following immunization.

A. Enhancement of an Immune Response

The present invention includes a method of enhancing the immune response in a subject comprising the steps of contacting one or more lymphocytes with an *Ureaplasma* antigenic composition. In certain embodiments the one or more lymphocytes is comprised in an animal, such as a human. In other embodiments, the lymphocyte(s) may be isolated from an animal or from a tissue (e.g., blood) of the animal. In certain preferred embodiments, the lymphocyte(s) are peripheral blood lymphocyte(s). In certain embodiments, the one or more lymphocytes comprise a T-lymphocyte or a B-lymphocyte. In a particularly preferred facet, the T-lymphocyte is a cytotoxic T-lymphocyte.

The enhanced immune response may be an active or a passive immune response. Alternatively, the response may be part of an adoptive immunotherapy approach in which lymphocyte(s) are obtained with from an animal (e.g., a patient), then pulsed with composition comprising an antigenic composition. In a preferred embodiment, the lymphocyte(s) may be administered to the same or different animal (e.g., same or different donors).

B. Cytotoxic T Lymphocytes

In certain embodiments, T-lymphocytes are specifically activated by contact with an antigenic composition of the present invention. In certain embodiments, T-lymphocytes are activated by contact with an antigen presenting cell that is or has been in contact with an antigenic composition of the invention.

T cells express a unique antigen binding receptor on their membrane (T cell receptor), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secret various lymphokines, that are crucial for the activation of B cells, T cytotoxic cells, macrophages and other cells of the immune system. In contrast, a T cytotoxic cells that recognizes an antigen MHC complex proliferates and differentiates into an effector cell called a cytotoxic T lymphocyte (CTL). CTLs eliminate cells of the body displaying antigen by producing substances that result in cell lysis.

CTL activity can be assessed by methods described herein or as would be known to one of skill in the art. For example, CTLs may be assessed in freshly isolated peripheral blood mononuclear cells (PBMC), in a phytohaemaglutinin stimulated IL 2 expanded cell line established from PBMC (Bernard et al., 1998) or by T cells isolated from a previously immunized subject and restimulated for 6 days with DC infected with an adenovirus vector containing antigen using standard 4 h $^{51}$Cr release microtoxicity assays. In another fluorometric assay developed for detecting cell mediated cytotoxicity, the fluorophore used is the non toxic molecule alamarBlue (Nociari et al., 1998). The alamarBlue is fluorescently quenched (i.e., low quantum yield) until mitochondrial reduction occurs, which then results in a dramatic increase in the alamarBlue fluorescence intensity (i.e., increase in the quantum yield). This assay is reported to be extremely sensitive, specific and requires a significantly lower number of effector cells than the standard $^{51}$Cr release assay.

In certain aspects, T helper cell responses can be measured by in vitro or in vivo assay with peptides, polypeptides or proteins. In vitro assays include measurement of a specific cytokine release by enzyme, radioisotope, chromaphore or fluorescent assays. In vivo assays include delayed type hypersensitivity responses called skin tests, as would be known to one of ordinary skill in the art.

C. Antigen Presenting Cells

In general, the term "antigen presenting cell" can be any cell that accomplishes the goal of the invention by aiding the enhancement of an immune response (i.e., from the T-cell or -B-cell arms of the immune system) against an antigen (e.g., a *Ureaplasma* antigen or a immunologically functional equivalent) or antigenic composition of the present invention. Such cells can be defined by those of skill in the art, using methods disclosed herein and in the art. As is understood by one of ordinary skill in the art (see for example Kuby, 1993, incorporated herein by reference), and used herein certain embodiments, a cell that displays or presents an antigen normally or preferentially with a class II major histocompatability molecule or complex to an immune cell is an "antigen presenting cell." In certain aspects, a cell (e.g., an APC cell) may be fused with another cell, such as a recombinant cell or a tumor cell that expresses the desired antigen. Methods for preparing a fusion of two or more cells is well known in the art, such as for example, the methods disclosed in Goding, pp. 65 66, 71-74 1986; Campbell, pp. 75 83, 1984; Kohler and Milstein, 1975; Kohler and Milstein, 1976; Gefter et al., 1977, each incorporated herein by reference. In some cases, the immune cell to which an antigen presenting cell displays or presents an antigen to is a CD4+TH cell. Additional molecules expressed on the APC or other immune cells may aid or improve the enhancement of an immune response. Secreted or soluble molecules, such as for example, immunomodulators and adjuvants, may also aid or enhance the immune response against an antigen. Such molecules are well known to one of skill in the art, and various examples are described herein.

D. Antibody Generation

In certain embodiments, isolated antibodies to the antigenic compositions of the present invention are contemplated as useful for purification, diagnostic and therapeutic applications. For example, it is contemplated that an antibody may be used as a vaccine component to bind a *Ureaplasma* antigen. As used herein, the term "antibody" is intended to refer broadly to any immunologic binding agent such as IgG, IgM, IgA, IgD and IgE. Generally, IgG or IgM are preferred because they are the most common antibodies in the physiological situation and because they are most easily made in a laboratory setting. The term "antibody" is used to refer to any antibody like molecule that has an antigen binding region, and includes antibody fragments such as Fab', Fab, F(ab')2, single domain antibodies (DABs), Fv, scFv (single chain Fv), and the like. The techniques for preparing and using various antibody based constructs and fragments are well known in the art. Means for preparing and characterizing an antibody are also well known in the art (See, e.g., Antibodies: A Laboratory Manual, Cold Spring Harbor Laboratory, 1988; and Antibody Engineering, Second Edition, Oxford University Press, 1995, each incorporated herein by reference).

In certain embodiment, one or more "humanized" antibodies are also contemplated, as are antibodies comprising components from various origins, such as for example, one or more chimeric antibodies from mouse, rat, or other species, bearing one or more human constant and/or variable region domains; one or more bispecific antibodies; or one or more recombinant and engineered antibodies and/or fragment(s) thereof. Methods for the development of one or more antibodies that are "custom tailored" to a patient's disease are likewise known and such custom tailored antibodies are also contemplated.

Monoclonal antibodies (MAbs) are recognized to have certain advantages, e.g., reproducibility and large scale production, and their use is generally preferred. MAbs may be readily prepared through use of well known techniques, such as those exemplified in U.S. Pat. No. 4,196,265, incorporated herein by reference.

In certain diagnostic or vaccine component purification aspects, an antibody one or more vaccine components, such as a *Ureaplasma* antigen, may be used. Non-limiting examples of such immunodetection methods include enzyme linked immunosorbant assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, 1999; Gulbis B and Galand P, 1993; De Jager R et al., 1993; and Nakamura et al., 1987, each incorporated herein by reference. Often, the antibody may be conjugated with an imaging agent to enhance detection of a vaccine component ligand bound to the antibody, as would be known to one of ordinary skill in the art. Many appropriate imaging agents are known in the art, as are methods for their attachment to antibodies (see, for e.g., U.S. Pat. Nos. 5,021,236; 4,938, 948; and 4,472,509, each incorporated herein by reference).

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939, 350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

VI. Proteins, Polypeptides, and Peptides

The present invention also provides purified, and in preferred embodiments, substantially purified, *Ureaplasma* proteins, polypeptides, or peptides. The term "purified proteins, polypeptides, or peptides" as used herein, is intended to refer to an proteinaceous composition, isolatable from mammalian cells or recombinant host cells, wherein the at least one protein, polypeptide, or peptide is purified to any degree relative to its naturally obtainable state, i.e., relative to its purity within a cellular extract. A purified protein, polypeptide, or peptide therefore also refers to a wild type or mutant protein, polypeptide, or peptide free from the environment in which it naturally occurs.

The nucleotide and protein, polypeptide and peptide sequences for various genes have been previously disclosed, and may be found at computerized databases known to those of ordinary skill in the art. One such database is the National Center for Biotechnology Information's GenBank® and GenPept databases. The coding regions for these known genes may be amplified and/or expressed using the techniques disclosed herein or by any technique that would be know to those of ordinary skill in the art. Additionally, peptide sequences may be synthesized by methods known to those of ordinary skill in the art, such as peptide synthesis using automated peptide synthesis machines, such as those available from Applied Biosystems (Foster City, Calif.).

Generally, "purified" will refer to a specific protein, polypeptide, or peptide composition that has been subjected to fractionation to remove various other proteins, polypeptides, or peptides, and which composition substantially retains its activity, as may be assessed, for example, by the protein assays, as described herein below, or as would be known to one of ordinary skill in the art for the desired protein, polypeptide or peptide.

Where the term "substantially purified" is used, this will refer to a composition in which the specific protein, polypeptide, or peptide forms the major component of the composition, such as constituting about 50% of the proteins in the composition or more. In preferred embodiments, a substantially purified protein will constitute more than 60%, 70%, 80%, 90%, 95%, 99% or even more of the proteins in the composition.

A peptide, polypeptide or protein that is "purified to homogeneity," as applied to the present invention, means that the peptide, polypeptide or protein has a level of purity where the peptide, polypeptide or protein is substantially free from other proteins and biological components. For example, a purified peptide, polypeptide or protein will often be sufficiently free of other protein components so that degradative sequencing may be performed successfully.

Various methods for quantifying the degree of purification of proteins, polypeptides, or peptides will be known to those of skill in the art in light of the present disclosure. These include, for example, determining the specific protein activity of a fraction, or assessing the number of polypeptides within a fraction by gel electrophoresis.

To purify a desired protein, polypeptide, or peptide a natural or recombinant composition comprising at least some specific proteins, polypeptides, or peptides will be subjected to fractionation to remove various other components from the composition. In addition to those techniques described in detail herein below, various other techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Another example is the purification of a specific fusion protein using a specific binding partner. Such purification methods are routine in the art. As the present invention provides DNA sequences for the specific proteins, any fusion protein purification method can now be practiced. This is exemplified by the generation of an specific protein glutathione S transferase fusion protein, expression in *E. coli*, and isolation to homogeneity using affinity chromatography on glutathione agarose or the generation of a polyhistidine tag on the N or C terminus of the protein, and subsequent purification using Ni affinity chromatography. However, given many DNA and proteins are known, or may be identified and amplified using the methods described herein, any purification method can now be employed.

Although preferred for use in certain embodiments, there is no general requirement that the protein, polypeptide, or peptide always be provided in their most purified state. Indeed, it is contemplated that less substantially purified protein, polypeptide or peptide, which are nonetheless enriched in the desired protein compositions, relative to the natural state, will have utility in certain embodiments.

Methods exhibiting a lower degree of relative purification may have advantages in total recovery of protein product, or in maintaining the activity of an expressed protein. Inactive products also have utility in certain embodiments, such as, e.g., in determining antigenicity via antibody generation.

VII. Pharmaceutical Preparations

Pharmaceutical compositions of the present invention comprise an effective amount of one or more vaccines of the invention or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one *Ureaplasma* vaccine or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The composition may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The composition may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semisolid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle composition that include the composition, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man) However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the composition may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the composition is formulated to be administered via an alimentary route Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, the composition may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneously, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

VIII. Detection of *Ureaplasma*

In some embodiments of the invention, compositions of the invention are utilized for detection of *Ureaplasma*. In specific cases, for example, anti-MBA monoclonal antibody is employed for detection of *Ureaplasma*. In specific embodiments, antibody against the MBA antigen (for example, the conserved portion or 5' end of the MBA antigen) is utilized to identify the organism as being present in culture, serum and/or other body fluids. In certain aspects, antibody against part of SEQ ID NO:4 is employed, for example.

Upon detection of *Ureaplasma* in a culture or in an individual, the respective culture or individual may be treated with one or more therapeutic compositions of the invention and/or other therapeutic means, including antibiotics, for example.

The skilled artisan recognizes that there are routine methods in the art for obtaining a sample to assay for detection of *Ureaplasma*.

IX. Exemplary Kits of the Invention

Any of the compositions described herein may be comprised in a kit. In a non-limiting example, a *Ureaplasma* immunogenic composition may be comprised in a kit, including a vaccine, for example a DNA vaccine.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the composition and any other reagent containers in close confinement for commercial sale. Such containers may include injection or blow molded plastic containers into which the desired vials are retained.

Therapeutic kits of the present invention include kits comprising a chemical compound or pharmaceutically acceptable salts thereof or a protein, polypeptide, peptide, inhibitor, gene, vector and/or other immunological effector. Such kits may generally contain, in suitable container means, a pharmaceutically acceptable formulation of a multiple banded antigen chemical compound or pharmaceutically acceptable salts thereof or protein, polypeptide, peptide, domain, inhibitor, and/or a gene and/or vector expressing any of the foregoing in a pharmaceutically acceptable formulation. The kit may have a single container means, and/or it may have distinct container means for each compound.

When the components of the kit are provided in one and/or more liquid solutions, the liquid solution is an aqueous solution, with a sterile aqueous solution being particularly preferred. The compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Perinatal Ureaplasma Infection and Brain Development

Utilizing a published murine model for chorioamnionitis, e13.5 day fetuses are infected with 5000 ccu of Ureaplasma or saline by direct infection. At e17.5 days, Ureaplasma's impact is evaluated between the groups on placental histopathology, blood, amniotic fluid, placenta Ureaplasma culture and PCR, and inflammatory mediators. There is also evaluation for evidence for Ureaplasma brain infection an inflammation on day e17.5, 6, and 18 wks after delivering including brain: Ureaplasma culture and PCR; inflammatory mediators; histopathology and histochemistry. Placenta histopathology is read by an expert in placenta pathology in a blinded fashion. One then evaluates pups born to mothers with Ureaplasma induced chorioamnionitis vs. pups exposed to saline in-utero for development of a neurologic or developmental phenotype during the 18 week observation. One employs standardized neurologic and developmental examinations by individuals blinded to the group. In this same chorioamnionitis model, one can determine the impact of a prenatal rDNA Ureaplasma vaccine on development of brain inflammation, and neurologic and developmental phenotypes by individuals blinded to the treatment group assignment (rDNA Ureaplasma or saline vaccine).

Example 2

Development of a Ureaplasma DNA Vaccine for the Treatment of Mammalian Infection Methods and Exemplary Data: The inventors have developed the methods to create an Ureaplasma vaccine and evaluate the efficacy and its subsequent antibody production. Specifically: Vaccine Development: In developing this DNA vaccine the Ureaplasma gene of interest was cloned and inserted into a pVAX1 vector. Briefly, the DNA fragment responsible for the multiple antigen binding (MAB) region of Ureaplasma serotype 6 (386 bp) was generated by PCR with specific primers: sense (TG TTC ATA TTT TTT ATC AG; SEQ ID NO:2); antisense (CCAAATGACCTTTTG-TAACTAGTA; SEQ ID NO:3). In order to increase the efficacy of antigen expression, a Kozak codon (ANNATGG; SEQ ID NO:1) was inserted at the beginning of the sense primer. The stop codon used was that provided in the vector (TAG). The DNA fragment from the PCR was then inserted into the vector pVAX1 (Invitrogen). This vector contains an early CMV promotor and a bovine growth hormone polyadenylation. The plasmid vector containing the antigen gene was transformed into E. coli (DH5a), clones were selected, and grown in LB media. Plasmid DNA was purified with a Qiagen miniprep kit. The orientation of the insert was confirmed by enzyme digestion and then the correct plasmid DNA was grown in LB media for injection. Each kit allowed us to isolate 1 mg of pDNA.

ELISA Assay (Whole Bacteria): This was performed as previously reported (Echahidi et al., 2001) with modifications. In brief: Ureaplasma reference strains were grown in 10 ml of 10 B broth to $10^6$ ccu/ml. Organisms were centrifuged at 25,000×g for 30 min at 4° C. and harvested. The pellet was washed thrice with phosphate-buffered saline (PBS), the final pellet resuspended in 100 µl of PBS, and diluted with methanol to 10 ml. To coat the microtiter plates, 100 µl of the antigen preparation diluted in methanol was added to each well and incubated at room temperature overnight until complete methanol evaporation. The wells were saturated with bovine serum albumin (3% [wt/vol]) in PBS and washed twice.

Washing was performed with PBS containing 0.1% Tween 20. 100 ul of mouse serum diluted 1:2 in PBS was added to the wells and incubated for 1 hr at room temperature. After a wash, 100 µl of horseradish peroxidase-labeled polyclonal anti-mouse immunoglobulin diluted in PBS containing 0.05% Tween 20 was added to the wells and the mixtures were incubated for 30 min at room temperature. After a wash, the peroxidase substrate (o-phenylenediamine) was added to the wells and the mixtures were incubated for 15 min in the dark at room temperature. The substrate reaction was stopped by adding $H_2SO_4$ (4 N), and optical density (OD) measured at 490 nm Negative controls were obtained by testing the conjugate without adding serum. The blank wells received ELISA reagents but no antigens or serum. Standard statistical methods were used to evaluate the data. Results: The serum level of antibody against Ureaplasma was detected using an ELISA with a clinical strain for serotype 14. Optical density increased from 1.0 to greater than 3.3.

Immunization of Mice: Adult female FVB white mice were injected intraperitoneal (IP) with 500 ug per dose of the vaccine with different schedules. Group 1 received vaccine day 0 and 11 wks. Group 2 received vaccine day 0, 4 wks, and 11 wks. Blood was collected from the vaccinated mice every 2 wks after the first vaccination and serum isolated.

Bacterial Killing Assay: To determine if the antibody generated by the vaccine participated in bacterial killing, we performed a previously reported neutrophil-mediated bacterial killing assay (Weisman and Lorenzetti, 1989) with modifications: In summary, we used 20 ul of $10^7$ cells/ml of neutrophils which were isolated from healthy donors (Gulf Coast Blood Center, Houston Tex.), 20 ul of $10^6$ ccu/ml serotype 14 Ureaplasma, 10 ul of human complement sera (Sigma, 51764 pre-adsorbed with S. epidermidis) diluted 1:4, 20 □1 of heat inactivated mouse serum (as an antibody source) collected at 12 wks after first vaccine injection, and qs the final well volume to 200 µl with 10B broth. Bacteria, serum, complement, and neutrophils were added together in microtiter plate wells, sealed and incubated at 37° C. for 5 days. Other wells contained bacteria alone, bacteria and serum, bacteria and neutrophils, bacteria and complement, bacteria with serum and neutrophils, bacteria with serum and complement, bacteria with complement and neutrophils. Control wells contained no bacteria with each of the combinations above. The OD was read at 650 nm every 2 hours in a microtiter plate reader for the first 48 hr and every 24 hr for next 72 hours. The 10 B media is pH sensitive and converts from yellow to red with growth of the bacteria. Color change was also visually evaluated every 6 hrs. No change in color or absorbance was observed with the negative controls. The Wilcoxon-rank sum test is used to compare bacterial killing among the different groups at the different dilutions. Results: Animals who received 500 ug/dose of the vaccine at 0, 4 and 11 wks, were bled at 12 wks. Serum demonstrated evidence of bacterial killing of a clinical strain of *Ureaplasma* serotype 14 at a >1:80 dilution.

Animal Models: Two animal models of *Ureaplasma* infection have been developed in pups including a sepsis model (Kong et al., 2008) and a bronchopulmonary dysplasia (BPD) model (Walls et al., 2009). The vaccine's effect on the sepsis model has been evaluated. The BPD model is more time consuming and expensive and will be evaluated when the vaccine is optimized.

In vivo Protection from Sepsis in Pups: All vaccinated mice were mated with males at 12 wks after the first vaccination. Pups were delivered at 15 wks. Pups were then infected with 2 doses of 0.1 cc of $10^6$ ccu/ml of *Ureaplasma parvum* clinical strain B079 serotype 14 at one day of age. Control litters were composed of pups born to unvaccinated dams and infected with the same dose and strain of *Ureaplasma*. The survival rate was calculated after 8 days and compared between litters born to vaccinated and unvaccinated dams. In Study #2, pregnancy was initiated in the same dams at 17 wks. Pups were delivered at 21 wks and treated similarly. Standard analyses of proportions were used to assess the statistical significance. The results are described below:

| Vaccine Doses: | Two | Three | Control |
| --- | --- | --- | --- |
| Study 1: | | | |
| N = | 20 | 19 | 27 |
| N Survival at 48 hrs = | 16 | 18 | 14 |
| % Survival at 48 hrs = | 80 | 95 | 52 |
| P value vs control | 0.067 | 0.0027 | |
| Study 2: | | | |
| N = | 8 | 13 | 52 |
| N Survival at 48 hrs = | 5 | 11 | 18 |
| % Survival at 48 hrs = | 63 | 85 | 35 |
| P value vs control | 0.24 | 0.0016 | |
| Combining Study 1 and 2: | | | |
| N = | 28 | 32 | 79 |
| N Survival at 48 hrs = | 21 | 29 | 32 |
| % Survival at 48 hrs = | 75 | 91 | 41 |
| P value vs control | 0.0021 | 0.000001 | |

This DNA vaccine given to mice before pregnancy is effective in preventing sepsis and death in pups of vaccinated dams for at least two consecutive pregnancies. It also is effective against an *Ureaplasma* strain/serotype of infecting organism different then that from which the vaccine was developed, suggesting a broad range of efficacy.

Exemplary Studies:

Optimize vaccine design: A vaccine may be optimized to enhance its efficacy and effectiveness for further development and use. Specifically, one could utilize one or more of the following changes in design: 1) Add the MPV-CTE+rev to the current vaccine to increase envelope expression and immunogenicity. 2) Exchange the pVAX1 vector with the pVAX200-DEST vector in the vaccine plasmid. 3) Express more than one immunogen in the plasmid to enhance the vaccines efficacy and impact. Specifically express the multiple binding proteins (MBP) from several if not all serotypes of *Ureaplasma.* 4) Add an N-terminal ubiquitin signal to the stop code. 5) Add strings of MHC class I epitopes from different pathogens or oligonucleotides (e.g. CpG motif) to the plasmid raise cytotoxic T-cell responses. 6) Add human granulocyte-macrophage colony-stimulating factor (hGM-CSF) as an immune enhancer to the plasmid to possibly further optimize the vaccine.

Optimize vaccine delivery: In light of the successful response to the vaccine we have observed to date, one can optimize the vaccine's delivery system to enhance its efficacy and effectiveness for further development and use. Thus one can characterize different delivery systems. The most expensive and time consuming aspect of the vaccines production is the amount of pDNA that must be produced, so one can reduce that while maintaining or increasing efficacy. Specifically, one can decrease the dose of the vaccine to 0.2 to 200 ug. Utilizing the smallest effective dose, one could investigate the delivery system including: 1) Delivery of an aqueous solution using methods different from the current IP system including IM, ID and SC routes. 2) Delivery of gold or tungsten microparticles with vaccine absorbed onto their surface via the ED route. Since this organism is a sexually transmitted disease, we would also investigate this method via the vaginal mucosa. The most effective delivery system will then need to be evaluated for impact of the animal's age and sex on the immune response.

Evaluation of vaccine design and delivery optimization: To evaluate the proposed vaccine design and delivery changes we will use a series of methods including: 1) Incorporation of tracer (e.g. LacZ) into the target cells in vitro and in vivo (see elsewhere herein for Methods). 2) Changes in the vaccinated animal's serum total antibody against *Ureaplasma* (of varying serotype) whole bacteria as detected by ELISA (see elsewhere herein). 3) Changes in vaccinated animal's serum specific antibody against *Ureaplasma* (of varying serotypes) MBP as detected by ELISA (see below for Methods). 4) Changes in vaccinated animal's serum bacterial killing assay against live *Ureaplasma* (of varying serotypes) as detected in culture (see elsewhere herein). 6) Changes in the survival, bacteremia, and inflammation of infected pups of vaccinated animals in multiple models of *Ureaplasma* infection including sepsis (see elsewhere herein), BPD (see elsewhere herein). 7) Changes in male or female mouse genitourinary and or gastrointestinal *Ureaplasma* colonization. (see below Methods) 8) Changes in pregnancy outcomes (pup number, pup size, gestation length) of females if they or their male partners or both are infected (see below Methods).

Incorporation of LacZ Tracer: This may be utilized as previously described in organisms (in-vitro) (Silva et al., 2009) and cells/tissue (in vivo) (Joussemet et al., 2005) and provide us with rapid feedback on the changes made to both the vaccine's design and delivery.

ELISA Assay for MBA: This MBA assay is performed as previously reported (Vancutsem et al., 2008) with modifications. In brief: Recombinant MBA (rMBA) is produced from the serotype and strain of *Ureaplasma* used for the vaccine to determine the amount of MBA specific antibody present in the serum of vaccinated animals or the pups of vaccinated animals. The MBA gene of interest is produced, cloned, expressed, purified and evaluated against animal serum. In addition one can characterize the antigen and the antibody (class and subclass) using standard immunologic techniques.

Bacterial Adherence Assay: This adherence assay is performed as previously reported (Smith et al., 1994; Thirkell et al., 1989; Torres-Morquecho et al., 2010) with modifications. In brief: A594 cells obtained from the ATCC are grown in DMEM supplemented with 10% FBS and without antibiotics at 37° C. *Ureaplasma* in 10B broth is added at a concentration of about $10^5$ ccu/ml to all wells of a six well plastic plate, serum at various dilutions are added to each well, and incubated. Control wells can contain 10 B media only and serum of non vaccinated animals or pups of these animals. All experiments are conducted in duplicate.

Adherence of *Ureaplasma* is quantified using a colorimetric method (Bertholet assay) that monitors ammonia produced from urea by *Ureaplasma* urease. The Mann-Whitney U test is used to evaluate the significance in adherence inhibition generated by the serum of vaccinated animals or pups of these animals.

Additional Animal Models: One can evaluate the impact of the vaccine on additional adult male and female animal models that have yet to be made operational including at least: 1) Genitourinary and Gastrointestinal Colonization: This has previously been reported and one can adapt these methodologies. (Audring et al., 1989; Furr and Taylor-Robinson, 1993; Iwasaka et al., 1986) In short, estrogen (female) and testosterone (male) treated mice are given oral and or genitourinary inoculations of *Ureaplasma* and colonization is reported to be prolonged (>3 weeks) and very heavy (>100 ccu/swab). 2) Infertility and Low Birth Weight: This has previously been reported and one can adapt these methodologies. (Audring et al., 1989; Engel et al., 1988; Swenson and O'Leary, 1978) In short: Colonized males and/or females are mated. The success of matings in vaccinated versus non-vaccinated controls is calculated, birth weight measured, and the number of pups counted. Once these models are operational, one can incorporate them into the evaluation of the vaccine's impact. One can initially use a pup sepsis and BPD model to assess the clinical outcome of vaccine intervention, but one can subsequently employ the vaccine in these other models.

Organisms: *Ureaplasma* serotypes/strains are grown in 10 B broth before each use from a frozen stock solution ($5 \times 10^6$ ccu/ml). The effectiveness of each vaccine is tested against each serovar of biovar *parvum* because it appears most significant and for key biovar *urealyticum* (Blanchard et al., 1990; Blanchard et al., 1993; Brown et al., 1981; Cassell et al., 1983) serovar.

Animals: FVB albino mice are used for all the animal experiments and fed antibiotic free water and food ad libitum. Pregnancies result from time impregnation at an animal facility. Pups are kept with dams throughout each experiment. At 14 days surviving pups are either euthanized or weaned.

Example 3

Perinatal *Ureaplasma* Infection and Suckling Mouse Brain Development

*Ureaplasma* have the following characteristics: small (0.1-0.85 um); devoid of a cell wall (insensitive to penicillin and gram stain); need urea for growth and produce urease (Pollack, 1986); not folic acid synthesizers (not susceptible to sulfonamides or trimethoprim). The most sensitive method of isolating *Ureaplasma* is inoculation in to liquid medium, detection by urease activity, and subculturing to agar for colony identification (Robertson, 1978; Taylor-Robinson, 1989; Taylor-Robinson et al., 1967; Taylor-Robison and Gourlay, 1984; Taylor-Robinson, 1989). Simple and rapid methods of *Ureaplasma* identification such as PCR have been developed and confirm culture (Abele-Horn et al., 1996; Blanchard et al., 1990; Blachard et al., 1993; Cunleffe et al., 1996; Willoughby et al., 1990), but commercial kits are not yet readily available. The diagnosis of *Ureaplasma* infection is complicated by its lack of gram staining, fastidious nature, and need for special growth and transport media. In view of these difficulties in identification, unless *Ureaplasma* is anticipated it may escape detection and that may explain the relative paucity of reports and clinical experience. PCR may remain positive for months and thus may only represent nonviable organisms (Cassell et al., 1983; Clifford et al., 2010). Thus, more laborious, complex identification methods are required, and only a few laboratories have that capability.

*Ureaplasma* attaches and invades a variety of cells (Busolo et al., 1984; Masover et al., 1977; Robertson et al., 1991; Saada et al., 1991; Shepard and Masover, 1979; Smith et al., 1994; Torres-Morquecho et al., 2010); is associated with cell apoptosis (Li et al., 2002); increases inflammatory cytokines (McGarrity and Kotani, 1986; Smith et al., 1994; Torres-Morquecho et al., 2010).

Prevention or Treatment of *Ureaplasma* Infection: Eradication of *Ureaplasma* from the urogenital tracts of women and their partners has been proposed. (Kundsin et al., 1996) However, *Ureaplasma* is not susceptible in-vitro to penicillins, sulfonamides, trimethoprim, aminoglycosides, and clindamycin, but are generally (about 90%) susceptible in-vitro to tetracyclines, and variably to macrolides (e.g. erythromycin). (Cassell et al., 1993) In recent studies, these variable susceptibilities. (Molina et al., 2010; Okunola et al., 2006; Okunola et al., 2007; Weisman et al., 2009) Prophylactic antibiotics at delivery did not effect *Ureaplasma* colonization of the chorioamnion. (3) Macrolides (Eschenbvach, 1993; Mazor et al., 1993; Romero et al., 1993) have not been reliable eradicating genital tract *Ureaplasma* or adverse perinatal outcomes in two randomized controlled trials. In addition, in couples attending infertility clinics, genital tract *Ureaplasma* persisted despite antibiotics. (Hipp et al., 1983) Although newer antibiotics (e.g. glycylcyclines (Kenny and Cartwright, 1994) and quinolones (Kenny and Cartwright, 1996)) may prove more effective, safety and efficacy during pregnancy are unproven. In view of the high colonization and sexual transmission rates, and variable sensitivity of *Ureaplasma*, it is unlikely that current antibiotic strategies will be effective in its eradication.

It has been suggested but not demonstrated that lack of specific antibody may be critical for preventing *Ureaplasma* infection, because specific antibody may inhibit growth in vitro. (Cassell et al., 1993) Hypogammaglobulinemic patients have an increased susceptibility to *Ureaplasma* (Taylor-Robinson et al., 1986) and serological studies of hypogammaglobulinemic patients (Volger et al., 1985), pre-term infants (Quinn et al., 1983), and women with recurrent spontaneous abortions (6.1) support this concept. The increased susceptibility of infants <30 wks gestational age to *Ureaplasma* respiratory disease may be related to hypogammaglobulinemia (5) or lack of specific antibody (Cassell et al., 1988; Casell et al., 1988). It has been suggested but not demonstrated that monoclonal antibodies to specific protein antigens of *Ureaplasma* can inhibit growth of these organisms in-vitro and indicates that specific antibody may be important for host defense. (Watson et al., 1990)

Neurologic Impact of *Ureaplasma*: Considerable evidence links *Ureaplasma* respiratory colonization with neonatal lung morbidity, but few studies investigate intrauterine *Ureaplasma* with neurologic morbidities and they are listed here. The risk of severe IVH (grade ≥3) was 2.5 fold higher in serum *Ureaplasma* PCR-positive (n=74) than PCR-negative infants (n=239) after adjustment for gestational age. (Viscardi et al., 2008) *U. parvum* was the species identified in all PCR-positive infants with severe IVH. The risk for severe IVH increased to five fold in PCR⁻ positive patients with elevated serum IL1β. Another (n=866) report (Olomu et al., 2009), observed that *Ureaplasma* in the placenta parenchyma before 28 weeks was associated with increased: preterm labor and delivery; fetal and maternal inflammation; intraventricular hemorrhage; echolucent brain lesions. These lesions predict motor and cognitive limitations and poor outcome. (Leviton et al., 1999) Another study observed Ureaplasma infection of the amniotic cavity at the time of preterm birth (n=67) was associated at 2 years with: abnormal PDI score (OR 3.1, CI 1.3-7.1); abnormal neurologic outcome (OR 4.8, CI 1.7-13.8); higher probability of cerebral palsy (OR 4.8, Cl 1.4-16.4) vs control patients (n=47) with amniotic fluid negative for Ureaplasma, irrespective of gestational age or birthweight. (Berger 2009) Several groups have suggested that proinflammatory cytokines (e.g. IL-1β, IL-6, and TNF α) might be the link between perinatal infection and neonatal brain damage. (Dammann et al., 1997; Kaukola et al., 2006) and one study (n=1078) of high risk patients, reported the timing and use of antibiotics affected development of echolucent brain images (Leviton et al., 1999). Although more information is needed to assess Ureaplasma's contribution to adverse neurodevelopment, Ureaplasma exposed infants appear more severely affected neurologically.

The role for Ureaplasma in brain injury is supported in the only report of a mouse model. In this model (Normann et al., 2009), intraamniotic infection with Ureaplasma leads to inflammation and disturbed brain development. Specifically, they observed: a decreased density of calbindin protein-positive and calretinin-positive neurons, suggesting a disturbed production, maturation, and or survival of interneurons, which play a key role in associative and cognitive functions (Mohler, 2007); decreased MBP staining which most likely reflects decreased myelination which again has been associated with limited cognitive function (Back, 2006), and increased central microglial activation which the authors speculated most likely participated in the effects on interneurons and myelin. In certain aspects, these observations could have been due to direct spread and infection of the brain or secondary immune or inflammatory effects or both. A primate model (Novy et al., 2009) indicates both since they observed that intraamniotic infection with Ureaplasma lead to a systemic inflammatory response and in some instances cerebrospinal fluid cultures that contained Ureaplasma. Depending on the mechanism of the injury, treatments would vary.

There have been reports of Ureaplasma cultured from the brains of infants including two preterm infants who died of intraventricular hemorrhage (Ollikainen et al., 1993) and a neonate with a brain abscess. (Rao et al., 2002) There have been 72 cases reported of Ureaplasma meningitis. (Cassell et al., 1988) Seven prospective studies estimated the incidence of Ureaplasma in neonates presenting with clinical symptoms. In studies of 100 (Waites et al., 1988) and 313 (Viscardi, 2010) and 66 (Sethi et al., 1999) preterm infants, CSF grew Ureaplasma in 8%, 19.1%, and 9% of patients respectively. In a study of 318 neonates (only one preterm) born at a community hospital (Waites et al., 1990) and 69 neonates of variable gestation (Olomu et al., 2009), 1.6% and 1.5% grew Ureaplasma from their CSF respectively. The largest study reported an incidence of 0.2% in 920 infants but the methods appeared flawed and insensitive (Waites et al., 1995). There are also seven case reports or small case series reporting Ureaplasma as a cause of meningitis. (Biran et al., 2010; Chung et al., 2007; Garland and Murton, 1987; Hentschel et al., 1993; Neal et al., 1994; Singh et al., 2003; Stahelin-Massik et al., 1994) Of the reported patients with Ureaplasma meningitis, 86% were premature, 90% were in the first 2 weeks of life, 90% were asymptomatic, and 72% were U. parvum. Although abnormalities in CSF cell count, glucose and protein are described, all or some of these can be absent in many cases. It also remains unclear whether Ureaplasma enters the CSF via the blood (15% had positive blood cultures) or directly from the respiratory tract (33% had positive respiratory cultures) across the cribriform plate or both, or Ureaplasma's impact is affected via inflammatory mediators or the infant's immune response following colonization in the perinatal period.

The inventors have developed the following: assays to identify Ureaplasma (physiologic, culture, and PCR) its biovars, serovars, and antibiotic sensitivity (Molina et al., 2010; Okunola et al., 2006; Okunola et al., 2007; Weisman et al., 2009); suckling mouse models to evaluate the affect of this organism and antibiotic treatment or prevention strategies in Sepsis (Kenny and Cartwright, 1996) and BPD (Walls et al., 2009). Most recently the inventors developed an Ureaplasma rDNA vaccine.

Ureaplasma Vaccine Development: The portion of the MBA Ureaplasma gene that codes for a constant region across all serotypes was selected as the target for vaccine and antibody development. Serotype 6 was selected as the gene source because it is frequently an invasive clinical serotype. (Vancustem et al., 2008) In developing this rDNA vaccine the Ureaplasma gene of interest was cloned and inserted into a pVAX1 vector. A whole bacteria ELISA assay was performed as previously reported (Echahidi et al., 2001), with modifications, on serum samples from dams, and there were significant antibody levels (optical density increased from 1.0→3.3) against a serotype 14 clinical strain of Ureaplasma with appropriate controls. A bacterial killing assay, as we previously reported (Weisman et al., 1989) with modifications, demonstrated evidence of bacterial killing at >1:80 dilution against a serotype 14 clinical strain of Ureaplasma with appropriate controls. A sepsis model (Kong et al., 2008) as previously reported was used to evaluate in vivo the protection to the maternal vaccine provided pups. This rDNA vaccine given to mice before pregnancy was effective in preventing sepsis and death (91% vs 41%, p<0.000001) in pups of vaccinated dams for at least two consecutive pregnancies, against an Ureaplasma infecting organism of a different serotype (Casell et al., 1988) then that from which the vaccine was developed (Biran et al., 2010), indicating a broad efficacy.

Exemplary Study Design and Methodology:

To develop a mouse model of antenatal Ureaplasma chorloamnionitis, one can utilize the method recently published (Normann et al., 2009) and somewhat modified. In short: 1) one can mate female FVB white mice (Charles River, Wilmington, Mass.) with male C57 BL6 mice (Charles River) to generate a pup F1 FVB:C57BL6 hybrid for study. One can generate the hybrid because FVB white mice can develop blindness by 6 months of age and that would interfere with the developmental testing. The FVB mouse is utilized, in certain cases, because our Ureaplasma animal investigations have been conducted in these mice. 2) a clinical strain of Ureaplasma serotype 14 are grown in selective media from a frozen aliquot, 2) embryonic day (e) 13.5, pregnant FVB white mice re randomly allocated to one of two intraamniotic fluid injection substances: a) saline injection, b) Ureaplasma injection (5000 ccu). One can inject Ureaplasma in saline, without media, to eliminate the potential inflammatory effects of the media previously reported (Normann et al., 2009). Under sterile conditions, pregnant dams are anesthetized with isoflurane. The uterus externalized through a 12 mm abdominal incision and soaked with prewarmed saline. Ten ul of study substance will be injected into each amniotic sac. The abdominal wall is then closed in two layers. Dams may be recovered with water and food ad lib, and pain medication.

To evaluate the development of chorioamnionitis in this model, at e17.5 one can obtain the following: 1) Quantitative Blood Culture and PCR for *Ureaplasma*: Fetal blood is obtained and quantitative PCR and culture for *Ureaplasma* is performed. In the latter, blood is immediately incubated in 10B broth at 37° C. in serial dilutions and color change of media will signal *Ureaplasma* growth, which is confirmed by visualization of colonies on agar and with PCR. (Walls et al., 2009). In the former, serum is separated and frozen for batch analysis of *Ureaplasma* PCR as previously reported. (Weisman et al., 2009) b) Quantitative Amniotic Fluid Culture and PCR: Amniotic fluid is aspirated and quantitative culture and PCR is immediately performed as described for blood. c) Quantitative Placenta Culture and PCR: Placental tissue is obtained and immediately ground, and quantitative culture and PCR is immediately performed as described for blood. d) Placenta Histopathology: Placental tissue is obtained and immediately processed as previously described. (Redline t al., 1998) All specimens are read by a placenta pathologist blinded to the group assignment. Histologic chorioamnionitis is separated into maternal and fetal response and assigned a stage accordingly. (Redline et al., 1998) e) Blood, Amniotic Fluid and Placenta Inflammatory Mediator Levels: Serum, amniotic fluid, and ground placenta are immediately frozen in liquid nitrogen and then stored at −80° C. until a batch ELISA assay (Normann et al., 2009) for inflammatory mediators IL1α, IL1β; IL6, TNFα, IFNγ, MIP-2, MCP-1, and TGF-β1 is performed.

To determine the effect of *Ureaplasma* chorioamnionitis on brain development, one can use the model above and determine the following: 1) Brain Infection and Inflammation: To describe the associated brain infection and inflammation in this model, at e17.5, and 6 and 18 wks after birth we will remove the pup's head with a guillotine, peel off the skull and obtain: a) Quantitative Brain Culture and PCR for *Ureaplasma*: The left hemisphere is isolated, immediately ground up and processed for culture and PCR as described above. b) Brain Inflammatory Mediator Levels: The right hemisphere is isolated and immediately ground up, frozen in liquid nitrogen and then stored at −80° C. until a batch ELISA assay is performed as described above. 2) Brain Histology and Histochemistry: To describe the associated brain pathology in this model, at e17.5, and 6 and 18 wks after birth one can remove the pup's head with a guillotine, peel off the skull, place the entire brain in formalin and perform routine histopathological studies. Initial characterization involves basic histopathology studies looking for changes such as cortical thickness, sign of tissue loss, microcephaly, etc., for example. If pathologic, neurologic or developmental phenotypes are detected (see below) one can expand the analysis using specific neuronal markers. For evidence of synapse disease, one can use vesicular glutamate transporter to label excitatory synapses. For evidence of gliosis one can use antibodies to glial fibrillary acidic protein (GFAP). 3) Neurologic Phenotype: To determine if a neurologic phenotype occurs, pups will be examined at birth, weekly for 3 weeks, then every 3 wks for 18 wks to include: weight, survival, hair condition, eye condition, spine condition, tremor, stereotypes, hind-limb clasping, and myoclonus. These tests should provide a timeline of onset of neurologic symptoms. Most of the evaluation can consist of observation of the animals in the cage and in the palm of the examiner 4) Developmental Phenotype: To determine if a developmental phenotype occurs, pups can undergo the same battery of tests in the exact order listed below at 6 and 18 wks after birth. These tests were selected because they are robust and assess multiple neurobiological phenotypes including motor function, activity, balance and coordination, anxiety, social interactions, learning and memory, and abnormal movements. Developmental tests are only performed at 18 weeks if a neurologic phenotype is observed by 18 wks or a developmental phenotype is observed at 6 weeks. All tests are performed by investigators blinded to the group assignment. Dowell Test: (Samaco et al., 2008) This tests coordination and balance by placing an animal on top of a 0.7 cm horizontal dowel suspended 60 cm above a padded surface. The time to fall is recorded. The test ends after 120 seconds. Wire Hang Test: (Samaco et al., 2008) A string is suspended 60 cm above a padded surface and the mouse is allowed to hang onto the string by their front paws. The time to fall is recorded. The task ends after 60 seconds. Open Field Analysis: (Samaco et al., 2008; Spencer et al., 2005) This test measures locomotor activity and anxiety. The apparatus consists of a 40 cm×40 cm×30 cm plexiglass enclosure where an observer records the horizontal and vertical activity of the mouse. A mouse is placed inside the enclosure and monitored for 30 minutes to assess locomotion and anxiety. The total distance traveled and the amount of time spent moving determines amount of locomotion. The ratio of the distance traveled in the center of the field to the total distance traveled indicates level of anxiety; animals that are anxious avoid the center of the field. Vertical activity is also an indirect measure of anxiety. Light/Dark Box: (Spencer et al., 2006) The light/dark test measures anxiety based on the percentage of time the test animals spend within the dark side of the box. A plexiglass chamber is divided into two compartments connected by a small opening. The "light side" compartment is made of clear Plexiglass and the "dark side" compartment is of opaque dark plexiglass. The environment is controlled with 50 lux ambient lighting and 60 dB white noise. The animal is placed into the anxiety-generating "light side" and the number of transitions between sides and total time spent in each side is recorded for 10 minutes. Total number of transitions, time spent in the light side, latency to enter the dark, and latency to enter the light will be compared between groups. Partition Test: (Samaco et al., 2008; Spencer et al., 2005) This test measures social interaction and behavior. The test apparatus consists of a standard cage divided in half by a clear perforated partition. Experimental animals are individually housed in one side for 3 days until eighteen hours prior to the experiment when a gender/age/weight matched FVB: C57BL6 F1 mouse is placed in the opposite side. An observer will be used to measure the experimental mouse's approaches and time spent at the partition. The first phase of the test measures interaction with a familiar mouse (placed eighteen hours prior to start) and the second phase measures the interaction with a novel mouse. At the end of the test the novel mouse is replaced with the original familiar mouse and the experimental mouse behavior is scored. Morris Maze: (Watase et al., 2007) This test assesses contextual (hippocampus) and cue-based (amygdala and hippocampus) learning. Mice are trained in the Morris water maze to locate a hidden platform. Each mouse is given four trials per day for five consecutive days. After trial 20, each animal is given a probe trial. During the probe trial, the platform is removed and each animal is allowed to search the pool for 60 s. Tremor: (Alvarez-Saavedra et al., 2007) The degree of tremor present at 6 and 18 weeks of life will be measured by physical examination.

To pilot if antenatal maternal treatment affects *Ureaplasma* chorioamnionitis related brain changes, neurological and developmental phenotype experiments above are repeated in pups of *Ureaplasma* infected dams who received our *Ureaplasma* rDNA vaccine prior to conception vs non-vaccinated dams.

Sample size: Two litters (one saline and one *Ureaplasma*) are utilized for each of the blood, amniotic fluid, and placenta culture, PCR, and pathology experiments. These experiments are to describe infection and so no sample size is calculated, but the smallest sample size possible is a litter per group. Four litters (two saline and two *Ureaplasma*) are utilized for the inflammatory mediator data experiments. The sample size for inflammatory mediator data is based on differences previously published for a similar model. (Normann et al., 2009) Two litters (one saline and one *Ureaplasma*) are utilized for each of the brain culture, brain PCR, and brain pathology experiments at 07.5 days, because one litter is the smallest sample size one can select. Four litters (two saline and two *Ureaplasma*) are utilized for the inflammatory mediator experiment at e17.5 days. The sample size for inflammatory mediator data was based on differences previously published for a similar model. (Normann et al., 2009) The brain culture, brain PCR, brain pathology experiments at 6 and 18 wks, one can use about 3 pups per each time point/group/test or about a total 6 litters. These experiments are to describe infection and pathology so no sample size is calculated, The brain inflammatory mediators at 6 and 18 wks, one can use about 15 pups per each time point/group or about 8 litters The neurologic and developmental phenotype experiments utilize 8 litters or 16 pups per group (saline *Ureaplasma* with and without vaccine) which gives one a power of 0.8 (a=0.05) to detect 1 standard deviation difference between the saline and *Ureaplasma* groups in the unvaccinated dams and then again between the *Ureaplasma* groups of the vaccinated and unvaccinated dams, based on previous work by others. (97) One can assume a 20% wastage or loss of pups or litters based on previous work with these animals.

Data analyses: Standard statistical analyses are employed. For continuous data, the distributions of data re assessed and ANOVA is utilized for those that have a normal distribution and Kruskal-Wallis for those with a non-normal distribution. For categorical data the Fischer exact or Chi-square test is performed as appropriate.

Example 4

*Ureaplasma* Vaccine and Related Antibodies

The present example concerns exemplary optimization of vaccine delivery, dose, and schedule and also concerns evaluation of the immunological response to the vaccine and related antibodies.

Exemplary Methods:
A DNA vaccine was delivered as follow:
1) Vaccine preparation: pDNA containing conserved segment of MBA DNA from *Ureaplasma parvum* (serotype 6) was purified and diluted with normal saline to desired concentration (as described above). In addition, there is some data (Pathogen specific IgA, neutralizing antibody and animal survival on a vaccine comprised of the constant regions from both a *U. parvum* serotype 1 and serotype 6, resulting in a larger plasmid with twice the DNA.
2) Adult FVB mice (both female and male, age 3-4 weeks) were vaccinated with serotype 6 DNA vaccine by intraperitoneal (IP) at dose of 200 ug to 500 ug in 1 ml NS per injection (previously described) or by intramuscular (IM) at dose of 100 ng and 50 ug in 0.1 ml NS.
3) Frequency of injection:
   a. 500 ug×2 with 2 wks interval, IP
   b. 500 ug×3 with 2 wks interval, IP
   c. 200 ug×3 with 2 wks interval. IP
   d. 50 ug×3 with 2 wks interval, IM
   e. 100 ng×3 with 2 wks interval, IM
   f. All animals were boosted with same amount of pDNA as the initial inject at 12 wks after the first injection. Each group contains 5 animals.

Figure 2:
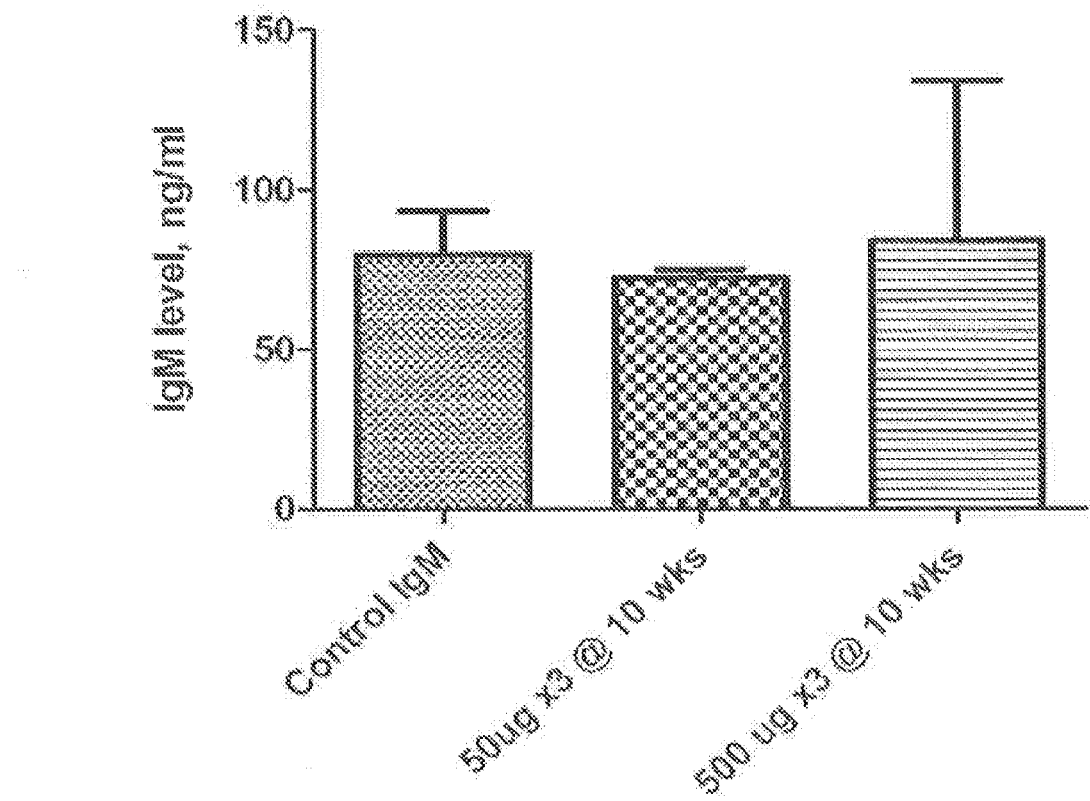
FIG. 2. Serum level of IgM in vaccinated mice
FIG. 3. Serum level of IgG subclasses in vaccinated mice FIG. 4. Serum level of pathogen specific IgG in vaccinated mice. Each data point contains serum from 3 animals and repeated 3 times.
Figure 3:
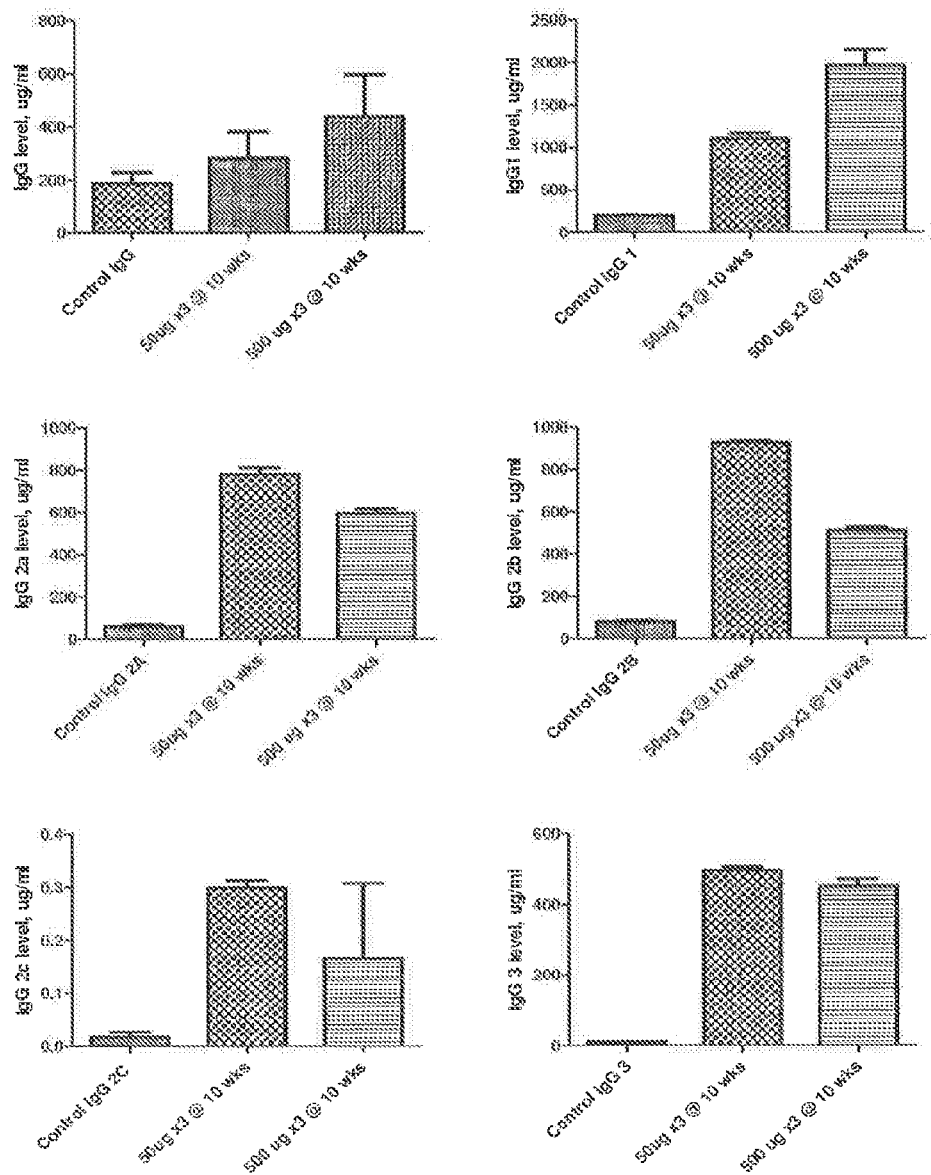

Results:
1. Serum Immunoglobulin Levels of Vaccinated and Control Mice:
Total IgA, IgM, IgG and Subclass IgG1, IgG2a, IgG2b, IgG2c, and IgG3 were evaluated with commercially available ELISA kits. The procedure followed the protocol provided in the kit. The results are shown as follow.
   a. The Total IgA level is significantly increased between vaccinated and control mouse serum, p=0.005, however there is no statistical difference between 50 ug IM and 500 ug IP vaccine groups. (see FIG. 1, which shows serum IgA level in vaccinated mice)
   b. There are no significant differences of IgM among vaccinated and control mouse serum. p=0.5 (see FIG. 2, which shows serum level of IgM in vaccinated mice)
   c. The Total IgG level is significantly increased between vaccinated and control mouse serum, p=0.008, however there Is no statistical difference between 50 ug IM and 500 ug IP vaccine groups. The IgG subclass level is significantly increased between vaccinated and control mouse serum for IgG1 (p=0.005), IgG2A (p=0.0002), IgG2B (p=0.001), IgG3 (p=0.0006), but not IgG2C (p=0.4). There is no statistical difference between the 50 ug IM and 500 ug IP vaccine groups for IgG 2C (p=0.52) and IgG 3 (p=0.17). However, IgG 1 is significantly less (p=0.03) for the 50 vs. 500 ug dose, while IgG 2A (p=0.01) and IgG 2B (p=0.02) are significantly greater for the 50 vs. 500 ug dose. (see FIG. 3, which shows serum level of IgG subclasses in vaccinated mice)

Figure 4:
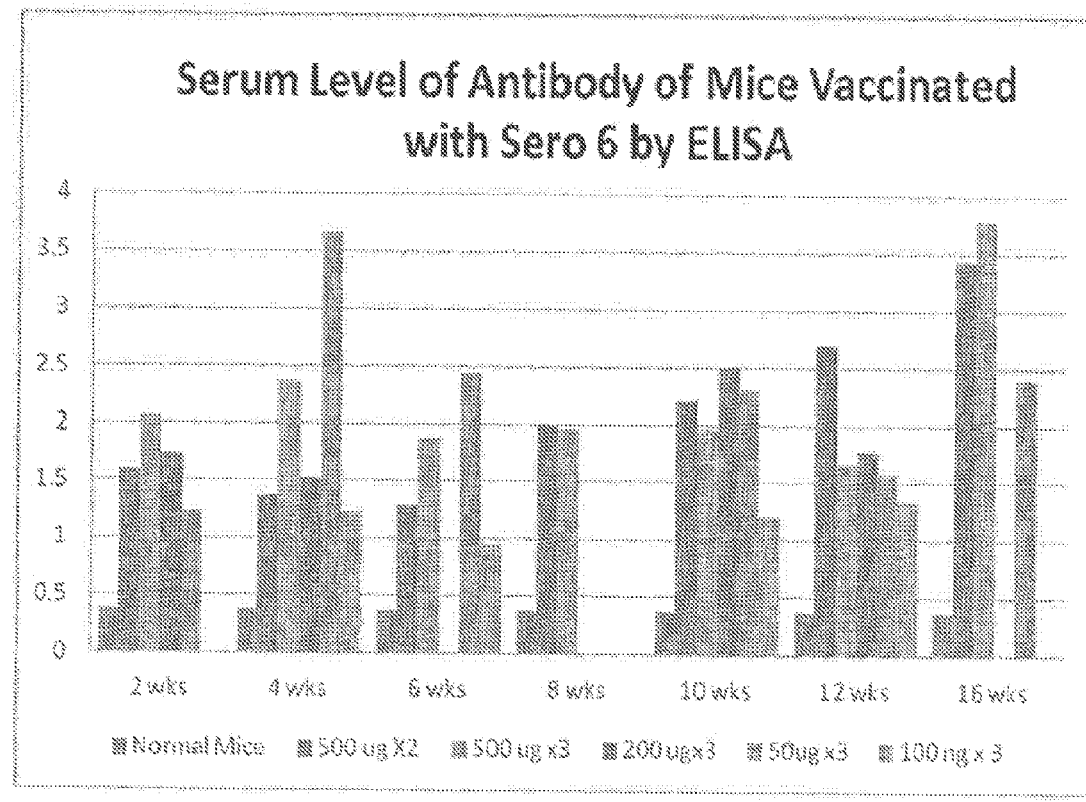

2. Serum Pathogen-Specific IgG Levels of Vaccinated and Control Mice:
Serum level of IgG against *Ureaplasma parvum* (serotype 14) as detected by whole bug ELISA. The pathogen specific antibody is significantly increased between all the vaccine groups and controls (normal mice). The results are shown in FIG. 4. Note: All serum are diluted 1:2 prior to assay.

TABLE 1

Serum Level of Antibody of Mice Vaccinated with *U. parvum* (serotype 6) by ELISA, OD

| | Normal Mice | 500 ug × 2 | 500 ug × 3 | 200 ug × 3 | 50 ug × 3 | 100 ng × 3 |
|---|---|---|---|---|---|---|
| 2 wks | 0.372 | 1.584 | 2.06 | 1.73 | 1.24 | |
| 4 wks | 0.372 | 1.378 | 2.374 | 1.515 | 3.67 | 1.235 |
| 6 wks | 0.372 | 1.294 | 1.874 | | 2.439 | 0.955 |

TABLE 1-continued

Serum Level of Antibody of Mice Vaccinated with *U. parvum* (serotype 6) by ELISA, OD

|        | Normal Mice | 500 ug × 2 | 500 ug × 3 | 200 ug × 3 | 50 ug × 3 | 100 ng × 3 |
|--------|-------------|------------|------------|------------|-----------|------------|
| 8 wks  | 0.372       | 1.992      | 1.956      |            |           |            |
| 10 wks | 0.372       | 2.208      | 1.956      | 2.51       | 2.31      | 1.202      |
| 12 wks | 0.372       | 2.696      | 1.652      | 1.77       | 1.569     | 1.344      |
| 16 wks | 0.372       | 3.432      | 3.78       |            | 2.402     |            |
| 20 wks |             |            |            | 2.721      | 0.882     |            |
| 31 wks | 0.167       | 3.8        |            |            | 0.937     |            |
| 46 wks |             |            |            | 2.61       | 0.622     |            |

Figure 5:
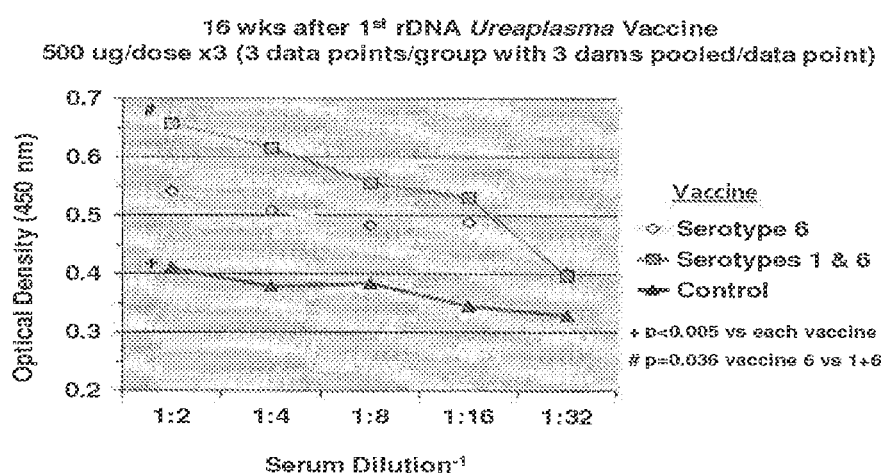
FIG. 5. Serum level of pathogen specific IgA in vaccinated mice. Each data point contains serum from 3 animals and repeated 3 times.

3. Serum Pathogen-Specific IgA Levels of Vaccinated and Control Mice:

Serum level of IgA against *Ureaplasma parvum* (serotype 14) as detected by whole bug ELISA. The results are shown in FIG. 5.

Figure 6:
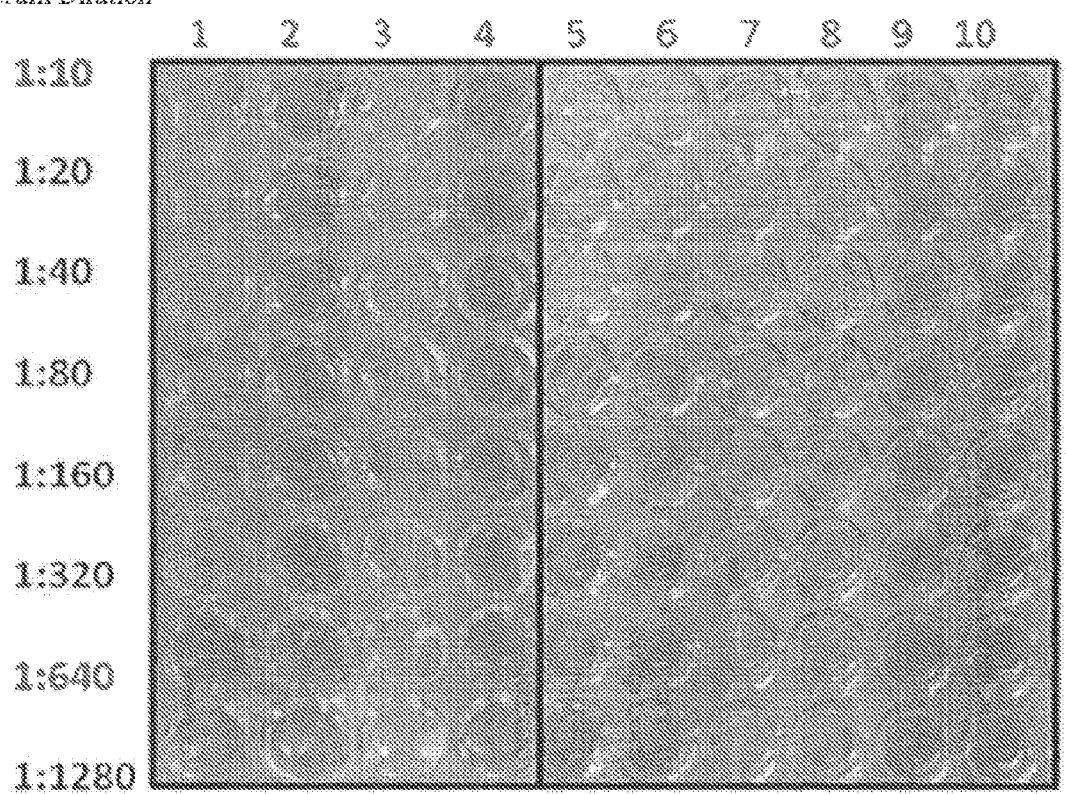
FIG. 6. In vitro bacterial killing assay of serotype A (*U. diversum*), 1, (*U. parvum*) and 8 (*U. urealyticum*) with serum from mice immunized (IMS) with *Ureaplasma* DNA vaccine serotype 6 (*U. parvum*) and serum from normal mice (NMS). Column 1, 5 & 6. *Ureaplasma* (Column 1 is Serotype A; Column 5 is Serotype 1; Column 6 is Serotype 8)+IMS. Column 3, 7 and 8 are 10B only. Column 2 and 4 are Serotype A+NMS. Column 9 is Serotype 1+NMS. Column 10 is Serotype 8+NMS.
Figure 7:
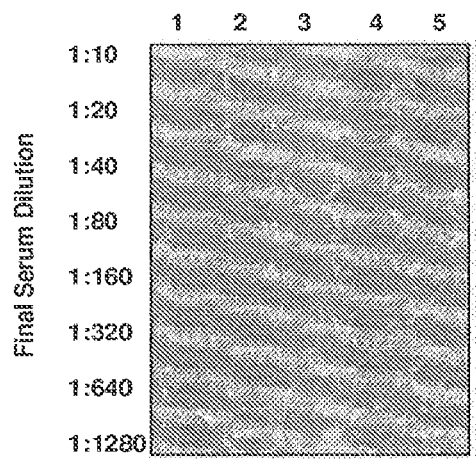
FIG. 7. In vitro bacterial killing assay of *Ureaplasma diversum* serotype A with serum from mouse immunized (IMS) with *Ureaplasma* DNA vaccine serotype 1 and 6 or normal mouse serum (NMS). All wells contain 10B broth+ *Ureaplasma* except Column 3. Column 1: IMS. Column 2: NMS. Column 3 10B only. Column 4 and 5: 10 B broth.
Figure 8:
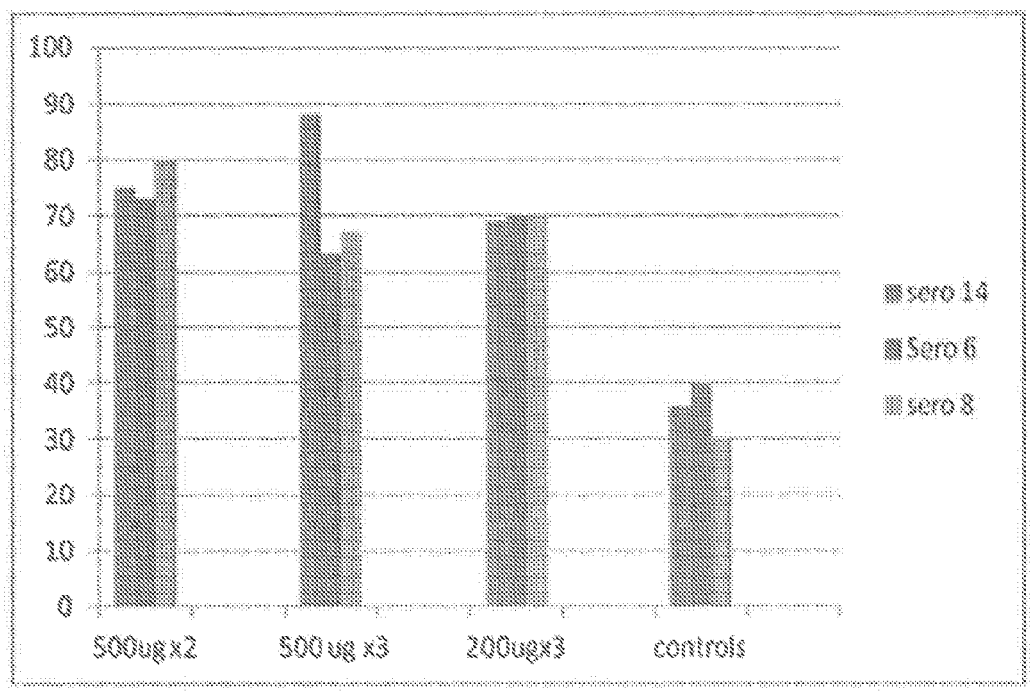
FIG. 8. Animal survival rate of the vaccine and nonvaccine groups against *Ureaplasma* infection with either serotypes 6 (*U. parvum*), 8 (*U. urealyticum*), or 14 (*U. parvum*).
Figure 9:
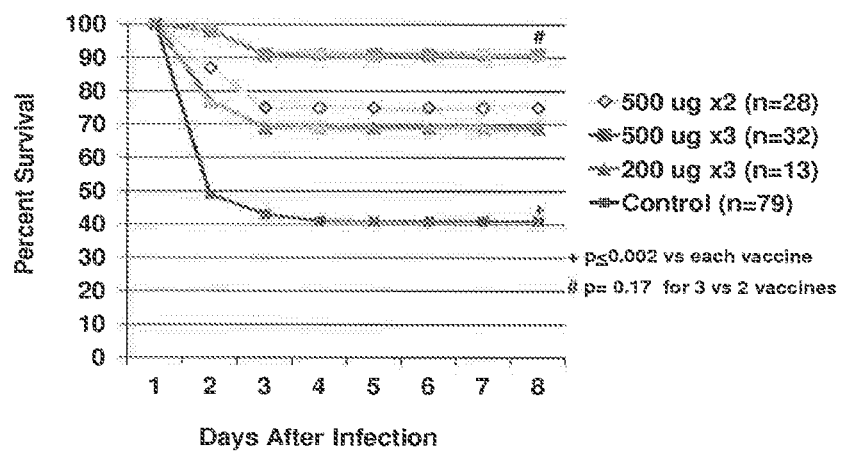
FIG. 9. Animal survival rate of the vaccine and nonvaccine groups against *Ureaplasma* serotype 14 infection.
Figure 10:
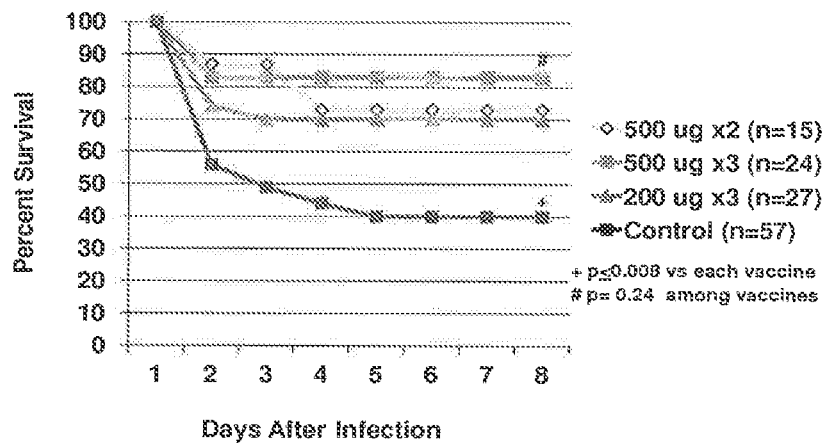
FIG. 10. Animal survival rate of the vaccine and nonvaccine groups against *Ureaplasma* serotype 6 infection.
Figure 11:
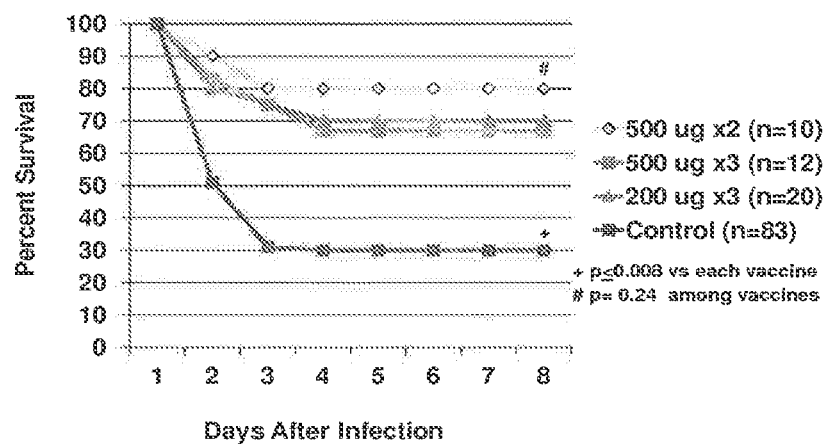
FIG. 11. Animal survival rate of the vaccine and nonvaccine groups against *Ureaplasma* serotype 8 infection.
Figure 12:
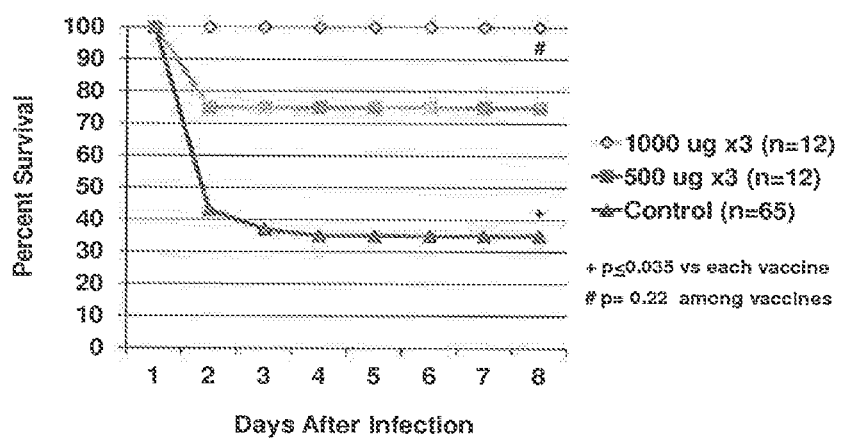
FIG. 12. Animal survival rate of the vaccine (serotype 1&6) and nonvaccine groups against *Ureaplasma* serotype 14 infection 4, 5, 7, 8, 9, 10, 11, 2, and 13. Members of Biovar 1 and Biovar 2 can be distinguished at least by DNA-DNA hybridization, restriction fragment length polymorphism, 1D and 2D gel electrophoresis, genomic sizes, and PCR ampliflification of certain genes. The different serovars each have a distinct antigen that, in some cases of the invention, are utilized as a target for the immunological composition. There are predominant antigens recognizable in patients infected with *Ureaplasma* (Watson et al., 1990; see also Teng et al., 1994; Zheng et al., 1995; Kong et al., 1999a; 1999b; nd Kong et al., 2000), and these are referred to as multiple-banded antigens.

4. Serum Neutralizing (Bacterial Killing) Antibody Levels of Vaccinated and Control Mice:

This assay was carried out on 96 cell culture plate. Each well contains: 10B medium; $10^2$ ccu *Ureaplasma*; serum from vaccinated or normal mice at different dilutions. The plate was incubated at 37° C. for 5 days. *Ureaplasma parvum* serotype 1 and 6, *Ureaplasma urealyticum* serotype 8, and *Ureaplasma diversum* serotype A were used for this in vitro assay. The serum from vaccinated mice has killing activity against all *Ureaplasma* species tested. In previous filing we have bacterial killing against *Ureaplasma parvum* serotype 14. Yellow color indicates no bacterial growth. Some of the results are shown in FIG. 6.

5. Animal Survival Following Infection of Vaccinated and Control Mice:

At 12 wks after the first injection of pDNA, all the animals received a booster injection. The mating was set up 2 days later. The pups from these females are infected with 2 doses of $10^6$ ccu of *Ureaplasma* at day 1 of life (4 hrs apart). The survival rate was calculated over the next 8 days and compared with pups of unvaccinated dams infected with same dose and strain of *Ureaplasma*. The survival rate of pups in the vaccinated group is significantly higher than the control group for every strain of infecting *Ureaplasma*. However, there does not appear to be a significant difference among the vaccinated groups in the doses tested to date. The data is displayed in FIGS. 8, 9, 10, 11 and 12. Animal survival studies are completed on the doses of 1000, 500 and 200 ug per dose. Survival studies are performed on 50 ug per dose and plan 100 ng per dose in the future.

In some embodiments, one can develop the protein product of the vaccine and this allows one to investigate the effects of: a protein vaccine; using the protein as a boost to the DNA vaccine (protein boost); developing and characterizing a monoclonal antibody from the protein. One can examine the effectiveness of a monoclonal antibody as a therapeutic target in humans, animals, and media/cell lines. One can improve the delivery system/platform/method for the pDNA vaccine, for example by investigating subcutaneous (SC) delivery at an optimum dose. One can also develop and if necessary collaborate with others to develop a platform to enhance vaccine delivery IM or SC. One can develop a platform to deliver the vaccine orally or nasally (e.g. cytofectin), for example. One can test the vaccine utilizing an electroporation delivery system, for example. One can characterize the mechanism of action of the vaccine including, for example, the cellular mediated immune response. One can characterize the impact of the vaccine (pDNA or protein or both) on animal models of chronic lung disease (BPD), chorioamnionitis, vaginitis, chronic prostatitis, neurologic disorders, preterm labor, etc.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

PATENTS AND PATENT APPLICATIONS

U.S. Pat. No. 3,826,364
U.S. Pat. No. 4,284,412
U.S. Pat. No. 4,498,766
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,661,913
U.S. Pat. No. 4,774,189
U.S. Pat. No. 4,767,206
U.S. Pat. No. 4,714,682
U.S. Pat. No. 4,857,451
U.S. Pat. No. 4,989,977
U.S. Pat. No. 5,160,974
U.S. Pat. No. 5,478,722

PUBLICATIONS

Abele-Horn M, Wolff C, Dressel P, Zimmermann A, Vahlensieck W, Pfaff F, Ruckdeschel G. Polymerase chain reaction versus culture for detection of *Ureaplasma urealyticum* and *mycoplasma hominus* in the urogenital tract of adults and the respiratory tract of newborns. Eur J Clin Microbiol Infect Dis 15:595-8, 1996.

Alarcon J B, Waine G W, McManus D P. DNA vaccines: technology and application as anti-parasite and anti-microbial agents. Adv. Parasitol. 42: 343-410, 1999.

Almendro et al., "Cloning of the human platelet endothelial cell adhesion molecule-1 promoter and its tissue-specific expression. Structural and functional characterization," J Immunol. 157(12):5411-5421, 1996.

Alvarez-Saavedra M, Stez M A, Kang D, Zoghbi H Y, Young M. Cell-specific expression of wild-type MeCP2 in mouse models of Rett syndrome yields insight about pathogenesis. Hum Mol Genet. 16:2315-25, 2007.

Andre S, Seed B, Eberle J, Schraut W, Bultmann A, Haas J. Increased Immune Response Elicited by DNA Vaccination with a Synthetic gp120 Sequence with Optimized Codon Usage. Journal of Virology 72 (2): 1497, 1998.

Andrews W W, Shah S R, Goldenberg R L, Cliver S P. Hauth J C. Cassell G H. Association of post-cesarean delivery endometritis with colonization of the chorioamnion by *Ureaplasma urealyticum*. Obstet Gynecol 85:509-14, 1995.

Angel et al., Cell, 49:729, 1987b.

Angel et al., Mol. Cell. Biol., 7:2256, 1987a.

Atchison and Perry, Cell, 46:253, 1986.

Atchison and Perry, Cell, 48:121, 1987.

Audring H. Klug H, Bollmann R. Sokolowska-Kohler W, Engel S. *Ureaplasma urealyticum* and male infertility: an animal model: II. Morphologic changes of testicular tissue at light microscopic level and electron microscopic findings. Andrologia. 21(1):66-75, 1989.

Back S A. Perinatal white matter injury: the changing spectrum of pathology and emerging insights into pathogenic mechanisms. Ment Retard Dev Disabil Res Rev 2006; 12:129-40.

Ballow M, Cates K L, Rowe J C, Goetz C, Desbonnet C. Development of the immune system in very low birth weight (less that 1500 g) premature infants: concentrations of plasma immunoglobulin and patterns of infections. Pediatr Res 20:899-904, 1986.

Banerji et al., Cell, 27:299, 1981.

Banerji et al., Cell, 35:729, 1983.

Berger A, Witt A, Haiden N, Kaider A, Klebermasz K, Fuiko R, Langartner M, Pollak A. lntrauetrine infection with *Ureaplasma* species neuromotor outcome at 1 and 2 years adjusted age in prterm infants. J perinat Med. 2009; 37(1):72-8.

Berkhout et al., Cell, 59:273, 1989.

Biran V, Dumitrescu A M, Doit C, Gaudin A, Bebear C, Boutignon H, Bingen E, Baud 0, Bonacorsi S, Aujard Y. *Ureaplasma paritum* meningitis in a full term newborn. Pediatr Infect Dis J 2010; 29:1154.

Blanar et al., EMBO J., 8:1139, 1989.

Blanchard A, Gautier M. Detection of *Ureaplasma urealyticum* by using the polymerase chain reaction. IOM Lett 1:149, 1990.

Blanchard A, Hentschel J, Duffy L. Baldus K. Cassell G H. Detection of *Ureaplasma urealyticum* by polymerase chain reaction in the urogenital tract of adults in amniotic fluid, and in respiratory tract of newborns. Clin Infect Dis 17 (suppl):S148-53, 1993.

Bodine and Ley, EMBO J., 6:2997, 1987.

Böhm W, KuhrOber A, Paier T, Mertens T, Reimann J, Schirmbeck R. DNA vector constructs that prime hepatitis B surface antigen-specific cytotoxic T lymphocyte and antibody responses in mice after intramuscular injection. Journal of Immunological Methods 193 (1): 29-40, 1996.

Boshart et al., Cell, 41:521, 1985.

Bosze et al., EMBO J., 5:1615, 1986.

Braddock et al., Cell, 58:269, 1989.

Brown M B, Cassell G H, Taylor-Robinson D, et al. Measurement of antibody to *Ureaplasma Urealyticum* by an enzyme linked immunosorbant assay and detection of antibody response in patients with non-gonococcal urethritis. J Clin Microbiol 14:582-4, 1981.

Bulla and Siddiqui, J. Virol., 62:1437, 1986.

Busolo F, Zanchetta R, Bertoloni G. Mycoplasmic localization patterns on spermatozoa from infertile men. Fertil Steril. 42(3):412-7.1984.

Campbell and Villarreal, Mol. Cell. Biol., 8:1993, 1988.

Campere and Tilghman, Genes and Dev., 3:537, 1989.

Campo et al., Nature, 303:77, 1983.

Carey J C, Blackwelder W C, Nugent R P, et al. Antepartum cultures for *Ureaplasma urealyticum* are not useful in predicting pregnancy outcome. Am J Obstet Gynecol 164:728-33, 1991.

Cassell G H, Crouse D T, Waites K B, Rudd P T, Davis J K. Does *Ureaplasma urealyticum* cause respiratory disease in the newborn? Pediatr Infect Dis J 7:535-41, 1988.

Cassell G H, Davis R O, Waites K B, Brown M B. Marriott P A. Stagno S. Davis J K. Isolation of *Mycoplasma hominis* and *Ureaplasma urealyticum* from amnioticfluid at 16-20 weeks gestation: potential effect on outcome of pregnancy. Sex Transm Dis 10:294-302, 1983.

Cassell G H, Waites K B, Crouse D T, Rudd P T, Canull K C, Stagno S, Cutter G R. Association of *Ureaplasma urealyticum* infection of the lower respiratory tract with chronic lung disease and death in very low birth weight infants. Lancet ii:240-4, 1988.

Cassell G H, Waites K B, Watson H L, Crouse D T, Harasawa R. *Ureaplasma urealyticum* intrauterine infection: role in prematurity and disease in newborns. Clin Microbiol Rev 6:69-87, 1993.

Celander and Haseltine, J. Virology, 61:269, 1987.

Celander et al., J. Virology, 62:1314, 1988.

Chandler et al., Cell, 33:489, 1983.

Chang et al., Mol. Cell. Biol., 9:2153, 1989.

Chatterjee et al., Proc. Nat'l Acad. Sci. USA., 86:9114, 1989.

Choi et al., Cell, 53:519, 1988.

Chung H Y, Chung J I N, Chun S H, Sung H S, Kim M N, Kim K S. A case of erythromycin-resistant *Ureaplasma urealyticum* meningitis in a premature infant. Korean J Lab Med 27:46-9, 2007.

Cinatl J Jr, Michaelis M, Doerr H W. The threat of avian influenza A (H5N1). Part IV: Development of vaccines. Med Microbiol Immunol. 196(4):213-25, 2007.

Clifford V, Tebruegge M, Everest N, Curtis N. *Ureaplasma*: pathogen or passenger in neonatal meningitis? Pediatr Infect Dis J 29:60-4, 2010.

Cohen et al., "A Repetitive Sequence Element 3□ of the human c-Ha-ras1 Gene Has Enhancer Activity," J. Cell. Physiol., 5:75, 1987.

Costa et al., Mol. Cell. Biol., 8:81, 1988.

Cripe et al., EMBO J., 6:3745, 1987.

Culotta and Hamer, Mol. Cell. Biol., 9:1376, 1989.

Cunliffe N A, Fergusson S, Davidson F, Lyon A, Ross P W. Comparison of culture with the polymerase chain reaction for detection of *Ureaplasma urealyticum* in endotracheal aspirates of preterm infants. J Med Microbiol 45:27-30, 1996.

Dammann 0, Leviton A. Maternal intrauterine infection, cytokines, and brain damage in the preterm newborn. Pediatr Res. 42(1):1-8, 1997.

Dandolo et al., J. Virology, 47:55, 1983.

De Villiers et al., Nature, 312:242, 1984.

Deschamps et al., Science, 230:1174, 1985.

Domingues D, Tavira L T, Duarte A, Sanca A, Prieto E, Exposto F. *Ureaplasma urealyticum* biovar determination in women attending a family planning clinic in Guine-Bissau, using polymerase chain reaction of the multiple-banded antigen gene. J Clin Lab Anal. 16(2):71-5, 2002.

Echahidi F, Muyldermans G, Lauwers S, Naessens A. Development of an enzyme-linked immunosorbent assay for serotyping *ureaplasma urealyticum* strains using monoclonal antibodies. Clin Diagn Lab Immunol. 8(1): 52-7, 2001.

Edbrooke et al., Mol. Cell. Biol., 9:1908, 1989.

Edlund et al., Science, 230:912, 1985

Engel S, Bollmann R, Sokolowska-KOhler W, Audring H, Klug H. *Ureaplasma urealyticum* and male infertility: an animal model. I. Artificial infection, breeding experiments and histological preparation of organs. Andrologia. 20(6): 467-71, 1988.

Eschenbach D A, Nugent R P, Rao A V. A randomized placebo controlled trial of erythromycin for the treatment of *Ureaplasma urealyticum* to prevent premature delivery. Am J Obstet Gynecol 164:734-42, 1991.

Eschenbach D A. *Ureaplasma urealyticum* and premature birth. Clin Infect Dis 17:100-106, 1993.

Feng and Holland, Nature, 334:6178, 1988.

Firak and Subramanian, Mol. Cell. Biol., 6:3667, 1986.

Foecking and Hofstetter, "Powerful and/or Versatile Enhancer-Promoter Unit for [mammalian, plant, fungus, bacteria?] Expression Vectors," Gene, 45:101, 1986.

Font G E, Gauthier D W, Meyer W J, Myles T D. Janda W. Bieniarz A. Catalase activity as a predictor of amniotic fluid culture results in preterm labor or rupture of membranes. Obstet Gynecol 85:656-8, 1995.

"Fort Dodge Animal Health Announces Approval of West Nile Virus DNA Vaccine for Horses". PR Newswire. 2005, Jul. 18. http://www.highbeam.com/doc/1G1-134116417.html.

Fujita et al., Cell, 49:357, 1987.

Furness G. T-mycoplasmas. Factors affecting their growth, colonial morphology, and assay on agar. J Infect Dis 128:703-9, 1973.

Furr P M, Taylor-Robinson D. Factors influencing the ability of different mycoplasmas to colonize the genital tract of hormone-treated female mice. Int J Exp Pathol. 74(1):97-101, 1993.

Fynan E F, Webster R G, Fuller D H, Haynes J R, Santoro J C, Robinson H L. DNA vaccines: protective immunizations by parenteral, mucosal, and gene-gun inoculations. Proc Natl Acad Sci USA 90 (24): 11478-82, 1993.

Garland S M, Murton U. Neonatal meningitis caused by *Ureaplasma urealyticum*. Pediatr Infect Dis J 1987; 6:868-70.

Gilles et al., Cell, 33:717, 1983.

Gloss et al., EMBO J., 6:3735, 1987.

Godbout et al., Mol. Cell. Biol., 8:1169, 1988.

Goodbourn and Maniatis, Proc. Nat'l Acad. Sci. USA, 85:1447, 1988.

Goodbourn et al., Cell, 45:601, 1986.

Gray D J, Robinson H B, Malone J, Thomson R B Jr. Adverse outcome in pregnancy following amniotic fluid isolation of *Ureaplasma urealyticum*. Prenat Diagn 12:111-7, 1992.

Greene et al., Immunology Today, 10:272, 1989.

Grosschedl and Baltimore, Cell, 41:885, 1985.

Gupta V, Dhawan B, Khanna N, Agarwal N, Bhattacharya S N, Sreenivas V, Chaudhry R. Detection and biovar discrimination of *Ureaplasma urealyticum* in Indian patients with genital tract infections. Diagn Microbiol Infect Dis. 60(1):95-7, 2008.

Haslinger and Karin, Proc. Nat'l Acad. Sci. USA., 82:8572, 1985.

Hauber and Cullen, J. Virology, 62:673, 1988.

Hazan Y, Mazor M, Horowitz 5, Wiznitzer A. Kuperman O. Meril C. Glezerman M. The diagnostic value of amniotic fluid Gram stain examination and limulus amebocyte lysate assay in patients with preterm birth. Acta Obstet Gynecol Scand 74:275-80, 1995.

Hen et al., Nature, 321:249, 1986.

Hensel et al., Lymphokine Res., 8:347, 1989.

Hentschel J, Abele-Horn, Peters J. *Ureaplasma urealyticum* in the cerebrospinal fluid of a premature infant. Acta Paediatr 82:690-3, 1993.

Herr and Clarke, Cell, 45:461, 1986.

Hipp S S, Henriques E, Rockwood L. Matties G. Persistence of *Ureaplasma urealyticum* in the genital tract after antibiotic therapy. J Reprod Med 28:319-24, 1983.

Hirochika et al., J. Virol., 61:2599, 1987.

Hirsch et al., Mol. Cell. Biol., 10:1959, 1990.

Holbrook et al., Virology, 157:211, 1987.

Horlick and Benfield, Mol. Cell. Biol., 9:2396, 1989.

Horowitz S, Mazor M, Romero R, Horowiz J, Glezerman M. Infection of the amniotic cavity with *Ureaplasma urealyticumin* the midtrimester of pregnancy. J Reprod Med 40:375-9, 1995.

Huang et al., Cell, 27:245, 1981.

Hug H, Costas M, Staeheli P, Aebi M, et al. Organization of the murine Mx gene and characterization of its interferon- and virus-inducible promoter. Mol Cell Biol 1988 August; 8(8): 3065-79.

Hwang et al., Mol. Cell. Biol., 10:585, 1990.

Imagawa et al., Cell, 51:251, 1987.

Imbra and Karin, Nature, 323:555, 1986.

Imler et al., Mol. Cell. Biol., 7:2558, 1987.

Iwasaka T, Wada T, Sugimori H. Enhancement of colonization of *Ureaplasma urealyticum* in the mouse genital tract by estrogen treatment. Am J Obstet Gynecol. 155(5): 1124-7, 1986.

Jakobovits et al., Mol. Cell. Biol., 8:2555, 1988.

Jameel and Siddiqui, Mol. Cell. Biol., 6:710, 1986.

Jaynes et al., Mol. Cell. Biol., 8:62, 1988.

Johnson et al., Mol. Cell. Biol., 9:3393, 1989.

Joussemet B, Vu A T, Sai P, Bach J M. Gene-gun biolistic immunization encoding glutamic acid decarboxylase: a model for studying Langerhans cell abnormalities and mimicry in the nonobese diabetic mouse. Ann N Y Acad Sci. 1051:613-25, 2005.

Kadesch and Berg, Mol. Cell. Biol., 6:2593, 1986.

Karin et al., Mol. Cell. Biol., 7:606, 1987.

Katinka et al., Cell, 20:393, 1980.

Katinka et al., Nature, 290:720, 1981.

Kaukola T, Herva R, Perhomaa M, Paakko E, Kingsmore S, Vainionpad L, Hallman M. Population cohort associating chorioamnionitis, cord inflammatory cytokines and neurologic outcome in very preterm, extremely low birth weight infants. Pediatr Res. 59(4478-83, 2006.

Kawamoto et al., Mol. Cell. Biol., 8:267, 1988.

Kenny G E, Cartwright F D. Susceptibilities of *Mycoplasma hominis, Mycoplasma pneumoniae*, and *Urealplasma urealyticum* to new glycylcyclines in comparison with older tetracyclines. Antimicrob Agents Chemother 38:2628-32, 1994.

Kenny G E, Cartwright F D. Susceptibilities of *Mycoplasma pneumoniae, Mycoplasma hominis*, and *Urealplasma urealyticum* to a new quinolone, trovafloxacin (CP-99,219). Antimicrob Agents Chemother 40:1048-9, 1996.

Kiledjian et al., Mol. Cell. Biol., 8:145, 1988.

Klamut et al., Mol. Cell. Biol., 10:193, 1990.

Knox C L, Dando S J, Nitsos I, Kallapur S G, Jobe A H, Payton D, Moss T J, Newnham J P. The severity of chorioamnionitis in pregnant sheep is associated with in vivo variation of the surface-exposed multiple-banded antigen/gene of *Ureaplasma parvum*. Biol Reprod. 83(3): 415-26, 2010.

Koch et al., Mol. Cell. Biol., 9:303, 1989.

Kong F, Ma Z, James G, Gordon S, Gilbert G L. Molecular genotyping of human *Ureaplasma* species based on multiple-banded antigen (MBA) gene sequences. Int J Syst Evol Microbiol. 50 Pt 5:1921-9, 2000.

Kong F, Zhu X, Wang W, Zhou X, Gordon 5, Gilbert G L. Comparative analysis and serovar-specific identification of multiple-banded antigen genes of *Ureaplasma urealyticum* biovar 1. J Clin Microbiol. 37(3):538-43, 1999.

Kong L, Markham T, Leeming A H, Weisman L E. Approriate antibiotic treatment improves *ureaplasma* infection outcome in the neonatal mouse. European Society for Pediatric Infectious Diseases Program. Abst. May 16, 2008.

Kraus J, Woltje M, Schonwetter N, Hollt V. Alternative promoter usage and tissue specific expression of the mouse somatostatin receptor 2 gene. FEBS Lett 1998 May 29; 428(3):165-70.

Kraus S J, Jacobs N F, Chandler F W, Arum E S. Experimental animal infections with *Mycoplasma hominis* and *Ureaplasma urealyticum*. Infect Immun 16(1):302-9, 1977.

Krause D C, Taylor-Robinson D. Mycoplasmas which infect humans. pp 417-44. In J Maniloff (ed.), Mycoplasmas: Molecular Biology and Pathogenesis. American Society for Microbiology, Washington, D.C., 1992.

Kriegler and Botchan, Mol. Cell. Biol., 3:325, 1983.

Kriegler and Botchan, In: Eukaryotic Viral Vectors, Y. Gluzman, ed., Cold Spring Harbor: Cold Spring Harbor Laboratory, N Y, 1982.

Kriegler et al., Cell, 38:483, 1984a.

Kriegler et al., Cell, 53:45, 1988.

Kriegler et al., In: Cancer Cells 2/Oncogenes and Viral Genes, Van de Woude et al. eds, Cold Spring Harbor, Cold Spring Harbor Laboratory, 1984b.

Kriegler et al., In: Gene Expression, D. Hamer and M. Rosenberg, eds., New York: Alan R. Liss, 1983.

Kuhl et al., Cell, 50:1057, 1987.

Kundsin R B, Leviton A, Allred E N, Poulin S A. *Ureaplasma urealyticum* infection of the placenta in pregnancies that ended prematurely. Obstet Gynecol 87:122-7, 1996.

Kunz et al., Nucl. Acids Res., 17:1121, 1989.

Kutzler M A, Weiner D B. DNA vaccines: ready for prime time? Nat Rev Genet. October, 9(10):776-88, 2008.

Lareyre J J, Thomas T Z, Zheng W L, Kasper S, et al. A 5-kilobase pair promoter fragment of the murine epididymal retinoic acid-binding protein gene drives the tissue-specific, cell-specific, and androgen-regulated expression of a foreign gene in the epididymis of transgenic mice. J Biol Chem 1999 Mar. 19; 274(12):8282-90.

Larsen et al., Proc. Nat'l Acad. Sci. USA., 83:8283, 1986.

Laspia et al., Cell, 59:283, 1989.

Latimer et al., Mol. Cell. Biol., 10:760, 1990.

Lee et al., "Activation of beta3-adrenoceptors by exogenous dopamine to lower glucose uptake into rat adipocytes," J Auton Nerv Syst. 74(2-3):86-90, 1997.????

Lee et al., Mol. Endocrinol., 2: 404-411, 1988.

Lee et al., Nature, 294:228, 1981.

Lee S H, Wang W, Yajima S, Jose P A, et al. Tissue-specific promoter usage in the D1A dopamine receptor gene in brain and kidney. DNA Cell Biol 1997 November; 16(11): 1267-75.

Leitner W W, Seguin M C, Ballou W R, Seitz J P, Schultz A M, Sheehy M J, Lyon J A. Immune responses induced by intramuscular or gene gun injection of protective deoxyribonucleic acid vaccines that express the circumsporozoite protein from *Plasmodium berghei* malaria parasites. The Journal of Immunology. 159 (12): 6112-6119, 1997.

Levinson et al., Nature, 295:79, 1982.

Leviton A, Paneth N, Reuss M L, Susser M, Allred E N, Dammann 0, Kuban K, Van Marter U, Pagano M, Megyi T, Hiatt M, Sanocka U, Shahrivar F, Abiri M, Disalvo D, Doubilet P, Kairam R, Kazam E, Kirpekar M, Rosenfeld D, Schonfeld S, Share J, Collins M, Genest D, Shen-Schwarz 5, et al. Maternal infection, fetal inflammatory response, and brain damage in very low birth weight infants. Developmental Epidemiology Network Investigators. Pediatr Res. 46(5):566-75, 1999.

Lewis P J, Babiuk L A. DNA Vaccines: A Review. Advances in Virus Research 54: 129, 1999.

Li Y H, Chen M, Brauner A, Zheng C, Skov Jensen J, Tullus K. *Ureaplasma urealyticum* induces apoptosis in human lung epithelial cells and macrophages. Biol Neonate. 82(3):166-73, 2002.

Lin et al., Mol. Cell. Biol., 10:850, 1990.

Luria et al., EMBO J., 6:3307, 1987.

Lusky and Botchan, Proc. Nat'l Acad. Sci. USA., 83:3609, 1986.

Lusky et al., Mol. Cell. Biol., 3:1108, 1983.

Luton D. Ville Y. Luton-Sigy A. Cousin C. Narraido B. Fassasi-Jarretou A. Escarguel C. Prevalence and influence of *Mycoplasma hominis* and *Ureaplasma urealyticum* in 218 African pregnant women and their infants. Eur J. Obstet Gynecol 56:95-101, 1994.

Majors and Varmus, Proc. Nat'l Acad. Sci. USA., 80:5866, 1983.

Masover G K, Palant M, Zerrudo Z, hayflick L. Interaction of *Ureaplasma urealyticum* with eukaryotic cells in vitro. In: Non-gonococcal urethritis and relted infections. Edited by Hobson D & Holmes K K. Washington; American Society for Microbiology, 1977.

Mazor M. Chaim W. Horowitz S. Leiberman J R. Glezerman M. Successful treatment of preterm labour by eradication of *Ureaplasma urealyticum* with erythromycin. Archiv Gynecol Obstet. 253:215-8, 1993.

McGarrity G J, Kotani H. *Ureaplasma*-eukaryotic cell interactions in vitro. Pediatr Infect Dis. 5(6 Suppl):5316-8, 1986.

McNeall et al., Gene, 76:81, 1989.

Miksicek et al., Cell, 46:203, 1986.

Mohler H. Molecular regulation of cognitive functions and developmental plasticity: impact of GABAA receptors. J Neurochem. 2007 102:1-12. Neuman M, Esanu A. Gaps and perspectives of new fluoroquinolones. Drugs Exp Clin Res. 1988; 14(6):385-91.

Molina T L, Kong L, Weisman L E. Placenta *Ureaplasma* increases BPD or Death in high risk neonates. Journal of Perinatology. 2010, October (abst), 2010.

Monecke S, Helbig J H, Jacobs E. Phase variation of the multiple banded protein in *Ureaplasma urealyticum* and *Ureaplasma parvum*. Int J Med Microbiol. 293(2-3):203-11 (abst), 2003.

Mor G, Klinman D M, Shapiro S, Hagiwara E, Sedegah M, Norman J A, Hoffman S L, Steinberg A D. Complexity of the cytokine and antibody response elicited by immunizing mice with *Plasmodium yoelii* circumsporozoite protein plasmid DNA. The Journal of Immunology 155 (4): 2039-2046, 1995.

Mordacq and Linzer, Genes and Dev., 3:760, 1989.

Moreau et al., Nucl. Acids Res., 9:6047, 1981.

Muesing et al., Cell, 48:691, 1987.

Muthumani K, Zhang D, Dayes N S, Hwang D S, Calarota S A, Choo A Y, Boyer J D, Weiner D B. Novel engineered HIV1 East African Clade-A gp160 plasmid construct induces strong humoral and cell-mediated immune responses in vivo. Virology. 314 (1). 134. 2003.

Neal T J, Roe M F, Shaw N J. Spontaneously resolving *Ureaplasma urealyticum* meningitis. Eur J Pediatr 15:342-3, 1994.

Ng et al., Nuc. Acids Res., 17:601, 1989.

Nomoto S, Tatematsu Y, Takahashi T, Osada H. Cloning and characterization of the alternative promoter regions of the human LIMK2 gene responsible for alternative transcripts with tissue-specific expression. Gene 1999 Aug. 20; 236 (2):259-71.

Normann E, Lacaze-Masmonteil T, Eaton F, Schwendimann L, Gressens P, Thébaud B. A novel mouse model of *Ureaplasma*-induced perinatal inflammation: effects on lung and brain injury. Pediatr Res. 65(4):430-6, 2009.

Novy M J, Duffy L, Axthelm M K, Sadowsky D W, Witkin S S, Gravett M G, Cassell G H, Waites K B. *Ureaplasma parvum* or *Mycoplasma hominis* as sole pathogens cause chorioamnionitis, preterm delivery, and fetal pneumonia in rhesus macaques. Reprod Sci. 16(1):56-70, 2009.

Okunola 0, Kong K, Fontenot T, Venkatesh M P, Weisman L E. *Ureaplasma* Colonization of the Placenta and Preterm Birth. E-PAS 5906.3, 2007.

Okunola 0. Kong L, Fontenot T, Venkatesh M P, Adams K, Weisman L E. *Ureaplasma urealyticum* (Uu) colonization of the placenta is associated with adverse perinatal outcome. E-PAS 2853.162 (abst), 2006.

O'Leary W M. Ureaplasmas and human disease. Crit Rev Microbiol. 17(3):161-8, 1990.

Ollikainen J, Hiekkaniemi H, Korppi M, Katila M L, Heinonen K. *Ureaplasma urealyticum* cultured from brain tissue of preterm twins who died of intraventricular hemorrhage. Scand J Infect Dis. 1993; 25(4):529-31, 1993.

Olomu I N, Hecht J L, Onderdonk A O, Allred E N, Leviton A; Extremely Low Gestational Age Newborn Study Investigators. Perinatal correlates of *Ureaplasma urealyticum* in placenta parenchyma of singleton pregnancies that end before 28 weeks of gestation. Pediatrics. 123(5): 1329-36, 2009.

Ondek et al., EMBO J., 6:1017, 1987.

Ornitz et al., Mol. Cell. Biol., 7:3466, 1987.

Palmiter et al., Nature, 300:611, 1982.

Pech et al., Mol. Cell. Biol., 9:396, 1989.

Perez-Stable and Constantini, Mol. Cell. Biol., 10:1116, 1990.

Picard and Schaffner, Nature, 307:83, 1984.

Pinkert et al., Genes and Dev., 1:268, 1987.

Pinna G S, Skevaki C L, Kafetzis D A. The significance of *Ureaplasma urealyticum* as a pathogenic agent in the paediatric population. Curr Opin Infect Dis. 19(3):283-9, 2006.

Pollack J D. Metabolic distinctiveness of ureaplasmas. Pediatr Infect Dis J 5(suppl):305-7, 1986.

Ponta et al., Proc. Nat'l Acad. Sci. USA., 82:1020, 1985.

Porton et al., Mol. Cell. Biol., 10:1076, 1990.

Queen and Baltimore, Cell, 35:741, 1983.

Quinn et al., Mol. Cell. Biol., 9:4713, 1989.

Quinn P A. Evidence of an immune response *Ureaplasma urealyticum* in perinatal morbidity and mortality. Pediatr Infect Dis J 5:S282-7, 1986.

Quinn P A, Rubin S, Li H C S, Nocilla D M, Read S E, Chipman M. Serological evidence of *Ureaplasma urealyticum* infection in neonatal respiratory disease. Yale J Biol Med 56:565-72, 1986.

Quinn P A, Shewchuk A B, Shuber J, Lie K I, Ryan E, Sheu M, Chipman M L. Serologic evidence of *Ureaplasma urealyticum* infection in women with spontaneous pregnancy loss. Am J Obstet Gynecol 145:245-50, 1983.

Rao R P, Ghanayem N S, Kaufman B A, Kehl K S, Gregg D C, Chusid M J. *Mycoplasma hominis* and *Ureaplasma* species brain abscess in a neonate. Pediatr Infect Dis J. 21(11):1083-5, 2002.

Redline R W, Wilson-Costello D, Borawski E, Fanaroff A A, Hack M. Placental lesions associated with neurologic impairment and cerebral palsy in very low-birth-weight infants. Arch Pathol Lab Med. 122(12):1091-8, 1998.

Redondo et al., Science, 247:1225, 1990.

Reisman and Rotter, Mol. Cell. Biol., 9:3571, 1989.

Remington's Pharmaceutical Sciences, 18th Ed. Mack Printing Company, 1990.

Resendez Jr. et al., Mol. Cell. Biol., 8:4579, 1988.

Ripe et al., Mol. Cell. Biol., 9:2224, 1989.

Rittling et al., Nucl. Acids Res., 17:1619, 1989.

Roberts M C, Hooton M, Stamm W, Holmes K K, Kenny G E. DNA probes for the detection of mycoplasmas in genital specimens. Isr J Med Sci 23:618-20, 1987.

Robertson J A, Bromothymol blue broth: improved medium for detection of *Ureaplasma urealyticum*. J Clin Microbiol 7:127-32, 1978.

Robertson J A, Pyle L, Kakulphimp J, Stemke G W, Finch L R. The genomes of the genus *Ureaplasma*. IOM Lett 1:72-3, 1990.

Robertson J A, Stemke G W. Expanded serotyping scheme for *Ureaplasma urealyticum* strains isolated from humans. J Clin Microbiol 15:873-8, 1982.

Robertson J A, Stemke G W, Davis J W Jr, Harasawa R, Thirkell D, Kong F, Shepard M C, Ford D K Proposal of *Ureaplasma* Hemadsorption by colonies of *Ureaplasma urealyticum*. Infect Immun 59(6):2203-6, 1991.

Robertson J A. Stemke G W, Davis J W Jr, Harasawa R, Thirkell D, Kong F, Shepard M C, Ford D K. Proposal of *Ureaplasma parvum* sp nov. an amended description of *Ureaplasma urealyticum* (Shepard et al 1974 Robertson et al 2001. Int J Syst Evol Microbiol. 52(Pt 2):587-97, 2002.

Robinson H L, Pertmer T M. DNA vaccines for viral infections: basic studies and applications. Adv. Virus Res. 55: 1-74, 2000.

Rodriguez F, Zhang J, Whitton J L. DNA immunization: ubiquitination of a viral protein enhances cytotoxic T lymphocyte induction and antiviral protection but abrogates antibody induction. Journal of Virology 71 (11): 8497, 1997.

Romero R, Sibai B, Caritis S. Antibiotic treatment of preterm labor with intact membranes: A multicenter, randomized, double-blinded, placebo-controlled trial. Am J Obstet Gynecol 169:764-774, 1993.

Rosen et al., Cell, 41:813, 1988.

Saada A B, Terespolski Y, Adoni A, Kahane I. Adherence of *Ureaplasma urealyticum* to human erythrocytes. Infect Immun 59(1):467-9, 1991.

Samaco R C, Fryer J D, Ren J, Fyffe S, Chao H T, Sun Y, Greer A, Zoghbi H Y, Neul J L. A partial loss of function allele of methyl-CpG-binding protein 2 predicts a human neurodevelopmental syndrome. Hum Mai Genet. 17:1718-27, 2008.

Satake et al., "Biological Activities of Oligonucleotides Spanning the F9 Point Mutation Within the Enhancer Region of Polyoma Virus DNA," J. Virology, 62:970, 1988.

Schaffner et al., J. Mol. Biol., 201:81, 1988.

Searle et al., Mol. Cell. Biol., 5:1480, 1985.

Sedegah M, Hedstrom R, Hobart P, Hoffman S L. Protection against Malaria by Immunization with Plasmid DNA Encoding Circumsporozoite Protein. PNAS. 91 (21): 9866-9870, 1994.

Sethi S, Sharma M, Narang A, Aggrawal P B. Isolation pattern and clinical outcome of genital *mycoplasma* in neonates from a tertiary care neonatal unit. J Trap Med 45:143-5, 1999.

Sharp and Marciniak, Cell, 59:229, 1989.

Shaul and Ben-Levy, EMBO J., 6:1913, 1987.

Shepard M C. Culture media for ureaplasmas. pp 137-46. In S. Razin and J G Tully (ed.), Methods in Mycoplasmology, vol 1. Academic Press. New York. 1983.

Shepard M C, Masover G K. Special features of ureaplasmas. pp 451-494. In MF Barile and S. Razin (ed.), The Mycoplasmas, vol 1. Academic Press, New York, 1979.

Sherman et al., Mol. Cell. Biol., 9:50, 1989.

Shimizu T, Kida Y, Kuwano K. *Ureaplasma parvum* lipoproteins, including MB antigen, activate NF-{kappa}B through TLR1, TLR2 and TLR6. Microbiology. 154(Pt 5):1318-25, 2008.

Silva F, Passarinha L, Sousa F, Queiroz J A, Domingues F C. Influence of growth conditions on plasmid DNA production. J Microbiol Biotechnol. 19(11):1408-14, 2009.

Singh J, Arrieta A, lang D J. Neonate with chronic meningitis and hydrocephalus. Pediatr Infect Dis J 22:1025-6, 2003.

Sleigh and Lockett, J. EMBO, 4:3831, 1985.

Smith D G, Russell W C, Thirkell D. Adherence of *Ureaplasma urealyticum* to human epithelial cells. Microbiology. 140 (10):2893-8, 1994.

Spalholz et al., Cell, 42:183, 1985.

Spandau and Lee, J. Virology, 62:427, 1988.

Spandidos and Wilkie, EMBO J., 2:1193, 1983.

Spencer, C. M., Alekseyenko, 0., Serysheva, E., Yuva-Paylor, L. A., and Paylor, R. Altered anxiety-related and social behaviors in the Fmr1 knockout mouse model of fragile X syndrome. Genes Brain Behav. 4:420-30, 2005.

Spencer, G. M., Serysheva, E., Yuva-Paylor, L. A., Oostra, B. A., Nelson, D. L., and Paylor, R. (2006). Exaggerated behavioral phenotypes in Fmr1/Fxr2 double knockout mice reveal a functional genetic interaction between Fragile X-related proteins. Hum. Md. Genet. 15:1984-94, 2006.

Stahelin-Massik J, Levy F, Friderich P, Schaab U B. Meningitis caused by *Ureaplasma urealyticum* in a full term neonate. Pediatr Infect Dis J 13:419-21, 1994.

Stemke G W, Robertson J A. Problems associated with serotyping *Ureaplasma urealyticum*. Diagn Microbiol Infect Dis 3:311-20, 1985.

Stephens and Hentschel, Biochem. J., 248:1, 1987.

Stuart et al., Nature, 317:828, 1985.

Stuve 0., Eagar T N, Frohman E M, Cravens P D. DNA Plasmid Vaccination for Multiple Sclerosis. Archives of Neurology 64 (10): 1385, 2007.

Sullivan and Peterlin, Mol. Cell. Biol., 7:3315, 1987.

Swartzendruber and Lehman, J. Cell. Physiology, 85:179, 1975.

Swenson C E, O'Leary W M. An animal model for the study of infectious human infertility. Feral Steril. 29(4):462-3, 1978.

Takebe et al., Mol. Cell. Biol., 8:466, 1988.

Tavernier et al., Nature, 301:634, 1983.

Taylor and Kingston, Mol. Cell. Biol., 10:165, 1990a.

Taylor and Kingston, Mol. Cell. Biol., 10:176, 1990b.

Taylor et al., J. Biol. Chem., 264:15160, 1989.

Taylor Robinson D, Haig D A, Williams M H. Bovine T-strain *mycoplasma*. Ann NY Acad Sci 143:517-8, 1967.

Taylor-Robinson D. Genital *mycoplasma* infections pp 501-523. In F N Judson (ed.), Clinics in Laboratory Medicine, vol 9. Sexually Transmitted Diseases. WB Saunders Co. Philadelphia. 1989.

Taylor-Robinson D, Furr P M, Webster D B. *Urealplasma urealyticum* in the immunocompromised host. Pediatr Infect Dis J 5:5236-8, 1986.

Taylor-Robinson D, Gourlay R N. The Mycoplasmas. Genus II. *Ureaplasma*. pp 770-775. In N R Krieg and J G Holt (ed.), Bergey's Manual of Systematic Bacteriology, vol. 1. Williams & Wilkins, Baltimore, 1984.

Teng L J, Zheng X, Glass J I, Watson H L, Tsai J, Cassell G H. J. *Ureaplasma urealyticum* biovar specificity and diversity are encoded in multiple-banded antigen gene. Clin Microbiol. 32(6):1464-9, 1994.

Thiesen et al., J. Virology, 62:614, 1988.

Thirkell D A, Myles D, Russell W C. Serotype 8- and serocluster-specific surface-expressed antigens of *Ureaplasma urealyticum*. Infect lmmun 57:1607-1701, 1989.

Torres-Morquecho A, Rivera-Tapia A, Gonzalez-Velazquez F, Torres J, Chavez-Mungula B, Cedillo-Ramirez L, Giono-Cerezo S. Adherence and damage to epithelial cells of human lung by *Ureaplasma urealyticum* strains biotype 1 and 2. African J Microbiol Res. 4(6):480-92, 2010.

Treisman, Cell, 42:889, 1985.

Tronche et al., Mol. Biol. Med., 7:173, 1990.

Tronche et al., Mol. Cell. Biol., 9:4759, 1989.

Trudel and Constantini, Genes and Dev., 6:954, 1987.

Tsumaki N, Kimura T, Tanaka K, Kimura J H, et al. Modular arrangement of cartilage- and neural tissue-specific cis-elements in the mouse alpha2(XI) collagen promoter. J Biol Chem 1998 Sep. 4; 273(36):22861-4.

Turunen H, Leinikki P, Jansson E. Serological characterization of *Ureaplasma urealyticum* strains by enzyme-linked immunosorbant assay (ELISA). J Clin Pathol 35:439-43, 1982.

Tyndall et al., Nuc. Acids. Res., 9:6231, 1981.

Valencia G B, Banzon F, Cummings M, McCormack W M, Glass L, Hammerschlag M R. *Anycoplasma hominis* and *Ureaplasma urealyticum* in neonates with suspected infection. Pediatr Infect Dis J. 12(7):571-3, 1993.

Vancutsem E, Echahidi F, Van Geel K, Muyldermans G, Soetens 0, Naessens A. Production of recombinant antigens of *Ureaplasma parvum* serotypes 3 and 6 for development of a serological assay. Clin Vaccine Immunol. 15(3):447-51, 2008.

Vannice and Levinson, J. Virology, 62:1305, 1988.

Vasseur et al., Proc. Nat'l Acad. Sci. USA., 77:1068, 1980.

Viscardi R M, Hashmi N, Gross G W, Sun C C, Rodriguez A, Fairchild K D. Incidence of invasive *Ureaplasma* in VLBW infants: relationship to severe intraventricular hemorrhage. J Perinatal 28:759-65, 2008.

Viscardi R M. *Ureaplasma* species: role in diseases of prematurity. Clin Perinatal. 37(2):393-409, 2010.

Volger L B, Waites K B, Wright P F, Cassell G H. *Urealplasma urealyticum* polyarthritis in agammaglobulinemia. Pediatr Infect Dis 4:687-91, 1985.

Waites K B, Cassell G H, Duffy L B, Searcey K B. Isolation of *Ureaptasma urealyticum* from low birth weight infants. J Pediatr 126:502-504, 1995.

Waites K B, Duffy L B, Grouse D T, Dworsky M E, Strange M J, Nelson K G, Cassell G H. Mycopiasmal infections of cerebrospinal fluid in newborn infants from a community hospital population. Pediatr Infect Dis J. 9:241-5, 1990.

Waites K B, Katz B, Schelonka R L. Mycoplasmas and ureaplasmas as neonatal pathogens. Clin Microbiol Rev. 18(4):757-89, 2005.

Waites K B, Rudd P T Crouse D T, et al. Chronic *Ureaplasma urealyticum* and *Mycoplasma hominis* infections of the central nervous system in preterminfants. Lancet. 1:17-21, 1988.

Walls S A, Kong L, Leeming H A, Placencia F X, Popek E J, Weisman L E. Antibiotic prophylaxis improves *Ureaplasma* associated lung disease in suckling mice. Pediatr Res. 66(2):197-202, 2009.

Wang and Calame, Cell, 47:241, 1986.

Watase K, Gatchel J R, Sun Y, Emamian E, Atkinson R, Richman R, Mizusawa H, Orr H T, Shaw C, Zoghbi H Y. Lithium therapy improves neurological function and hippocampal dendritic arborization in a spinocerebellar ataxia type 1 mouse model. PLoS Med. 4(5):el 82, 2007.

Watson H L, Blalock D K, Cassell G H. Variable antigens of *Ureaplasma urealyticum* containing both serovar-specific and serovar-cross-reactive epitopes. Infect Immun 58:3679-88, 1990.

Weber et al., Cell, 36:983, 1984.

Weinberger et al. Mol. Cell. Biol., 8:988, 1984

Weiner D B, Kennedy R C. Genetic vaccines. Scientific American 281 (1): 34-41, 1999.

Weisman L E, Kent D, Leeming A H, Young A E. Natural History of *Ureaplasma* Vaginal Colonization and Placental Infection. E-PAS 3877.412 (abst), 2009.

Weisman L E, Lorenzetti P M. High intravenous doses of human immune globulin suppresses neonatal group B streptococcal immunity in rats. J Pediatr. 115(3):445-50, 1989.

Widera G, Austin M, Rabussay D, Goldbeck C, Barnett S W, Chen M, Leung L, Otten G R, Thudium K, Selby M J. Increased DNA Vaccine Delivery and Immunogenicity by Electroporation In Vivo. The Journal of Immunology 164 (9): 4635-4640, 2000.

Wiley C A Quinn P A. Enzyme linked immunosorbant assay for detection of antibodies to *Ureaplasma urealyticum* serotypes. J Clin Microbiol 19:421-6, 1984.

Willoughby J J, Burdon M G, Thirkell D, Taylor-Robinson D, Russell W C. Use of a pair of PCR primers to detect *Ureaplasma* species in diagnostic situations. 10M Lett 1:467, 1990.

Winoto and Baltimore, Cell, 59:649, 1989.

Wu H K, Squire J A, Song Q, Weksberg R. Promoter-dependent tissue-specific expressive nature of imprinting gene, insulin-like growth factor II, in human tissues. Biochem Biophys Res Commun 1997 Apr. 7; 233(1):221-6.

Wunderlich G, Moura I C, Del Portillo H A. Genetic Immunization of BALB/c mice with a Plasmid Bearing the Gene Coding for a Hybrid Merozoite Surface Protein 1-Hepatitis B Virus Surface Protein Fusion Protects Mice against Lethal *Plasmodium chabaudi* chabaudi PC1 Infection". Infection and Immunity 68 (10): 5839, 2000.

Yutzey et al. "An Internal Regulatory Element Controls Troponin I Gene Expression," Mol. Cell. Biol., 9:1397, 1989.

Zeighami H, Peerayeh S N, Yazdi R S, Sorouri R. Prevalence of *Ureaplasma urealyticum* and *Ureaplasma parvum* in semen of infertile and healthy men. Int J STD AIDS. 20(6):387-90, 2009.

Zhao-Emonet et al., "The equine herpes virus 4 thymidine kinase is a better suicide gene than the human herpes virus 1 thymidine kinase," Gene Ther. 6(9):1638-1642, 1999.

Zhao-Emonet J C, Boyer O, Cohen J L, Klatzmann D. Deletional and mutational analyses of the human CD4 gene promoter: characterization of a minimal tissue-specific promoter. Biochim Biophys Acta 1998 Nov. 8; 1442(2-3):109-19.

Zheng X, Teng U, Watson H L, Glass J I, Blanchard A, Cassell G H. Small repeating units within the *Ureaplasma urealyticum* M B antigen gene encode serovar specificity and are associated with antigen size variation. Infect Immun 63(3):891-8, 1995.

Zimmerman C U, Rosengarten R, Spergser J. *Ureaplasma* antigenic variation beyond MBA phase variation: DNA inversions generating chimeric structures and switching in expression of the MBA nterminal paralogue UU172. Mol Microbiol. 79(3):663-76, 2011.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. Isolated antibodies that specifically bind to and immunologically react with a conserved region of *Ureaplasma* multiple-banded antigen or the 5' end of the multiple-banded antigen, wherein the antibodies are bacteria-neutralizing.

2. The isolated antibodies of claim 1, wherein the antibodies specifically bind to the 5' end of the multiple-banded antigen.

3. The isolated antibodies of claim 1, wherein the antibodies specifically bind to the *Ureaplasma* sequence of SEQ ID No: 4.

4. A kit for detecting the presence of an infection of *Ureaplasma* in a human comprising isolated antibodies that specifically bind to and immunologically react with a conserved region of *Ureaplasma* multiple-banded antigen or the 5' end of the multiple-banded antigen, wherein the antibodies are bacteria-neutralizing, and further comprising an aqueous medium, and at least one container for housing the antibodies and media.

5. A kit as claimed in claim 4, wherein the antibodies specifically bind to the *Ureaplasma* sequence of SEQ ID No: 4.

6. A kit as claimed in claim 4 wherein the antibodies specifically bind to the 5' end of the multiple-banded antigen.

* * * * *